(12) United States Patent
Pietras

(10) Patent No.: US 6,306,832 B1
(45) Date of Patent: Oct. 23, 2001

(54) PEPTIDE ANTIESTROGEN COMPOSITIONS AND METHODS FOR TREATING BREAST CANCER

(75) Inventor: Richard J. Pietras, Sherman Oaks, CA (US)

(73) Assignee: University of California, Oakland, CA (US)

( * ) Notice: Subject to any disclaimer, the term of this patent is extended or adjusted under 35 U.S.C. 154(b) by 0 days.

(21) Appl. No.: 09/419,826

(22) Filed: Oct. 14, 1999

Related U.S. Application Data

(63) Continuation of application No. PCT/US98/07711, filed on Apr. 14, 1998.
(60) Provisional application No. 60/043,545, filed on Apr. 14, 1997.

(51) Int. Cl.[7] .......................... A61K 31/70; A61K 38/00; A61K 38/21; C07K 14/00
(52) U.S. Cl. ................. 514/44; 514/2; 435/7.1; 530/300; 530/350; 530/367.1; 424/88
(58) Field of Search ................ 435/7.1; 530/350, 530/382.1, 300; 514/2, 44; 424/88

(56) References Cited

U.S. PATENT DOCUMENTS

| | | |
|---|---|---|
| 4,720,455 | 1/1988 | Babu et al. . |
| 5,728,534 | 3/1998 | Mendelsohn et al. . |

OTHER PUBLICATIONS

Lawrence et al, "Induction of histamine release from human skin mast cells by bradykinin analogs", Biochemical Pharmacol. 38(2):227–33. Abstract only, Jan. 1989.*
Chang et al, "Dissection of the LXXLL nuclear receptor coactivator interaction motif using combinatorial peptide libraries: discovery of peptide antagonists of estrogen receptors alpha and beta", Mol. Cell. Biol. 19(12):8226–8239, Dec. 1999.*
Dermer, "Another anniversary for the war on cancer", Biotechnology 12:320, Mar. 1994.*
Chabert et al, "Cell culture of tumors alters endogenous poly (ADPR) polymerase expression and activity", Int. J. Cancer 53:837–842, Feb. 1993.*
Arnold and Notides, "An antiestrogen: a phosphotyrosyl peptide that blocks dimerization of the human estrogen receptor," Proc Natl. Acad. Sci. USA, 92:7475–7479, 1995.
Arnold et al., "Phosphorylation of tyrosine 537 on the human estrogen receptor is required for binding to an estrogen response element," J. Biol. Chem., 270:30205–30212, 1995.
Cowley et al., "Estrogen receptors alpha and beta form heterodimers on DNA" J. Biol. Chem., 272(32): 19858–19862, 1997.
Danielian et al., "Identification of a conserved region required for hormone dependent transcriptional activation by steroid hormone receptors," EMBO J., 11:1025–1033, 1992.

Denton et al., "Estrogen receptor phosphorylation. Hormonal dependence and consequence on specific DNA binding," J. Biol. Chem, 267(11):7263–7268, 1992.
Hong et al., "GRIP1, a novel mouse protein that serves as a transcriptional coactivator in yeast for the hormone binding domains of steroid receptors," Proc. Natl. Acad. Sci. USA, 93:4948–4952, 1996.
Kole et al., "Protein–tyrosine phosphatase inhibition by a peptide containing the phosphotyrosyl mimetic, L–O–malonyltyrosine," Biochem. Biophys. Res. Commun., 209(3):817–822, 1995.
Onate et al., "Sequence and characterization of a coactivator for the steroid hormone receptor superfamily," Science, 270:1354–1357, 1995.
Pietras and Szego, "Partial purification and characterization of oestrogen receptors in subfractions of hepatocyte plasma membrane," Biochem. J., 191:743–760, 1980.
Pietras et al., "Steroid hormone responsive, isolated endometrial cells," Endocrinol., 96(4):946–954, 1975.
Pietras et al., "HER–2 tyrosine kinase pathway targets estrogen receptor and promotes hormone–independent growth in human breast cancer cells," Oncogene, 10(12):24352446, 1995.
Pietras et al., "Antibody to HER–2/neu receptor blocks DNA repair after cisplatin in human breast and ovarian cancer cells," Oncogene, 9(7):1829–38, 1994.
Pietras et al., "Antitumor effect of phosphoribosyl–peptides that block binding of estrogen receptor to DNA in human breast cancer cells," Eighty–Eighth Annual Meeting. Proc. Am. Assoc. Cancer Res., 38:174, abstract 1164.
Reddy et al., "Inhibition of breast cancer cell growth in vitro by a tyrosine kinase inhibitor," Cancer Res., 52(13):3636–3641, 1992.
Smith et al., "Oestrogen receptor activation in the absence of ligand," Biochem, Soc. Trans., 23:935–939, 1995.
Voegel et al., "TIF2, a 160 kDa transcriptional mediator for the ligand–dependent activation function AF–2 of nuclear receptors," EMBO J., 15(14):3667–3675, 1996.
Yao et al., The nuclear hormone receptor coactivator SRC–1 is a specific target of p300, Proc. Natl. Acad. Sci. USA, 93:10626–10631, 1996..
Ye et al., "L–O–(2–Malonyl)tyrosine: a new phosphotyrosyl mimetic for the preparation of src homology 2 domain inhibitory peptides," J. Med. Chem., 38:4270–4275, 1995.

* cited by examiner

Primary Examiner—Jeffrey Fredman
(74) Attorney, Agent, or Firm—Howrey Simon Arnold & White, LLP

(57) ABSTRACT

Disclosed are methods and compositions comprising native, site-specifically mutagenized, and synthetic peptides comprising portions of the human estrogen receptor, or estrogen receptor co-activator, and nucleic acid compositions encoding these polypeptide compositions. Also disclosed are methods for synthesizing phosphotyrosyl and malonyltyrosyl peptide derivatives and their use as antiestrogen compositions in the treatment of breast cancers, the preparation of pharmaceutical compositions, diagnostic kits, and the development of related assays for use in antitumor therapies.

40 Claims, 7 Drawing Sheets

PEPTIDE ANTIESTROGEN COMPOSITIONS AND METHODS FOR TREATING BREAST CANCER

Figure 1:
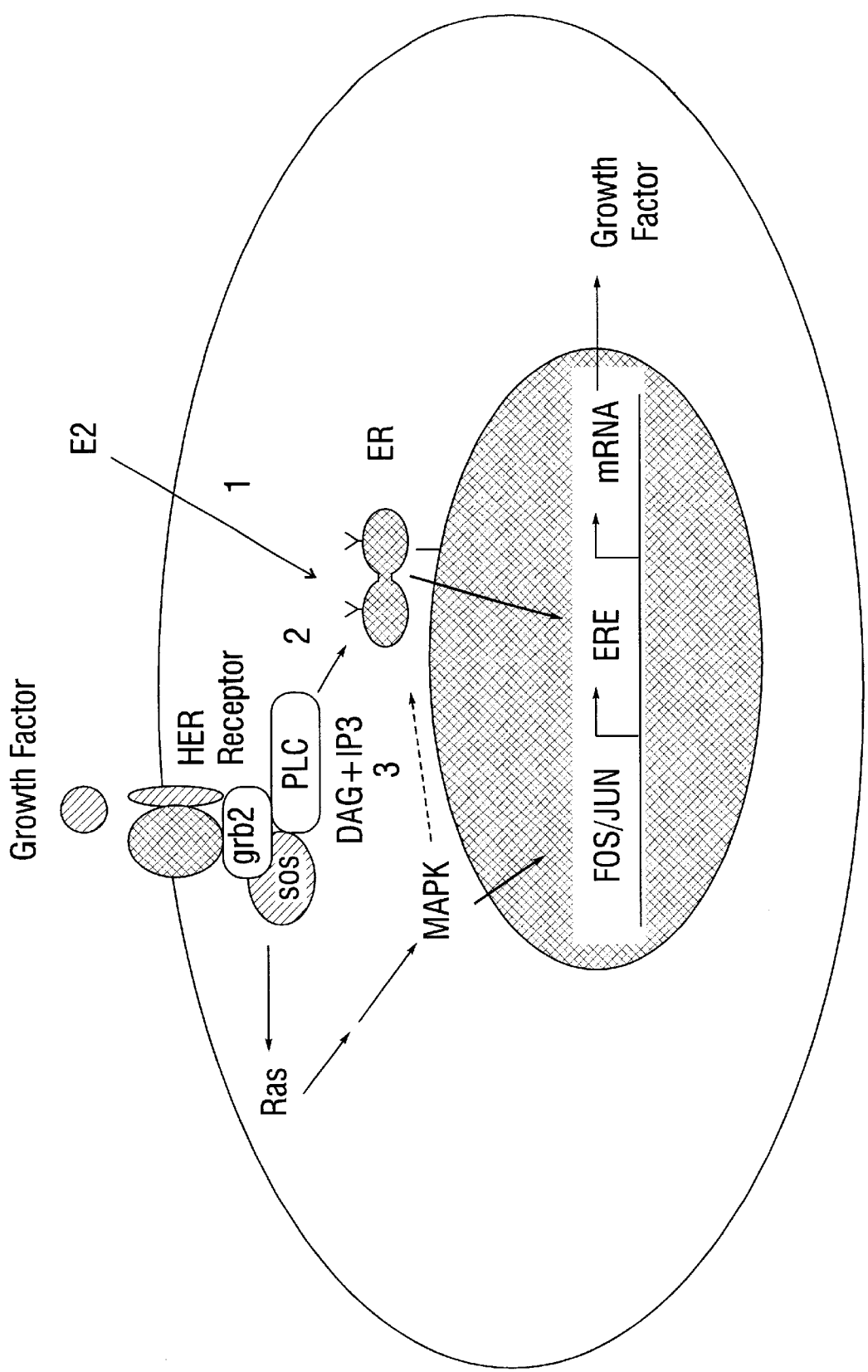

This is a continuation of co-pending application Ser. No. PCT/US98/07711 filed Apr. 14, 1998, which claims priority to U.S. Provisional Ser. No. 60/043,545, filed Apr. 14, 1997.

BACKGROUND OF THE INVENTION

The present application is a continuing application based on U.S. Provisional Application Ser. No. 60/043,545, filed Apr. 14, 1997, the entire contents of which is specifically incorporated herein by reference in its entirety.

1.1 Field of the Invention

The present invention relates generally to the field of molecular biology. More particularly, certain embodiments concern methods and compositions comprising native, site-specifically mutagenized, and synthetic peptides comprising portions of the human estrogen receptor, or estrogen receptor co-activator proteins. The invention further provides nucleic acid compositions encoding these peptide and protein compositions. Also provided are methods for synthesizing phosphotyrosyl and malonyltyrosyl peptide derivatives of these peptides and their use as antiestrogen compositions in the treatment of breast cancers, the preparation of pharmaceutical compositions, diagnostic kits, and the development of related assays for use in antitumor therapies.

1.2 Description of the Related Art

1.2.1 Breast Cancer

Breast cancer is the most common form of cancer among women, affecting about one in eight women. Approximately 185,700 new cases are diagnosed in the U.S. annually, and breast cancer is responsible for about 44,560 deaths in the U.S. per year. While predominantly observed in women, 1,400 cases of breast cancer are diagnosed annually in men, and 260 men die of breast cancer per year. Breast cancer first manifests itself as a painless lump, detectable by self-examination and clinical breast exams including mammograms. Commonly, growth initiates in the lining of the ducts or in the lobules of the breast. Current clinical treatments include mastectomy (removal of the entire breast) or lumpectomy (removal of the tumor and surrounding tissue) for localized tumors. Chemotherapy, radiotherapy, or hormone-blocking therapy may be further used to control cancerous cells. Breast cancer cells can metastasize to the lymph nodes, skin, lungs, liver, brain, or bones. Metastasis may occur early or late in the disease progression, although typically metastasis occurs once the cancerous growth reaches a size of about 20 mm. Metastasis is achieved by cells breaking away from the parental mass and entering either the bloodstream or the lymphatic system.

Genetic inheritance appears to play a role in about 5–10% of breast cancer patients. Mutations in the BRCA1, BRCA2, and p53 tumor suppressor genes have been observed to confer high risks of breast and ovarian cancers. BRCAI mutations are present at between 1 in 300 to 1 in 800 females. In the BRCA1 gene, over 200 different mutations have been discovered to date. The mutations observed are not localized to a single region, further complicating genetic analysis. Greater than 80% of the observed mutations result in a truncated form of the BRCA1 protein. Individuals with familial hereditary BRCA1 possess one normal and one mutant form of the gene, and are therefore much more likely to develop breast cancer. It is estimated that women with a hereditary BRCA1 mutation are about 76% likely to develop breast cancer by 70 years of age.

BRCA2 has been identified on chromosome 13q through linkage analysis of 15 breast cancer families that did not demonstrate BRCAI linked breast cancer. Unlike BRCA1 mutations, BRCA2 does not substantially elevate the risk of ovarian cancers. The BRCA2 gene encodes a protein of 3,418 amino acids, many of which are acidic or basic. Most mutations observed involve base deletions that alter the reading frame, and result in a premature truncation of the protein. BRCA1 and BRCA2 account for about 45% of familial inherited breast cancers each, leaving 10% for one or more additional genes. Interestingly, all male breast cancers appear to be due to mutations in the BRCA2 gene. Mutations found in breast tumor p53 genes are commonly single base pair changes which result in variants with increased cellular half lives. Altered p53 proteins have been observed in 20–25% of breast cancers.

1.2.2 Steroid Hormone Receptors

The steroid/thyroid hormone receptors are ligand-dependent transcription factors that function by binding to hormone response elements on target genes and regulating transcription (Evans, 1988). Although receptor-associated coactivators have been identified, the processes controlling steroid-specific gene transcription are poorly understood (LeDouarin et al., 1995). Most steroid/thyroid hormone receptors, including the human estrogen receptor (hER), bind to their hormone response elements as hetero- or homodimers (Kumar and Chambon, 1988; Kliewer et al., 1992), and it has been suggested that the dimerization of the steroid/thyroid hormone receptors is mediated, in part, through a leucine zipper motif in the carboxyl termini of the receptors (Forman et al., 1989; Fawell et al., 1990).

Antiestrogen therapy has had a significant impact on survival in patients with breast cancer (Jaiyesimi et al., 1995). The presence of estrogen receptor in breast tumors identifies those patients with a lower risk for disease recurrence and a better response to endocrine intervention. However, as breast cancer progresses, it usually becomes resistant to estrogens, and most patients no longer respond to treatment with tamoxifen or other antiestrogens. Results of new studies suggest that disruption of phosphotyrosine-dependent pathways may offer an alternate approach to antiestrogen treatment (Reddy et al., 1992). Modulation of the biologic activity of ER by estrogen and by tyrosine kinase signaling pathways appears to be functionally related to phosphorylation of specific conserved tyrosine residues in ER (Migliaccio et al., 1989; Castoria et al., 1993; Arnold et al., 1995; Pietras et al., 1995).

The ER is a phosphoprotein found in more than two-thirds of human breast tumors (Arnold and Notides, 1995; Weis et al., 1996; White et al., 1997). Estrogen binding to ER is thought to induce conformational changes in the receptor leading to formation of homodimers and association of the hormone-ER complexes with defmed palindromic DNA sequences termed estrogen responsive elements. EREs are usually located upstream of estrogen-responsive genes and act to regulate gene transcription and cell growth (Green and Chambon, 1988; Kato et al., 1995). Transcription is induced by two separate activation functions of the ER, an amino-terminal AF-1 region and a carboxy-terminal AF-2 region located in the hormone-binding domain of ER.

Phosphorylation of tyrosine in ER may be central to the regulation of receptor dimerization and the subsequent interaction with ERE in DNA (Castoria et al., 1993; Arnold et al., 1995; Pietras et al., 1995; Arnold and Notides, 1995; Arnold et al., 1995). New data suggest that Tyr537 may be required to maintain ER in a transcriptionally inactive state. Inactive ER is a monomer and upon estrogen-induced phosphorylation at Tyr537 and serine residues, it forms an active dimer that can bind ERE (Arnold et al., 1995; Pietras et al., 1995; Arnold and Notides, 1995; Arnold et al., 1995). Phosphotyrosine and neighboring amino acid residues on one ER monomer may provide a specific binding site for association with complementary domains on other ER monomers.

While the dimerization of most steroid hormone receptors is required for binding to DNA, accessory proteins and post-translational phosphorylation have also been implicated in DNA binding (Onate et al., 1994; Shuai et al., 1994; Hou et al., 1994). Arnold et al., (1995) demonstrated the phosphorylation of steroid/thyroid hormone receptors modulated their DNA binding affinity. The phosphorylation of the retinoic acid and progesterone receptors increases, while the phosphorylationof thyroid hormone receptor-$\alpha_2$ and nerve growth factor-I-B decreases their affinity for their respective response elements (Rochette-Egly et al., 1995; Denner et al., 1989; Katz et al., 1995; Hirataetal, 1993).

Human ER (hER), like other members of the steroid/thyroid hormone receptor superfamily, undergoes a hyperphosphorylation at serine residues following hormone binding (Denton et al., 1992). The dephosphorylation of hER with potato acid phosphatase reduces but does not eliminate the receptor's affinity for an ERE (Denton et al., 1992). Arnold et al., (1994) have shown that casein kinase II specifically phosphorylates hER at serine 167.

An estradiol-independent phosphorylation site at Tyr537 in the carboxyl-terminus of the hER has been identified by amino acid sequencing of $^{32}$P-labeled tryptic peptides of the hER (Arnold et al., 1995). Furthermore, the Src family tyrosine kinases, $p60^{c\text{-}src}$ and $p56^{lck}$, were shown to specifically phosphorylate Tyr537 on the hER, while protein-tyrosine phosphatase 1 (SHPTP1) dephosphorylated phosphotyrosine-537 (Arnold et al., 1995). Interestingly, the tyrosine kinase activity of $p60^{c\text{-}src}$ in human breast cancers has been shown to be elevated as compared with other cancers (Jacobs and Rubsaamen, 1983). The human MCF-7 mammary carcinoma cell line overexpresses $p_{60}^{c\text{-}src}$ and has been a useful paradigm for investigating estrogen-dependent processes associated with human breast cancers (Katzenellenbogen et al., 1987).

Arnold et al., (1995) demonstrated that the phosphorylation of Tyr537 is a regulatory mechanism that controls the capacity of the hER to undergo the monomer to dimer transition, and that the phosphorylation of Tyr537 is a prerequisite for the estrogen-dependent hyperphosphorylation of the serine residue(s), nuclear retention, and DNA binding of the hER.

1.2.3 Estrogens and the Proliferation of Breast Cancer

Estrogens and peptide growth factors control the proliferation of breast cells. Alterations in the receptors for these agonists occur in human cancers in nature and lead to disruption of growth regulation (Harris et al., 1992). Among growth factor receptors, the most frequently implicated in human cancers have been members of the class I receptor tyrosine kinase family (erbB). ErbB tyrosine kinase receptors are overexpressed in two-thirds of human breast cancers and are associated with malignant transformation (Slamon et al., 1987; Slamon et al., 1989a; 1989b; Harris et al., 1992; Dougall et al., 1994). These receptors include the HER-2 (erbB2) and HER-3 (erbB3) proteins which, together, constitute a high affinity functional receptor for heregulin (HRG), a ligand implicated in the autocrine/paracrine growth of breast epithelial cells (Carraway and Cantley, 1994; Sliwkowski et al., 1994). Receptors for estrogen are part of a family of steroid hormone receptors related to the viral erbA gene (Green and Chambon, 1988), and like the erbB proteins these receptors may play important pathogenic roles in breast cancer. Cross-oupling between erbB and estrogen receptor (ER) signal pathways in rodent uterine tissues has been reported (Ignar-Trowbridge et al., 1992) and is reminiscent of the cooperativity between viral erbA and erbB oncogenes in the malignant transformation of avian hematopoietic cells (Beug and Graf, 1989). Direct interaction between erbB signal pathways and ER in human breast cancer cells is the subject of several current studies (Pietras et al., 1995).

Upon estradiol binding, ER interacts with specific estrogen-response elements (ERE) in the vicinity of target genes and modulates their transcription (Green and Chambon, 1988; Smith et al., 1993). The HER-2 receptor, with intrinsic tyrosine kinase activity, is believed to promote signal transduction along specific phosphorylation cascades (Harris et al., 1992; Silvennoinenet al., 1993; Dougall et al., 1994), with recruitment of proteins that serve as a link in activation of ras, inositol triphosphate, and, possibly, other signaling pathways to the nucleus (Silvennoinen et al, 1993). Phosphorylation of ER on tyrosine and/or serine residues has been associated with functional changes in both hormone binding and nuclear localization (Arnold et al., 1994; Kuiper et al., 1994; Le Goff et al., 1994) and may be a link to kinase-mediated growth factor pathways. Blockade of estrogen-induced growth of breast tumor cells by tyrosine kinase inhibitors provides further evidence of the importance of tyrosine kinase pathways in estrogen action (Reddy et al., 1992).

Expression of either HER-2 or ER in human breast cancer provides important prognostic information (Slamon et al., 1987; Slamon et al., 1989b; Nicholson et al., 1990; Benz et al., 1993; Wright et al., 1992; Borg et al., 1994; Elledge et al., 1994). There are considerable data showing an association between HER-2 overexpression and the ER-negative phenotype (Zeillinger et al., 1989; Adnane et al., 1989), and failure of antiestrogen therapy in patients with breast cancer correlates with erb B receptor expression (Nicholson et al., 1990; Wright et al., 1992). In view of the above data, a greater understanding of the possible influence of erb B genes on the estrogen response is needed. Although ER is known to modulate HER-2 gene expression (Read et al., 1990; Russell et al., 1992), the inventor postulates that reciprocal regulation of ER by ErbB pathways may also occur, fostering hormone-independent growth in breast cancer.

1.3 DEFICIENCIES IN THE PRIOR ART

Prior to this invention, antiestrogen therapy with tamoxifen has been the standard adjuvant therapy for postmenopausal women with estrogen receptor (ER)-positive breast cancers. Tamoxifen, however, often becomes ineffective due to development of drug resistance, and tamoxifen also has some undesirable side-effects, including the genesis of endometrial and liver tumors and thromboembolic problems. More selective, targeted antiestrogen agents are needed. Phosphotyrosyl-peptides designed to block estrogen receptor association with synthetic estrogen-response elements in vitro have been described before, but there are no reports on the use of synthetic peptides modeled on ER for direct antitumor effects in human breast cancers. In addition, there are no reports on the use of malonyltyrosyl-peptides designed to block ER activity or breast tumor cell growth.

It is clear that while several approaches to antiestrogen therapies using tarnoxifen and related compounds have experienced some success, many problems remain, including those outlined herein. Thus, there exists an immediate need for improved methods and alternative compositions to provide effective antiestrogen compounds and alternatives to existing tamoxifen-based treatment of breast cancers. What is lacking in the prior art, therefore are peptides targeted to disrupt dimerization and DNA binding of ER proteins and development of a new class of antiestrogens for breast cancer therapy.

2.0 SUMMARY OF THE INVENTION

The present invention overcomes one or more of these and other drawbacks inherent in the prior art by providing novel compositions and methods for their use in the treatment of breast cancers. The invention provides novel synthetic phosphotyrosyl- and malonyltyrosyl-peptides which possess antitumor activity against human breast cancer cells. These peptides also contain leucine residues which have been implicated to play a role in receptor dimerization.

The invention offers for the first time an alternative to tamoxifen therapy by providing a new class of antiestrogen agents which are targeted directly to the estrogen receptor protein which regulates DNA transcription in human breast cancer cells. It is estimated that more than two-thirds of human breast cancers bear estrogen receptors and may respond to antiestrogen treatment.

In one embodiment, the invention concerns a composition comprising an isolated peptide of between seven and about 50 or so amino acid residues in length, wherein the peptide includes within its sequence an amino acid sequence represented by:

Pro-$AA_1$-$AA_2$-Asp-Leu-Leu-$AA_3$ wherein $AA_1$ is leucine, isoleucine, valine, or any derivative, or analog thereof; $AA_2$ is phosphotyrosine, or malonyltyrosine; and $AA_3$ is any amino acid, or a derivative or analog thereof. In illustrative embodiments, $AA_3$ is leucine or isoleucine and $AA_1$ is leucine or valine. Preferably $AA_2$ is phosphotyrosine or malonyltyrosine.

In a second embodiment, the invention concerns a composition comprising an isolated peptide of between six and about 50 or so amino acid residues in length, wherein the peptide includes within its sequence an amino acid sequence represented by:

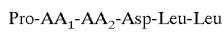

Pro-$AA_1$-$AA_2$-Asp-Leu-Leu wherein $AA_1$ is leucine, isoleucine, valine, or any derivative, or analog thereof; and $AA_2$ is phosphotyrosine, or malonyltyrosine, or a derivative or analog thereof. In illustrative embodiments, $AA_1$ is leucine or valine, and $AA_2$ is preferably phosphotyrosine or malonyltyrosine.

In a third one embodiment, the invention concerns a composition comprising an isolated peptide of between five and about 50 or so amino acid residues in length, wherein the peptide includes within its sequence an amino acid sequence represented by:

Pro-$AA_1$-$AA_2$-Asp-Leu wherein $AA_1$ is leucine, isoleucine, valine, or any derivative, or analog thereof; and $AA_2$ is phosphotyrosine, or malonyltyrosine or a derivative-or analog thereof. In illustrative embodiments, $AA_1$ is leucine or valine, and $AA_2$ is preferably phosphotyrosine or malonyltyrosine.

Preferred peptide compositions are those which either reduce or inhibit estrogen receptor activity. This reduction or inhibition of ER activity has been shown by the inventor to be accomplished by reducing or inhibiting the dimerization of estrogen receptor polypeptide monomers. Preferably the peptide composition is from between seven and about 50 or so amino acid residues in length, and may include all such peptides having a length from seven, eight, nine, or 10 amino acids up to and including those which have a length of about 55, 50, 45, 40, 35, 30, 25, 20, 15, 14, 13, or even 12 or 11 or so amino acids in length. Exemplary peptides of about 5, 6, 7, 8, 9 or 10 amino acids in length have been demonstrated to be particularly effective in reducing ER activity and ER-DNA binding both in vitro and in vivo. Such exemplary peptides are disclosed, for example, in the sequences of any of SEQ ID NO:2 through SEQ ID NO:11, SEQ ID NO:34, and SEQ ID NO:39.

The peptides of the invention may optionally further comprise one or more amino acids at the amino-terminal, or one or more amino acids at the carboxy-terninal end of the disclosed peptides, or alternatively, may further comprise one or more amino acids at both ends of the disclosed antiestrogen motif. Such amino acids may be natural amino acids, amino acid derivatives, or substituted amino acids, and may extend the overall length of the primary amino acid sequence of the peptide 5, 10, 15, 20, even 25 or so additioanl amino acids at either the amino-terminal, carboxy-terminal, or both ends of the ER dimerization-inhibitory motifs described herein. As such the overall length of the preferred peptides may be up to including 50, 60, 70, 80, 90, or even 100 or so or more amino acids, so long as the peptide comprises either the Pro-$AA_1$-$AA_2$-Asp-Leu-Leu-$AA_3$, the Pro-$AA_1$-$AA_2$-Asp-Leu-Leu, or the Pro-$AA_1$-$AA_2$-Asp-Leu motif disclosed herein.

The invention also provides peptide compositions that inhibit the binding of an SRC-1 polypeptide to an estrogen receptor polypeptide dimer. An exemplary SRC-1-inhibitory composition comprises a peptide having the amino acid sequence of SEQ ID NO:39, and methods for its use in treating cancer and in particular breast cell carcinomas. These compositions have been shown to prevent, inhibit or reduce the binding of an SRC-1 polypeptide to an estrogen receptor polypeptide dimer. The inventor has shown that these compositions comprising the peptide, either alone or conjugated to a carrier molecule, could decrease MCF-7 cell growth and reduce ER/SRC-1 Binding. Such compositions represent a class of steroid receptor coactivator peptide mimetics useful in the treatment of ER-related cancers, in killing tumor cells, and in preventing ER dimers from binding or interacting with SRC-1 polypeptides.

The peptide, polynucleotide and recombinant vector compositions of the present invention may be comprised within a lipid, nanocapsule, liposome, or lipid particle, or may be formulated in a pharmaceutical formulation as described herein. As such, the peptides may be administered to an animal which has been diagnosed with, or suspected of having, a carcinoma, tumor, or other cancer, and particularly those animals having been diagnosed with breast carcinoma.

The peptides of the invention may comprise from about 0.5% to about 99.9% or greater, by weight of the composition. As such, the peptides may comprise from about 1, 2, 3, 4, or 5% of the composition all the way up to an including about 70, 75, 80, 85, 90, or 95% or greater of the composition. Naturally, all intermediate percentages of peptide in the composition are intended to fall within the scope of the invention. For example, peptide compositions may be formulated to contain either 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 66, 67, 68, 69 or so percent of the peptide. Such pharmaceutical formulations will find particular use in preparing medicaments used in the treatment of cancers, and in particular tumors and carcinomas involving the breast. The invention also claims the use of these peptide compositions in the preparation medicaments for treating cancer, and particularly the use of the peptide compositions in the manufacture of a medicament for treating an animal. The effectiveness of particular formulations of the disclosed peptides, may be determined using an approved animal model, by assessing pharmacokinetic data, for example, using a labeled peptide. $^{125}$I-, FITC-, and $^3$H-labeled peptides may be prepared using any of the standard methods known in the art, such as those described, for example, by Kuo et al. (1992), Schoenhoff et al. (1992) or DeSantes et al. (1992).

A further aspect of the invention is a host cell comprising one or more of the peptide, polynucleotide, or recombinant vector compositions disclosed herein. The host cell may be a mammalian cell, such as a human cell, and may also be used in the preparation of anti-tumor formulations.

The invention also provides a kit as described herein, which generally comprises in a suitable container means, a therapeutically-effective amount of one or more of the disclosed antiestrogen peptide compositions in combination with a pharmaceutically acceptable excipient. The kit may naturally comprise a single or multiple container means. Preferably, the compositions of the kit are formulated is a manner which renders the compositions suitable for parenteral, intramuscular, or intravenous injection, or alternatively, oral, nasal, buccal, or topical administration. In uses such as the treatment of cancers, the kit may optionally contain one or more additional anticancer agents, or other medicaments indicated by. the physician. For example, the anticancer or antitumor agent may be a peptidomimetic, or other peptide analog which has anticancer properties, or alternatively may be a chemotherapeutic, inmunotherapeutic, radiotherapeutic, or other agent.

The peptides of the invention may also be used in the preparation of an antibody that specifically binds to an estrogen receptor polypeptide. The preparation and use of such antibodies are described herein in detail.

In another embodiment, the invention provides a method of reducing estrogen receptor activity in a cell. Such a method generally comprises providing to the cell an amount of an antiestrogen peptide derivative composition effective to reduce the estrogen receptor activity in the cell. The estrogen receptor activity may be reduced by reducing or inhibiting the dimerization of estrogen receptor polypeptides, and the association of ER with ERE in the nucleus. The cell may be in culture, or alternatively, may be comprised within an animal which has been diagnosed with, or suspected of having, a cancer such as breast carcinoma. When the cell is located within an animal, the composition may be administered to the animal in any of the medically-approved means known to those of skill in the art in the area of oncology.

The invention also provides a method for reducing estrogen receptor polypeptide dimerization in a cell. This method generally involves identifying a cell that contains a plurality of estrogen receptor polypeptides and administering to the cell an amount of an antiestrogen peptide composition effective to reduce or inhibit the dimerization of the ER receptor polypeptide monomers.

A further embodiment of the invention provides a method for treating cancer in an animal. The method generally comprises identifying an animal with a cancer such as breast cancer, and administering to the animal a therapeutically-effective amount of an antiestrogen peptide composition as disclosed herein. Such compositions may be formulated in a pharmaceutical excipient, or a liposome or other lipid carrier, and may be prepared for administration through any conventional means of peptide delivery, including intravenously, parenterally, orally, topically, or as an inhalant, aerosol or spray. Alternatively, such compositions may be coupled with homodomain peptides for translocation across biological membranes (see Derossi et al., 1994).

The invention also provides a method of killing a tumor cell. The method involves providing to a tumor cell a therapeutically-effective amount of an antiestrogen peptide composition as disclosed herein. The tumor cell is preferably comprised within an animal. An exemplary method of treating cancer in such an animal generally involves identifying an animal suspected of having cancer and administering to the animal an amount of an antiestrogen polypeptide composition sufficient to treat or reduce the spread, invasiveness, size, or extent of the cancer in the animal. The peptide formulations of the invention may also find important use in the prevention of tumor cell development.

2.1 ANTIESTROGEN PEPTIDE COMPOSITIONS

The present invention provides purified, and in preferred embodiments, substantially purified, phosophotyrosyl or malonyltyrosyl peptide derivatives which have anticancer properties. The term "purified phosophotyrosyl or malonyltyrosyl peptides" as used herein, is intended to refer to a phosophotyrosyl or malonyltyrosyl proteinaceous composition, wherein the phosophotyrosyl or malonyltyrosyl peptides are purified to any degree relative to their natually-obtainable state. A purified phosophotyrosyl or malonyltyrosyl peptide or peptide therefore also refers to a phosophotyrosyl or malonyltyrosyl peptide or protein free from the environment in which it naturally occurs.

Generally, "purified" will refer to a phosophotyrosyl or malonyltyrosyl peptide compositionthat has been subjected to fractionation to remove various non- phosophotyrosylor malonyltyrosyl peptide-derivative components, and which composition substantially retains its phosophotyrosyl or malonyltyrosyl peptide antitumor activity, as may be assessed by its inhibition or prevention of ER dimerization, or by its activity in vitro or in vivo in the reduction or treatment of cancer in an animal.

Where the term "substantially purified" is. used, this will refer to a composition in which the phosophotyrosyl or malonyltyrosyl peptide forms the major component of the composition, such as constituting about 50% of the proteins in the composition or more. In preferred embodiments, a substantially purified protein will constitute more than 60%, 70%, 80%, 900%, 95%, 99% or even 99.9% or more of the composition.

A polypeptide or protein that is "purified to homogeneity," as applied to the present invention, means that the polypeptide or protein has a level of purity where the polypeptide or protein is substantially free from other proteins and biological components. For example, a purified polypeptide will often be sufficiently free of other peptide components so that degradative sequencing may be performed successfully.

This invention is particularly concerned with phosphotyrosyl and malonyltyrosyl peptide derivatives such as isolated peptides of at least 8 or more residues in length, including those peptides up to and including about 50 or so amino acids, which comprise the amino acid sequences in any one of SEQ ID NO:2 through SEQ ID NO:11. Preferably, these peptides are ER polypeptide dimerization-inhibitory, are inhibitory of ER binding to ERE in DNA, and are active in treating tumors and breast cancers in an affected animal, such as a human. The use of small peptides in therapeutics is preferred for various reasons. These include the low cost and ease of large scale preparation, and the reliability of the product. Also their biological properties are preferable, such as the ease with which peptides can penetrate tissues, their low immunogenicity, the fact that they present a smaller target for proteases thus affording longer bioavailability and, further, it is contemplated that they will function effectively in the prevention of dimerization and DNA binding of ER and functioning as antiestrogen therapeutics.

Various methods for quantifying the degree of purification of phosophotyrosyl or malonyltyrosyl peptides will be known to those of skill in the art in light of the present disclosure. These include, for example, determining the specific activity of a fraction for preventing ER dimerization or DNA binding, or assessing the number of polypeptides within a fraction by gel electrophoresis. Assessing the number of polypeptides within a fraction by SDS/PAGE analysis will often be preferred in the context of the present invention as this is straightforward.

To purify a phosophotyrosyl or malonyltyrosyl peptide a composition comprising at least some quantity of phosophotyrosyl or malonyltyrosyl peptide will be subjected to fractionation to remove various non- phosophotyrosyl or malonyltyrosyl peptide components from the composition. Various techniques suitable for use in protein purification will be well known to those of skill in the art. These include, for example, precipitation with ammonium sulfate, PEG, antibodies and the like or by heat denaturation, followed by centrifigation; chromatography steps such as ion exchange, gel filtration, reverse phase, hydroxylapatite, lectin affinity and other affinity chromatography steps; isoelectric focusing; gel electrophoresis; and combinations of such and other techniques.

A specific example presented herein is the purification of a phosophotyrosyl or malonyltyrosyl peptide fusion protein using a specific binding partner. Such purification methods are routine in the art. As the present invention provides DNA sequences encoding specific tyrosyl peptides which may be subsequently derivatized with phosphorus or malonyl groups, inhibit dimerization of ER and inhibit DNA binding, any fusion protein purification method can now be practiced. This is currently exemplified by the generation of a phosophotyrosyl or malonyltyrosyl peptide-glutathione S-transferase fuision protein, expression in *E. coli*, and isolation to homogeneity using affinity chromatography on glutathione-agarose.

The exemplary purification method disclosed herein represents one method to prepare a substantially purified phosophotyrosyl or malonyltyrosyl peptide. This method is preferred as it results in the substantial purification of the phosophotyrosyl or malonyltyrosyl peptides in yields sufficient for further characterization and use. However, any purification method can be employed so long as the sufficient level of peptide purity is achieved.

Although preferred for use in certain embodiments, there is no general requirement that the phosophotyrosyl or malonyltyrosylpeptides always be provided in their most purified state. Indeed, it is contemplated that less substantially purified phosophotyrosyl or malonyltyrosyl peptides, which are nonetheless enriched in phosophotyrosyl or malonyltyrosyl peptides, relative to their impure state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in antibody generation.

Peptides of the present invention may also be characterized as comprising at least 8 or more residues, and include within their sequence at least one or more phosphotyrosyl or malonyltyrosyl substituted amino acid residues in the region of the peptide which contains the amino acid residue corresponding to Tyr537 in the native hER peptide sequence. In preferred embodiments, the invention is directed to a composition comprising one or more phosophotyrosyl or malonyltyrosyl peptides which are capable of preventing ER dimerization and DNA binding in vitro and in vivo.

Isolated peptides of from about 8 or about 9 residues up to and including about 100 or so amino acids which comprise any of the sequences disclosed in SEQ ID NO:2 through SEQ ID NO:11 are preferred. In addition to the peptidyl compounds described herein, the inventor also contemplates that other sterically similar compounds may be formulated to mimic the key portions of the peptide structure and that such compounds may also be used in the same manner as the peptides of the invention. This may be achieved by the techniques of modeling and chemical design known to those of skill in the art.

The present invention also encompasses therapeutic formulations, including those for parenteral administration, comprising one or more of the above-describedpeptides dispersed in a pharmacologically acceptable vehicle.

Synthetic peptides may be modified for use in therapeutics, for example, by employing one or more d-amino acids in place of 1-amino acids, by adding groups to the N- or C-termini, such as by acylation or amination, or by encapsulating the peptides within lipids, nanocapsules, lipid complexes, and/or liposomes. The peptides could also be incorporated in a biocompatible coating designed for slow-release. The preparation and use of appropriate therapeutic formulations will be known to those of skill in the art in light of the present disclosure. The present invention contemplates vaccines for use in both active and passive immunization embodiments. Immunogenic compositions, proposed to be suitable for use as a vaccine, may be prepared most readily directly from immunogenic peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

2.2 NUCLEIC ACID SEGMENTS

The present invention also concerns DNA segments, that can be isolated from virtually any source, that are free from total genomic DNA and that encode the whole or a portion of the novel peptides disclosed herein. Polynucleotides encoding the novel peptide species may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a an antiestrogen peptide or peptide refers to a DNA segment that contains an antiestrogen peptide coding sequence yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified antiestrogen peptide-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extrachromosomal DNA sequences, but also operon sequences and/or engineered gene segments that express, or may be adapted to express, proteins, polypeptides or peptides.

"Isolated substantially away from other coding sequences" means that the gene of interest, in this case, an antiestrogen polypeptide gene, forms the significant part of the coding region of the DNA segment, and that the -DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode an antiestrogen peptide species that includes within its amino acid sequence any of the amino acid sequences set forth in SEQ ID NO:2 through SEQ ID NO:12, or SEQ ID NO:34 or SEQ ID NO:39. More preferably, the DNA sequence comprises a nucleic acid sequence that encodes an antiestrogen peptide species that includes within its amino acid sequence an at least seven amino acid contiguous sequence from SEQ ID NO:2 through SEQ ID NO:12, or SEQ ID NO:34 or SEQ ID NO:39.

The term "a sequence essentially as set forth in SEQ ID NO:2 through SEQ ID NO:12, or SEQ ID NO:34 or SEQ ID NO:39," means that the sequence substantially corresponds to a portion of the sequence of SEQ ID NO:2 through SEQ ID NO:12, or SEQ ID NO:34 or SEQ ID NO:39 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of any one of SEQ ID NO:2 through SEQ ID NO:12, or SEQ ID NO:34 or SEQ ID NO:39 will be sequences that are "essentially as set forth in any one of SEQ ID NO:2 through SEQ ID NO:12, or SEQ ID NO:34 or SEQ ID NO:39."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological antiestrogen activity where peptide expression is concerned. The addition of terminal sequences particularly applies to nucleic acid sequences that may, for example, include various non-coding sequences flanking either of the 5' or 3' portions of the coding region or may include various internal sequences, ie., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fgnents may be prepared that include a short contiguous stretch encoding the whole or a portion of the peptide sequence disclosed in any of SEQ ID NO:2 through SEQ ID NO:12, or SEQ ID NO:34 or SEQ ID NO:39, or that are identical to or complementary to DNA sequences which encode any of the peptides disclosed in SEQ ID NO:2 through SEQ ID NO:12, or SEQ ID NO:34 or SEQ ID NO:39. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of the present invention, or which encode the amino acid sequence of SEQ ID NO:2 through SEQ ID NO:12, or SEQ ID NO:34 or SEQ ID NO:39. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically fluctional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded.

Alternatively, fimctionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.3 DNA SEGMENTS AS HYBRIDIZATION PROBES AND PRIMERS

In addition to their use in directing the expression of the peptides of the present invention, the nucleic acid sequences contemplated herein also have a variety of other uses. For example, they also have utility as probes or primers in nucleic acid hybridization embodiments.

The ability of such nucleic acid probes to specifically hybridize to an antiestrogen peptide-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to the DNA sequences which encode the disclosed polypeptides, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCRT technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating an antiestrogen peptide-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Of course, for some applications, for example, where one desires to prepare mutants employing a mutant primer strand hybridized to an underlying template or where one seeks to isolate an antiestrogen peptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.4 RECOMBINANT VECTORS AND POLYPEPTIDE EXPRESSION

The invention also discloses and claims compositions comprising an antiestrogen peptide. The composition may be comprised within one or more host cells which express a nucleic acid segment encoding an antiestrogen peptide, recombinant host cells which express the peptides or fusion proteins comprising the peptides, cell suspensions, extracts, inclusion bodies, or tissue cultures or culture extracts which contain the disclosed antiestrogen peptides, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing antiestrogen peptides are well-known those of skill in the art of protein isolation and purification. In certain embodiments, the antiestrogen peptides may be purified, concentrated, admixed with other reagents, or processed to a desired final form. Preferably, the composition will comprise from about 1% to about 90% by weight of the antiestrogen peptide, and more preferably from about 5% to about 50% by weight.

In a preferred embodiment, the antiestrogen peptide compositions of the invention may be prepared by a process which comprises the steps of culturing a host cell which expresses an antiestrogen peptide under conditions effective to produce such a peptide, and then obtaining the peptide from the cell. The obtaining of such an antiestrogen peptide may further include purifying, concentrating, processing, or admixing the polypeptide with one or more reagents. Preferably, the antiestrogen peptide is obtained in an amount of from between about 1% to about 90% by weight, and more preferably from about 5% to about 70% by weight, and even more preferably from about 10% to about 20% to about 30%, or even to about 40%/o or 50% by weight.

The invention also relates to a method of preparing an antiestrogen peptide composition. Such a method generally involves the steps of culturing a host cell which expresses an antiestrogen peptide under conditions effective to produce the peptide, and then obtaining the polypeptide so produced.

The recombinant plasmid vectors of the invention may be used to transform other suitable bacterial or eukaryotic cells to produce the antiestrogen polypeptides of the invention. Eukaryotic host cells including NIH3T3, COS7, and CAOV3, as well as yeast cells are contemplated to be particularly useful in the preparation of the peptide species. Likewise, prokaryotic host cells including Gram-negative cells such as E. coli, Pseudomonas spp. and related Enterobacteraceae and the like are all contemplated to be useful in the preparation of the antiestrogen peptides of the invention.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an antiestrogen peptide in its natural environment Such promoters may include promoters normally associated with other genes, and/or promoters isolated from any bacterial, viral, or eukaryotic cell. Preferred eukaryotic cells are animal cells, with mammalian cells, particularly human cells, being most preferred. Naturally, it will be important to employ a promoter that effectively directs the expression of the DNA segment in the cell type, tissue, organism, animal, or recombinant host cell chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

2.5 THERAPEUTIC AND DIAGNOSTIC KITS

Therapeutic kits of the present invention are kits comprising a phosophotyrosyl or malonyltyrosyl protein, peptide, inhibitor, gene, vector or other phosophotyrosyl or malonyltyrosyl binding protein effector. Such kits will generally contain, in suitable container means, a pharmaceutically acceptable formulation of a phosophotyrosyl or malonyltyrosyl protein, peptide, domain, inhibitor, or a gene or vector expressing any of the foregoing in a pharmaceutically acceptable formulation, optionally comprising other anti-cancer agents. The kit may have a single container means, or it may have distinct container means for each compound.

When the components of the kit are provided in one or more liquid solutions, the liquid solution is an aqueous solution, with a sterile aqueous solution being particularly preferred. The phosophotyrosyl or malonyltyrosyl protein compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit However, the components of the kit may be provided as dried powder(s). When reagents or components are provided as a dry powder, the powder can be reconstituted by the addition of a suitable solvent It is envisioned that the solvent may also be provided in another container means.

The container means will generally include at least one vial, test tube, flask, bottle, syringe or other container means, into which the phosophotyrosyl or malonyltyrosyl protein or gene or inhibitory formulation are placed, preferably, suitably allocated. Where a second anti-cancer therapeutic is provided, the kit will also generally contain a second vial or other container into which this agent may be placed. The kits may also comprise a second/third container means for containing a sterile, pharmaceutically acceptable buffer or other diluent The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate phosophotyrosyl or malonyltyrosyl protein or gene composition within the body of an animal. Such an instrument may be a syringe, pipette, forceps, or any such medically approved delivery vehicle, such as a transcatheter arterial embolization or needle therapy device as disclosed in U.S. Pat. No. 4,536,387, specifically incorporated herein by reference in its entirety.

2.6 AFFINITY CHROMATOGRAPHY

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains one or more peptide epitopes derived from the proteins disclosed herein, covalently-coupled to a Sepharose CL6B or CL4B. This matrix binds the antibodies of the present invention directly and allows their separation by elution with an appropriate gradient such as salt, GuHCl, pH, or urea Another preferred embodiment of the present invention is an affinity chromatography method for the purification of the disclosed proteins and peptide epitopes from solution. The matrix binds the amino acid compositions of the present invention directly, and allows their separation by elution with a suitable buffer as described above.

2.7 METHODS OF NUCLEIC ACID DELIVERY AND DNA TRANSFECTION

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells have been described:

(1) chemical methods (Graham and VanDerEb, 1973);
(2) physical methods such as microinjection (Capecchi, 1980), electroporation (Wong and Neumann, 1982; Fromm et al., 1985) and the gene gun (Yang et al., 1990);
(3) viral vectors (Clapp, 1993; Eglitis et al., 1988; Eglitis and Anderson, 1988); and
(4) receptor-mediated mechanisms (Curiel et al., 1991; Wagner et al., 1992).

2.8 LIPOSOMES AND NANOCAPSuLES

In certain embodiments, the inventor contemplates the use of liposomes and/or nanocapsules for the introduction of peptide compositions into host cells. Such formulations may be preferred for the introduction of pharmaceutically-acceptable formulations of the polypeptides, pharmaceuticals, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

In one instance, the disclosed composition may be entrapped in a liposome. Liposomes are vesicular structures characteried by a phospholipid bilayer membrane and an inner aqueous medium. Multilamellar liposomes have multiple lipid layers separated by aqueous medium The term "liposome" is intended to mean a composition arising spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyano-acrylate nanoparticles that meet these requirements are contemplated for use in the present invention, and such particles may be easily made, as described (Couvreur et al., 1977; 1988). Methods of preparing polyalkyl-cyano-acrylate nanoparticles containing biologically active substances and their use are described in U.S. Pat. No. 4,329,332, U.S. Pat. No. 4,489,055, and U.S. Pat. No. 4,913,908 (each specifically incorporated herein by reference in its entirety).

Pharmaceutical compositions containing nanocapsules for the oral delivery of active agents are described in U.S. Pat. No. 5,500,224 and U.S. Pat. No. 5,620,708 (each specifically incorporated herein by reference in its entirety). U.S. Pat. No. 5,500,224 describes a pharmaceutical composition in the form of a colloidal suspension of nanocapsules comprising an oily phase consisting essentially of an oil containing dissolved therein a surfactant and suspended therein a plurality of nanocapsules having a diameter of less than 500 nanometers. U.S. Pat. No. 5,620,708 describes compositions and methods for the oral administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitivedrugs, such as polypeptides, in the intestines can be avoided while absorption of proteins and polypeptides form the intestinal tract is inced.

U.S. Pat. No. 5,641,515 and U.S. Pat. No. 5,698,515 (each specifically incorporated herein by reference in its entirety) describe the use of nanocapsules for the oral administration of a polypeptide, specifically, insulin and are incorporated herein by reference. U.S. Pat. No. 5,698,515 described insulin containing nanocapsules intended for oral administration of insulin which comprises a hydrophilic polymer modified with an inhibitor of proteolytic enzyme, insulin and water, wherein the inhibitor of proteolytic enzymes is ovomucoid isolated from duck or turkey egg whites. U.S. Pat. No. 5,556,617 describes the use of nanoparticles as pharmaceutical treatment of the upper epidermal layers by topical application on the skin.

Poly(alkyl cyanoacrylate) nanocapsules have been used as biodegradable polymeric drug carriers for subcutaneous and peroral delivery of octreotide, a long-acting somatostatin analog. The nanocapsules, prepared by interfacial emulsion polymerization of isobutyl cyanoacrylate, were 216 nm in diameter and incorporated 60% of octreotide. Nanocapsules were administered subcutaneously and the octreotide-loaded nanocapsules (20 mg/kg) suppressed the insulinemia peak induced by intravenous glucose overload and depressed insulin secretion over 48 h. When administered perorally to estrogen-treatedrats, octreotide loaded nanocapsules(200 and 100 mg/kg) significantly improved the reduction of prolactin secretion and slightly increased plasma octreotide levels (Damge et al., 1997).

The negative surface charge of nanocapsules makes them particularly susceptible to lysozyme (LZM), a positively-charged enzyme that is highly concentrated in mucosas. This interaction causes destabilization of the nanocapsule by LZM; however, it was observed that the destabilizing effects caused by the adsorption of LZM onto the nanocapsules can be prevented by previous adsorption of the cationic poly (amino acid) poly-L-lysine (Calvo et al., 1997).

Calvo et al., 1996 describe the use of poly-epsilon-caprolactone (PECL) microparticles for the ocular bioavailability of drugs. Their study showed that PECL nanoparticles and nanocapsules as well as submicron emulsions are shown to be novel comeal drug carriers, and represent a useful approach for increasing the ocular bioavailability of drugs.

An excellent review of nanoparticles and nanocapsular carriers is provided by Arshady 1996. Arshady notes that one of the major obstacles to the targeted delivery of colloidal carriers, or nanocapsules, is the body's own defense mechanism in capturing foreign particles by the reticuloendothelial system (RES). This means that following intravenous administration, practically all nanometer size particles are captured by the RES (mainly the liver). The review describes recent initiatives on the design of macromolecular homing devices which seem to disguise nanoparticles from the RES and, hence, are of potential interest to the targeted delivery of nanocapsular carriers. The idea is based on a graft copolymer model embodying a link site for attachment to the carrier, a floating pad for maintaining the particles afloat in the blood stream, an affinity ligand for site-specific delivery and a structural tune for balancing the overall structure of the homing device.

Yu and Chang, 1996 describe the use of nanocapsules containing hemoglobin as potential blood substitutes. They use different polymers including polylactic acid and polyisobutyl-cyanoacrylate and modify the surface of the nanocapsules with polyethylene glycol (PEG) or with PEG 2000 PE. The surface modified nanocapsules containing hemoglobin survive longer in the circulation.

U.S. Pat. No. 5,451,410describesthe use of modified amino acid for the encapsulation of active agents. Modified amino acids and methods for the preparation and used as oral delivery systems for pharmaceutical agents are described. The modified amino acids are preparable by reacting single amino acids or mixtures of two or more kinds of amino acids with an amino modifying agent such as benzene sulfonyl chloride, benzoyl chloride, and hippuryl chloride. The modified amino acids form encapsulating microspheres in the presence of the active agent under sphere-forming conditions. Alternatively, the modified amino acids may be used as a carrier by simply mixing the amino acids with the active agent. The modified amino acids are particularly useful in delivering peptides, e.g., insulin or calmodulin, or other agents which are sensitive to the denaturing conditions of the gastrointestinal tract.

2.9 METHODS FOR PRODUCING AN IMMUNE RESPONSE

Also disclosed is a method of generating an immune response in an animal. The method generally involves administering to an animal a pharmaceutical composition comprising an immunologically effective amount of a peptide composition disclosed herein. Preferred peptide compositions include the peptides disclosed in SEQ ID NO:2 through SEQ ID NO:11.

The invention also encompasses peptide antigen compositions together with pharmaceutically-acceptableexcipients, carriers, diluents, adjuvants, and other components, such as additional peptides, antigens, or outer membrane preparations, as may be employed in the formulation of particular vaccines.

The nucleic acid sequences of the present invention are useful to generate pure recombinant proteins and peptides for administration to a host. Such administration is useful in generating an immune response in the animal, such as a vaccine to produce therapeutic antibodies.

Using the peptide antigens described herein, the present invention also provides methods of generating an immune response, which methods generally comprise administering to an animal, a pharmaceutically-acceptable composition comprising an immunologically effective amount of a peptide composition. Preferred animals include mammals, and particularly humans. Other preferred animals include murines, bovines, equines, porcines, canines, and felines. The composition may include partially or significantly purified peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 10 and about 50, or even between about 50 and about 100 amino acids in length will often be preferred. The antigenic proteins or peptides may also be combined with other agents, such as other peptide or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility iin both the production of useful bioreagents, e.g., CTLs and, more particularly, reactive antibodies, for use in diagnostic embodiments, and will also have utility in various prophylactic or therapeutic embodiments.

Further means contemplated by the inventor for generating an immune response in an animal includes administering to the animal, or human subject, a pharmaceutically-acceptable composition comprising an immunologically effective amount of a nucleic acid composition encoding one or more of the epitopes disclosed herein, or an immunologically effective amount of an attenuated live organism that includes and expresses such a nucleic acid composition. The "immunologically effective amounts" are those amounts capable of stimulating a B cell and/or T cell response.

The identification or design of suitable epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences, for example, Chou and Fasman (1974a,b; 1978a,b; 1979); Jameson and Wolf (1988); Wolf et al., (1988); and Kyte and Doolittle (1982) address this subject. The amino acid sequence of these "epitopic core sequences" may then be readily incorporated into peptides, either through the application of peptide synthesis or recombinant technology.

2.10 METHODS FOR PREPARING ANTIBODY COMPOSOSITIONS

In another aspect, the present invention contemplates an antibody that is immunoreactive with a polypeptide of the invention. As stated above, one of the uses for disclosed peptides according to the present invention is to generate antibodies. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques.

The present invention further provides anti- malonyltyrosyl peptide or phosphotyrosyl peptide antibodies, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins". In the context of the present invention, immunotoxins are generally less preferred.

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging". Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^3$H, $^{14}$C, $^{32}$P, $^{35}$S, $^{36}$Cl, $^5$CR, $^{57}$Co, $^{58}$Co, $^{59}$Fe, $^{67}$Cu, $^{67}$Ga, $^{75}$Se, $^{90}$Yt, $^{99m}$Tc, $^{111}$In, $^{123}$I, $^{125}$I, $^{131}$I, $^{152}$Eu, $^{186}$Re, $^{188}$Re, and $^{211}$As. $^{125}$I is often being preferred for use in certain embodiments, and $^{99m}$Tc and $^{111}$In are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with $^{99m}$Tc by ligand exchange process, for example, by reducing pertechnate with stannous solution, chelating the reduced technetium onto a Sephadex column and applying the antibody to this column or by direct labeling techniques, e.g. by incubating pertechnate, a reducing agent such as SnCl$_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetraceticacid (EDTA).

Fluorescent labels include rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the disclosed proteins and peptides may be prepared using conventional immunization techniques, as will be generally known to those of skill in the art A composition containing antigenic epitopes of particular proteins can be used to immunize one or more experimental animals, such as a rabbit or mouse, which will then proceed to produce specific antibodies against that particular peptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i. e., B-cells of different lineage. mAbs, by contrast, are defmed as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, ie., the percentage of clone reacting with the same molecular determinant, is at least 80%. Even higher clonality—90%, 95% or greater—is contemplated.

To obtain mAbs, one would also initially immunize an experimental animal, often preferably a mouse, with a protein or peptide-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting mAbs against the particular protein or peptide. Hybridomas which produce mAbs to the selected antigens are identified using standard techniques, such as ELISA and Western blot methods. Hybridoma clones can then be cultured in liquid media and the culture supernatants purified to provide the protein or peptide-specific mAbs.

It is proposed that the mAbs of the present invention will also find useful application in immunochemical procedures, such as ELISA and Western blot methods, as well as other procedures such as immunoprecipitation, immunocytological methods, etc. which may utilize antibodies specific to one or more of the disclosed peptides. In particular, antibodies may be used in immunoabsorbent protocols to purify native or recombinant proteins or peptide species or synthetic or natural variants thereof The methods for generating mAbs generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine. mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (Bells), are selected for use in the mAb generating protocol.

These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5\times10^7$ to about $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler et al., 1975; 1976), and those using polyethylene glycol (PEG), such as 37% (vol/vol.) PEG, by Gefter et al. (1977). The use of electrically induced fusion methods is also appropriate (Goding, 1986).

Fusion procedures usually produce viable hybrids at low frequencies, about $1\times10^{-6}$ to about $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in micrometer plates, followed by testing the individual clonal supernatants (after about two to three weeks) for the desired reactivity. The assay should be sensitive, simple and rapid, such as radioimunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific mAb produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.11 IMMUNOASSAYS

As noted, it is proposed that native and synthetically-derived peptides and peptide epitopes of the invention will find utility as immunogens, e.g., in connection with vaccine development, or as antigens in immmunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of the disclosed proteins and peptides is not limited to such assays, and that other useful embodiments include RIAs and other non-enzyme linked antibody binding assays and procedures.

In preferred ELISA assays, proteins or peptides incorporating phosphotyrosyl or malonyltyrosyl peptide antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween™).

After incubation with the second enzyme-tagged antibody, and subsequent to washing to remove unbound material, the amount of label is quantified by incubation with a chromogenic substrate such as urea and bromocresol purple or 2,2'-azino-di-3-ethyl-benzhiazoline)-6sulfonic acid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences of the present invention are immobilized onto a selected surface, preferably a surface exhibiting a protein affinty such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

2.12 IMMUNOPRECIPITATION

The antibodies of the present invention are particularly useful for the isolation of antigens by immunoprecipitation. Immunoprecipitation involves the separation of the target antigen component from a complex mixture, and is used to discriminate or isolate minute amounts of protein. Alternatively, the antibodies of the present invention are useful for the close juxtaposition of two antigens. This is particularly useful for increasing the localized concentration of antigens, e.g, enzyme-substrate pairs.

2.13 WESTERN BLOTS

The compositions of the present invention will find great use in immunoblot or western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologicaly-based detection methods in conjunction with Western blotting (including enzymatically-, radiolabel-, or fluorescently-tagged secondary antibodies against the toxin moiety) are considered to be of particular use in this regard.

2.14 ANTIESTROGEN PEPTIDE SCREENING AND IMMUNIODETECTION KITS

The present invention also provides compositions, methods and kits for screening samples suspected of containing an antiestrogen peptide or a nucleic acid segment encoding such an antiestrogen peptide. Alternatively, the invention provides compositions, methods and kits for screening samples suspected of containing antiestrogen peptides or genes encoding antiestrogen peptides which are functionally equivalent to, or substantially homologous to, the antiestrogen peptides disclosed herein. Such screening may be performed on samples such as transformed host cells, clinical or laboratory samples suspected of containing or producing such a polypeptide or nucleic acid segment. A kit can contain a nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the antiestrogen peptides of the present invention may be employed to detect antibodies having reactivity therewith, or, alternatively, antibodies prepared in accordance with the present invention, may be employed to detect antiestrogen peptides or antiestrogen peptide-related peptides. In general, these methods will include first obtaining a sample suspected of containing- such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a an antiestrogen peptide or peptide or a an antiestrogen peptide-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of an antiestrogen peptides or related peptides and/or antibodies in a sample. Samples may include cells, cell supernatants, cell suspensions, cell extracts, enzyme fractions, protein extracts, or other cell-free compositions suspected of containing an antiestrogen peptides or peptides. Generally speaking, kits in accordance with the present invention will include a suitable an antiestrogen peptide, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.15 PHARMACEUTICAL COMPOSITIONS

The peptide compositions of the invention may be administered in combination with one or more chemotherapeutic agents such as CMF (cyclophosphamide, methotrexate, fluorouracil), FAC (fluorouracil, adriamycin, cyclophosphamide), tamoxifen, or other antitumor agents. As will be understood by those of ordinary skill in the art, the appropriate doses of the antiestrogen peptides will be generally around those already employed in clinical therapies wherein such peptides are administered alone or in combination with other antitumor or anticancer agents, including approved chemotherapeutic agents known to those of skill in the art. By way of example only, agents such as cisplatin, and other DNA alkylating may be used. Cisplatin has been widely used to treat cancer, with efficacious doses used in clinical applications of 20 $mg/m^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 $mg/m^2$ at 21 day intervals for adriamycin, to 35–50 $mg/m^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly usefull for targeting to neoplastic cells. Although quite toxic, 5-FU, is applicable in a wide range of carriers, including topical, however intravenous administrationwith doses ranging from 3 to 15 mg/kg/day being commonly used.

Exemplary chemotherapeutic agents that are useful in connection with combined therapy are listed in Table 1. Each of the agents listed therein are exemplary and by no means limiting. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE 1

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
| --- | --- | --- | --- |
| Alkylating Agents | Nitrogen Mustards | Mechlorethamine ($HN_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's |

TABLE 1-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | Ethylenimenes and Methylmelamines | Hexamethylmelamine | disease, non-Hodgkin's lymphomas Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidaz olecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorode-oxyuridine; FUdR) | |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide | Testis, small-cell lung and other lung, breast, Hodgkin's disease, non-Hodgkin's lymphomas, acute granulocytic leukemia, Kaposi's sarcoma |
| | | Tertiposide | |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) | Testis, ovary, bladder, head and neck, lung, thyroid, cervix, endometrium, |
| | | Carboplatin | |

TABLE 1-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | | | neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

The peptide compositions may be administered in combination with a variety of pharmaceutical excipients, including stabilizing agents, carriers and/or encapsulation formulations as described herein. In particular, the inventor contemplates the use of liposomal delivery systems employing one or more of the instant peptides coupled with internalization sequences such as those from antennapedia, or by other peptide delivery systems as known to those of skill in the art (Saudek, 1997).

Aqueous compositions of the present invention comprise an effective amount of the antiestrogen peptide, such as a phosphotyrosyl or malonyltyrosyl protein, peptide, epitopic core region, inhibitor, or such like, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of a phosphotyrosyl or malonyltyrosyl peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art Supplementary active ingredients can also be incorporated into the therapeutic compositions of the present invention. For example, the viral binding peptides may also be combined with peptides including cytotoxic T cell- or T helper cell-inducing epitopes to create peptide cocktails for immunization and treatment. Alternatively, compounds with other known or proposed anti-viral activities may also be added if desired.

The preparation of pharmaceutical or pharmacological compositions containing viral binding peptide or peptides, including dextrorotatory peptides, as an active ingredients will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active peptide, peptides or agentsto a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of a phosphotyrosyl or malonyltyrosyl protein, peptide or peptides sufficient to significantly inhibit or prevent dimerization of ER-ERE and ultimately lessen, reduce, eliminate, or treat a breast cancer cell in the host animal (mammal).

In this context, the quantity of peptide(s) and volume of composition to be administered depends on the host animal to be treated. Precise amounts of active peptide required to be administered depend on the judgment of the practitioner and are peculiar to each individual. However, the peptides are shown to be particularly effective in vitro with one nanogram/ml giving 40% inhibition. Suitable dosage ranges for use in humans are therefore contemplated to be those which result in similar local concentrations of peptides. Doses in the order of about 1 $\mu$g/kg/day to about 500 $\mu$g/kg/day, preferably about 10 $\mu$g/kg/day to about 200 $\mu$g/kg/day, and more preferably about 50 $\mu$g/kg/day of active ingredient peptide per individual are contemplated.

A minimal volume of a composition required to disperse the phosphotyrosyl or malonyltyrosyl peptide or peptides is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, "Remiington's Pharmaceutical Sciences" 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

A phosophotyrosyl or malonyltyrosyl peptide, peptidomimetic, agonist or antagonist of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

In terms of using peptide therapeutics as active ingredients, the technology of U. S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small tumor ae Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The active phosophotyrosyl or malonyltyrosyl peptides or agents may be formulated within a therapeutic mixture to comprise about 0.0001 to 1.0 mg, or about 0.001 to 0.1 mg, or about 0.1 to 1.0 or even about 10 mg per dose or so. Multiple doses can also be administered In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

Additional formulations which are suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

It will naturally be understood that suppositories, for example, will not generally be contemplated for use in treating breast cancer. However, in the event that the proteins, peptides or other agents of the invention, or those identified by the screening methods of the present invention, are confirmed as being useful in connection with other forms of cancer, then other routes of administration and pharmaceutical compositions will be more relevant. As such, suppositories may be used in connection with colon cancer, inhalants with lung cancer and such like.

2.16 EPITOPIC CORE SEQUENCES

The present invention is also directed to protein or peptide compositions, free from total cells and other peptides, which comprise a purified protein or peptide which incorporates an epitope that is immunologically cross-reactive with one or more of the antibodies of the present invention.

As used herein, the term "incorporating an epitope(s) that is immunologically cross-reactive with one or more antibodies" is intended to refer to a peptide or protein antigen which includes a primary, secondary or tertiary structure similar to an epitope located within one of the novel polypeptides disclosed herein. The level of similarity will generally be to such a degree that monoclonal or polyclonal antibodies directed against the particular polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of epitopes such as those derived from HER-2/neu and HER-2/neu-like gene products and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to the peptide sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on the protein or peptide epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar™ software, DNAStar, Inc., Madison, Wis.) may also be useful in designing synthetic peptides and peptide analogs in accordance with the present disclosure.

The peptides provided by this invention are ideal targets for use as vaccines or immunoreagents for the treatment of various ER-related cancers, and in particular, those involving breast cancer. In this regard, particular advantages may be realized through the preparation of synthetic peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohisto chemical assays, ELISAS, RIAs, Western or dot blotting and the like. In any of the competitive assays, one of the binding components, generally the known element, such as the disclosed peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between a protein or peptide and any test antigen, one would first label the protein or peptide with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to an antibody of the present invention. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody, for example, will be able to effectively compete for binding to and thus will significantly reduce protein or peptide binding, as evidenced by a reduction in the amount of label detected.

The reactivity of the labeled antigen, e.g., one of the disclosed peptide compositions, in the absence of any test antigen would be the control high value. The control low value would be obtained by incubating the labeled antigen with an excess of unlabeled antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventor also contemplates that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. it will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.17 PEPTIDE MIMETIC COMPOSITIONS

In addition to the peptidyl compounds described herein, the inventor also contemplates that other sterically similar compounds may be formulated to mimic the key portions of the peptide structure or to interact specifically with ER. Such compounds, which may be termed peptidomimetics, may be used in the same manner as the peptides of the invention and hence are also functional equivalents.

Certain mimetics that mimic elements of protein secondary structure are described in Kahn el al. (1988); Kahn et al. (1991); Chen et al. (1992); Sato et al. (1992). The underlying rationale behind the use of peptide mimetics is that the peptide backbone of proteins exists chiefly to orient amino acid side chains in such a way as to facilitate molecular interactions, such as those of antibody and antigen. A peptide mimetic is thus designed to permit molecular interactions similar to the natural molecule (Sikorski et al. 1977; Kiso, 1996).

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains (Eichler et aL 1995; Kempf, 1994; Smith et al. 1997).

2.18 MUTAGENESIS METHODS

The means for mutagenizing nucleic acid segments are well-known to those of skill in the art. Modifications to such promoter regions may be made by random, or site-specific mutagenesis procedures. The promoter region may be modified by altering its structure through the addition or deletion of one or more nucleotides from the sequence which encodes the corresponding unmodified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

The technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al (1990) and Upender et al., (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. No. 4,237,224, specifically incorporated herein by reference in its entirety.

A number of template dependent processes are available to amplify the target sequences of interest present in a sample. One of the best known amplification methods is the polymerase chain reaction (PCR™which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, e.g., nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Still other amplification methods described in Great Britain Pat Appl. No. 2,202,328, and in PCT Intl. Pat. Appl. Publ. No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA[99]"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

2.19 BIOLOGICAL FUNCTIONAL EQUIVALENTS

In addition to the particular antiestrogen peptide sequences disclosed herein, the inventor contemplates the preparation of peptide mutants which have additional amino acid residues modified either within or outside of the consensus motif surrounding the central phosphorylated tyrosine residue. Such mutants may be more active and/or more stable for in vitro and in vivo formulations. The substitution of malonyltyrosine for phsophotyrosine as described in the examples conferred a more stable peptide, and one that appeared to be more resistant to degradation.

Modification and changes may be made in the structure of the peptides of the present invention and DNA segments which encode them and still obtain a functional molecule that encodes a peptide with desirable characteristics. The following is a discussion based upon changing the amino acids of a peptide to create an equivalent, or even an improved, second-generation molecule. The amino acid changes may be achieved by changing the codons of the DNA sequence, according to the codon table listed in Table 2:

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventor that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine(+4.5); valine (+4.2); leucine (+3.8); phenylalanine (+2.8); cysteine/cystine (+2.5); methionine (+1.9); alanine (+1.8); glycine (−0.4); threonine (−0.7); serine 0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine ((−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Postulated cellular mechanism of action of estrogen (E2) and growth factors. Estrogen binding to ER monomer normally promotes formation of a receptor dimer which is thereby enabled to bind nuclear estrogen-response elements (ERE) and initiate gene transcription (path 1). ER interaction with ERE may be due to post-translational phosphorylation at specific tyrosine (Y) and serine (I) residues of ER ER may be a substrate for direct phosphorylation by growth factor-activated tyrosine kinase receptors (path 2) and indirect phosphorylation via 2nd-messengers including serine/threoninekinases such as phospholipase C, PLC, or MAP kinase, MAPK (path 3).

Figure 2:
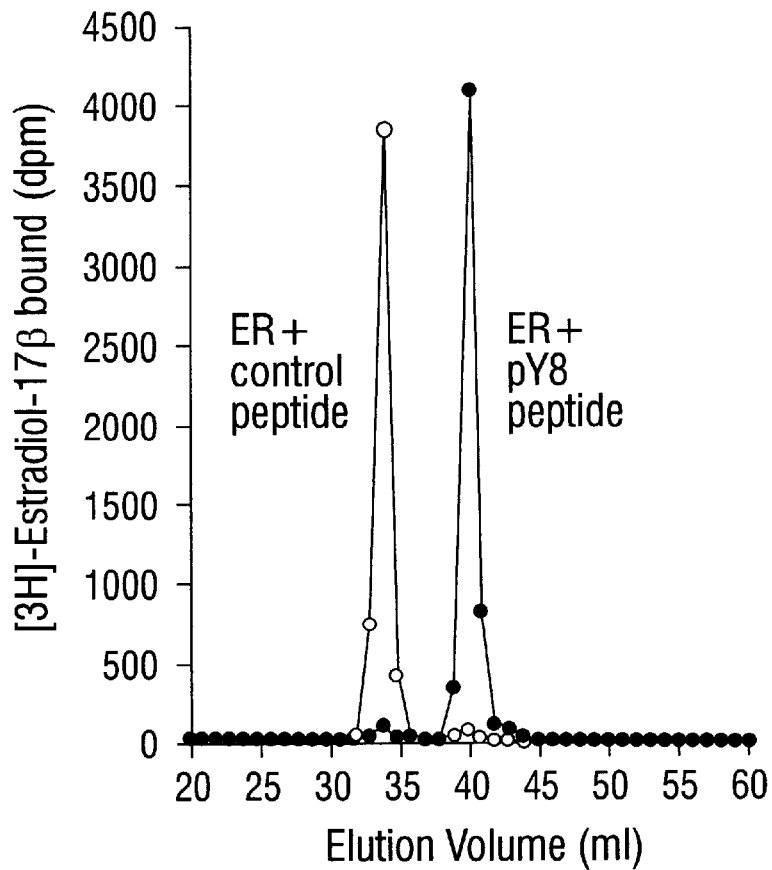

FIG. 2. Gel chromatography of purified estrogen receptor and the effect of phosphotyrosyl-peptides. Purified recombinant ER was incubated with 10 nM [$^3$H]-estradiol and either 25 $\mu$M pY-peptide (black circles) or 25 $\mu$M control Y peptide (open circles), followed by gel chromatography (Arnold and Notides, 1995; Oboumn et al., 1993). Total column volume was 64 ml, and void volume was 21 ml. Only the elution volume from 20 ml to 60 ml is shown. Albumin (67 kDa) eluted at 40 ml, and aldolase (158 kDa) eluted at 32 ml. Studies with pY-and control-peptides were performed independently three times but are displayed together here to assist in direct comparison of the results. ER incubated with [$^3$H]-estradiol and without peptides eluted at a peak volume equal to that of the control-peptidegroup.

Figure 3:
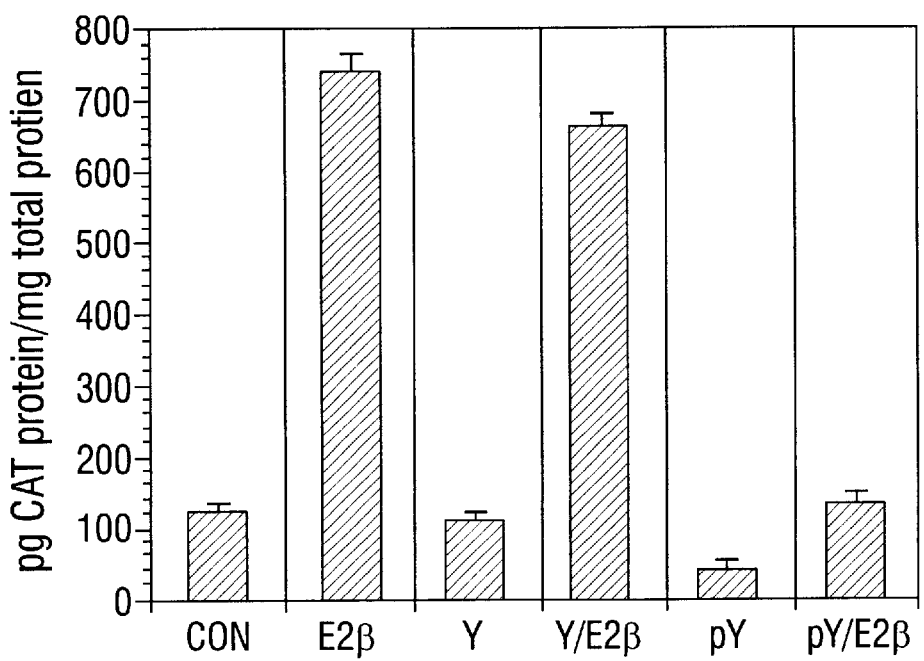

FIG. 3. Phosphotyrosyl peptide-pY elicits suppression of the activation of ERE-CAT reporter gene after transient transfection in MCF-7 breast cancer cells. A reporter plasmid with palindromic ERE was used, derived from vitellogenin A2 promoter, and CAT gene driven by a partial promoter sequence of thymidine kinase (Ernst et al., 1991; Pietras et al., 1995). Substituting the basic reporter plasmid pBLCAT2 for pERE-BLCAT provides an additional control. MCF-7 cells were used to establish transient transfection assays that allow assay of ERE-dependent induction of CAT activity. CAT protein was assessed by established methods (Pietras et al., 1995). Activity of control (CON) and 1 nM estradiol-17$\beta$ (E$_6\beta$) for 24 h was suggested using there transfected cells with or without ERE. E$_2\beta$ elicited no change in the basal activity of the CON-CAT gene construct in MCF-7 cells or in the activity of ERE-CAT gene transiently transfected in HBL-100 cells which have no detectable ER. Effects of preincubation with 100 $\mu$M Y-peptide (Y), 100 $\mu$M Y-peptide+1 nM E$_2\beta$ (Y/E$_2\beta$), 100 $\mu$M pY-peptide (pY), or 100 $\mu$M pY-peptide+1 nM E$_2\beta$ (pY/E$_2\beta$) on MCF-7 cells is shown. Peptides were delivered by use of cationic liposomes using methods described in detail before (Pietras, 1978).

Figure 4:
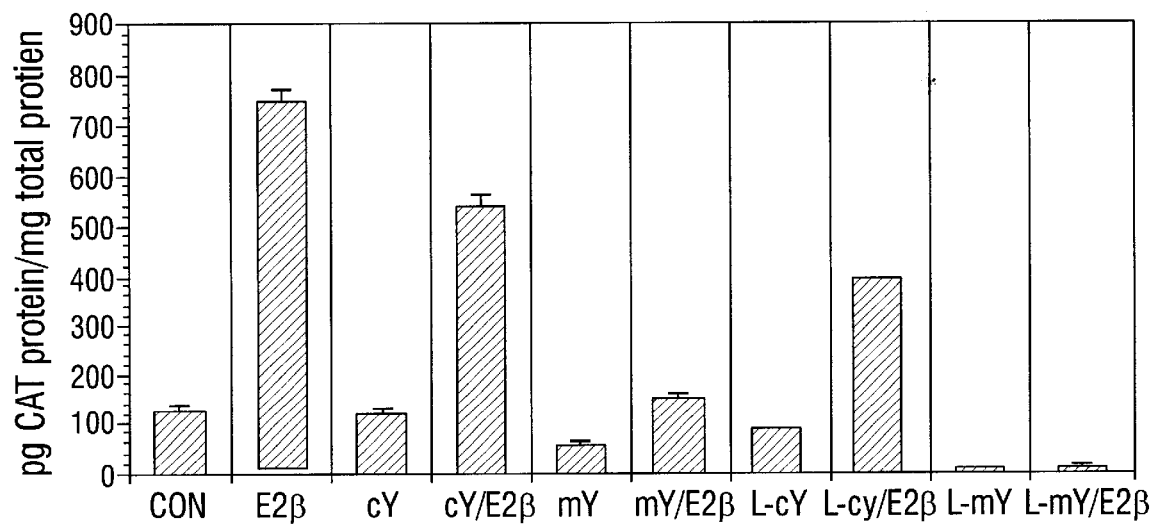

FIG. 4. Malonyltyrosyl peptide-mY elicits suppression of the activation of ERE-CAT reporter gene after transient transfection in MCF-7 breast cancer cells. A reporter plasmid with palindromic ERE was used, derived from vitellogenin A2 promoter, and CAT gene driven by a partial promoter sequence of thymidine kinase Ernst et al., 1991; Pietras et al., 1995). Substituting the basic reporter plasmid pBLCAT2 for pERE-BLCAT provides an additional control. MCF-7 cells were used to establish transient transfection assays that allow assay of ERE-dependent induction of CAT activity. CAT protein was assessed by established methods (Pietras et al., 1995). Activity of control (CON) and 1 nM estradiol-17β (E$_2$β) for 24 h was assessed using these transfected cells with or without ERE. E$_2$β elicited no change in the basal activity of the CO-CAT gene construct in MCF-7 cells or in the activity of ERE-CAT gene transiently transfected in HBL-100 cells which have no detectable ER. Effects of preincubation with 100 μM control-Y-peptide (cY); 100 μM cY+1 nM E$_2$β (cY/E$_2$β); malonyltyrosine peptide alone (mY); and malonyltyrosine peptide+E$_2$β (mY/E$_2$β) on MCF-7 cells is shown. Peptides were also delivered by use of liposomes using methods described in detail before (Pietras, 1978), with results showing liposome delivery of control Y-construct (L-cY), control+1 nM E$_2$β (L-cY/E$_2$β), malonyltyrosyl-peptide (L-mY), or malonyltyrosyl-peptide+1 nM E$_2$β(L-mY/E$_2$β).

Figure 5A:
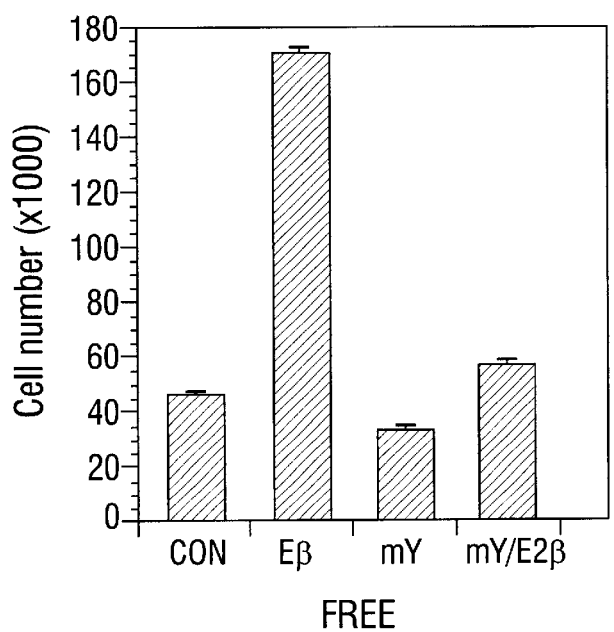
Figure 5B:
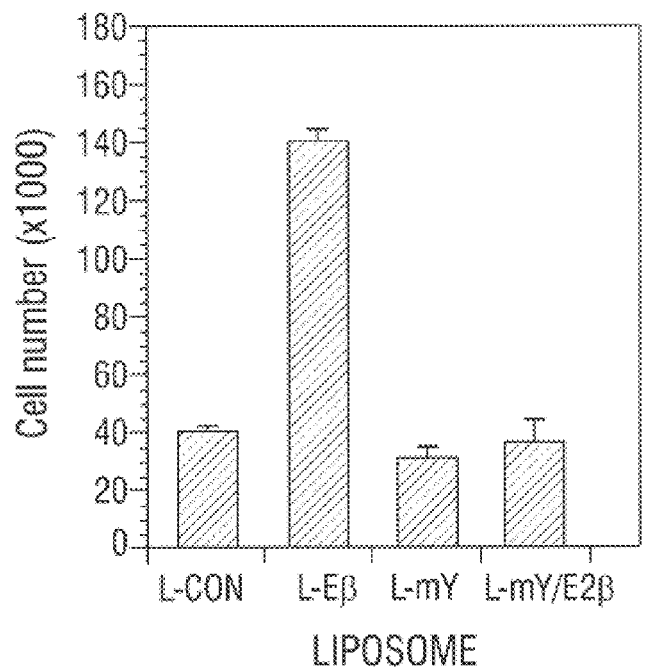

FIG. 5. Growth inhibition of human breast cancer cells by malonyltyrosyl-peptides modeled from ER. mY-peptide (approximately 500 μM) was delivered free or in cationic liposomes to cultures of human breast cancer cells growing in the presence of 1 nM estradiol-17β. After 4 days, growth was quantitated from cell numbers in cultures treated with control (CON), 1 nM E$_2$β (Eβ), free mY-peptide (mY), free mY-peptide+1 nM Eβ (mY/Eβ), or liposome control (L-CON), control liposomes+1 nM E$_2$β (L-Eβ), liposome-encapsulated malonyltyrosyl-peptide (L-mY), or liposome-encapsulated malonyltyrosyl-peptide+1 nM E$_2$β (L-mY/Eβ). Results of three studies are shown with mean ±SEM shown.

Figure 6A:
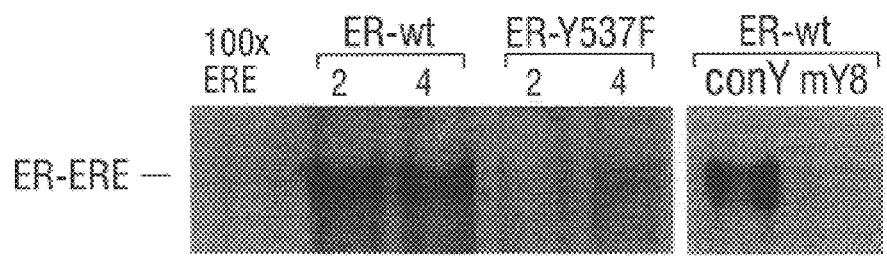

FIG. 6A. Gel mobility shift assays of human ER and ERE. COS-7 cells were transfected with wild-type hER (ER-wt) or hER altered by substitution of phenylalanine for Tyr537 (ER-Y537F) using methods detailed before (Arnold et al., 1995; Arnold and Notides, 1995; Jaiyesimi et al., 1995). Two (2) or four (4) μg protein from total cell lysates of COS-7 cells transfected with ER-wt or ER-Y537F were incubated as before with 100 nM estradiol-17β and $^{32}$P-ERE(Arnoldet al., 1995; Arnold and Notides, 1995; Jaiyesimi et al., 1995). In addition, three μg protein from total lysates of COS-7 cells with ER-wt were incubated with 100×unlabelled ERE (100×ERE) or with 5 μM peptides for 15 min at 4° C. followed by addition of 100 nM estradiol-17β and $^{32}$P-ERE as before (Arnold et al., 1995; Arnold and Notides, 1995; Jaiyesimi et al., 1995). Peptides included control non-phosphorylated octapeptide (conY) or malonyltyrosyl-octapeptide(mY8).

Figure 6B:
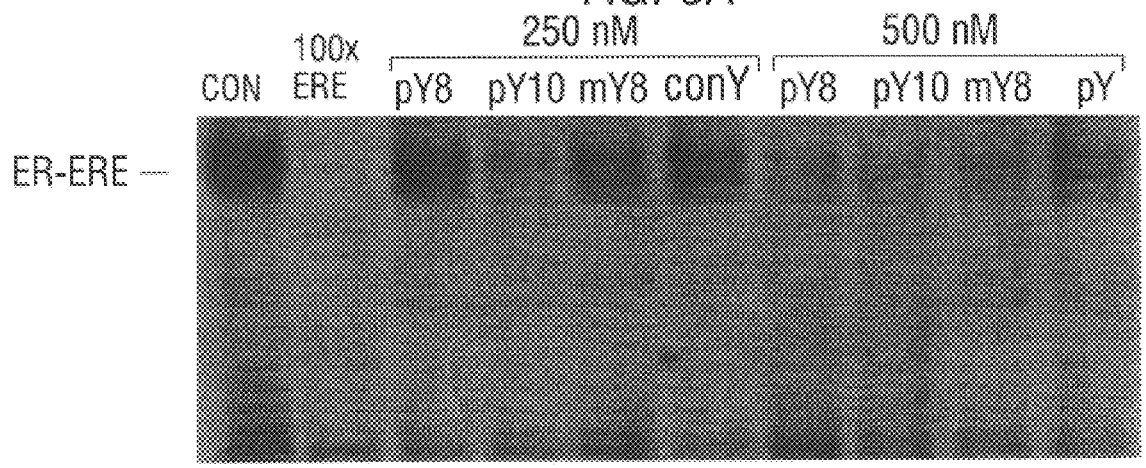

FIG. 6B. Purified human ER (60 nM) was incubated with control solution (CON), a 100-fold molar excess of unlabelled ERE (100 ERE) or with peptides at 250 nM or 500 nM. ER was incubated with peptides for 15 min at 4° C. followed by addition of 100 nM estradiol-17β and $^{32}$P-ERE. Peptides included phosphotyrosyl-octapeptide (pY8), control non-phosphorylated octapeptide (conY), malonyltyrosyl-octapeptide(mY8), phosphotyrosine amino acid alone (pY), as an additional control, and a phosphotyrosyl-decapeptide, N-Val-Pro-Leu-pTyr-Asp-Leu-Leu-Leu-Glu-Met-C (pYl 0) (SEQ ID NO:3). Although not shown, the effect of conY at 500 nM was the same as that shown at a concentration of 250 nM.

Figure 7:
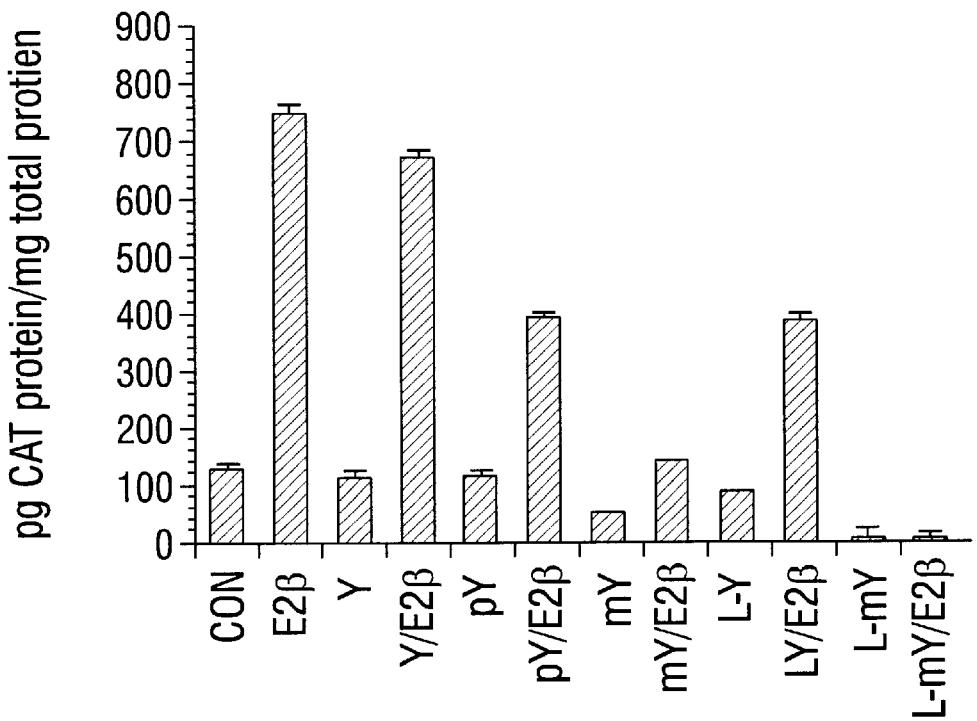

FIG. 7. Phosphotyrosyl peptides elicit suppression of the activation of ERE-CAT reporter gene after transient transfection in MCF-7 breast cancer cells. The inventor used a reporter plasmid with a palindromic ERE and a CAT gene (Pietras et al., 1995; Smith et al., 1995). Substituting the basic reporter plasmid pBLCAT2 for pERE-BLCAT provides an additional control. MCF-7 cells were used to establish transient transfection assays that allow assay of ERE-dependent induction of CAT activity. CAT protein was assessed by established methods (Pietras et al., 1995). Activity of control (CON) and 1 nM estradiol-17β (E$_2$β) for 24 h was assessed using these transfected cells with or without ERE. E$_2$β elicited no change in the basal activity of the CON-CAT gene construct in MCF-7 cells or in the activity of ERE-CAT gene transiently transfected in HBL-100 cells which have no detectable ER. Effects of preincubation with 100 μM control Y-peptide (Y), control Y-peptide+1 nM E$_2$β (Y/E$_2$β), 100 μM phosphotyrosyl-octapeptide(pY), pY-peptide+E$_2$β (pY/E$_2$β), 100 μM malonyltyrosyl-octapeptide (mY) or mY-peptide+E$_2$β (mY/E$_2$β) on MCF-7 cells is shown. In other studies, control Y-peptide (L-Y) or mY-peptide (LmY) were delivered after encapsulation in liposomes (approx. 100 μM) (Pietras, 1978; Szego and Pietras, 1984; Magee et al., 1974), either alone or with E$_2$β (L-Y/E,B or L-mY/Eβ).

Figure 8A:
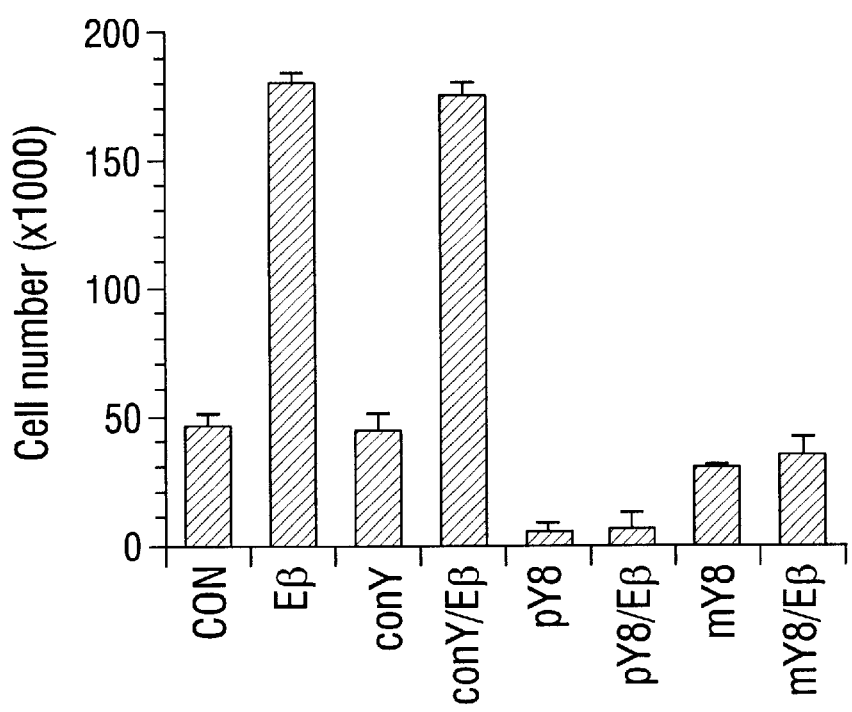

FIG. 8A. Antitumor effect of phosphotyrosyl- and malonyltyrosyl-peptides on human breast cancers in vitro and in vivo. In vitro growth of MCF-7 breast cancer cells was determined by established methods, with initial plating at 5×10$^4$ cells per dish (Pietras et al., 1995; Kunkel et al., 1987). Cells were cultured in the presence of control solution (CON), 1 nM estradiol-17β (Eβ), control Y-peptide (approx. 500 μM in liposomes (Y), control Y-peptide in liposomes plus 1 nM estradiol-17β (Y//Eβ), pY8-peptide (approx. 500 μM) in liposomes (pY), pY8-peptide in liposomes plus estradiol-17β (pY/Eβ), mY8-peptide (approx. 500 μM) in liposomes (mY) or mY8-peptide in liposomes plus estradiol-17β (mY/Eβ). After 4 days, growth was quantitated by cell counts.

Figure 8B:
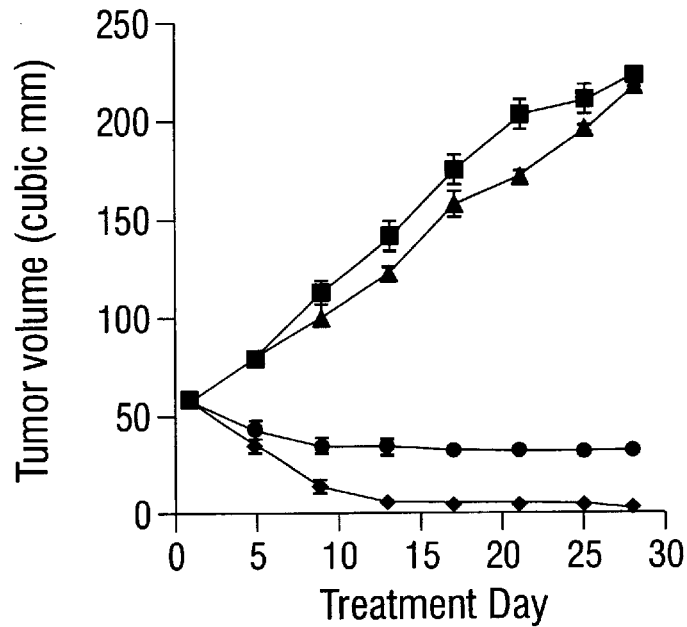

FIG. 8B. MCF-7 breast cancer cells were grown subcutaneously in nude mice. After tumors were >50 mu$^3$ in size, mice were treated by intravenous injection with control solution (squares), malonyltyrosinepeptide at 5 mg/kg (circles), liposome-encapsulatedcontrol (triangles) or liposome-encapsulated malonyltyrosine peptide at an estimated dose of 5 mg/kg (diamonds). Treatments began on day 1 and were then given on days 5, 9, 13, 17, 21 and 25 for a total of7 doses, using 5–7 animals per group.

Figure 9A:
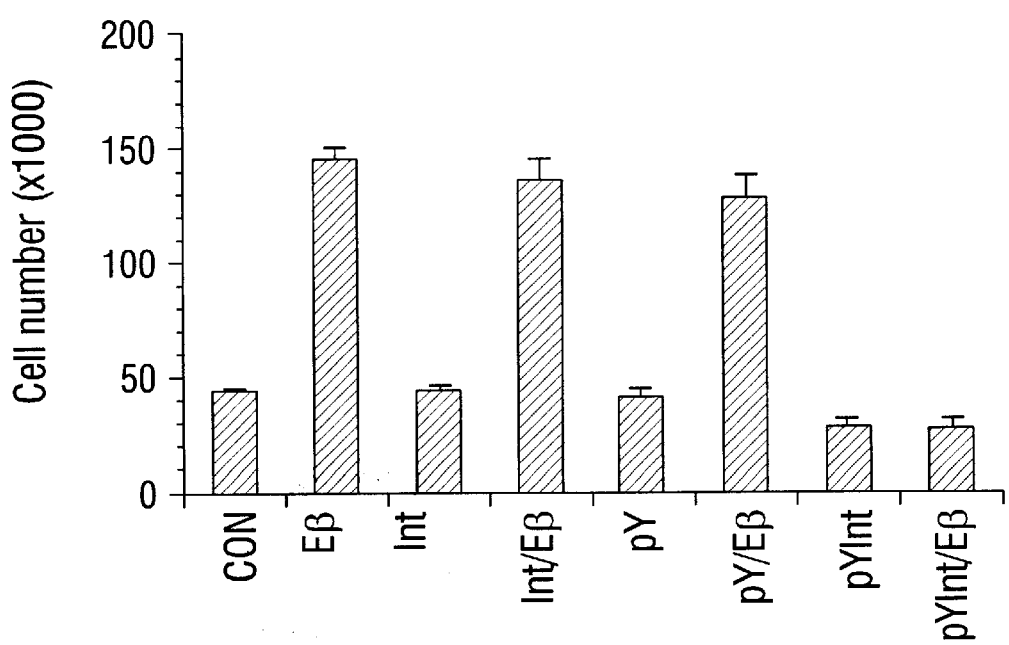

FIG. 9A. In vitro antitumor effect of phosphotyrosyl-peptide antiestrogen coupled with a peptide internalization vector. Growth of MCF-7 breast cancer cells was determined by established methods. with initial plating at 5×10$^4$ cells/dish. Cells were cultured in control solution (CON), 1 nM esttadiol-17β (Eβ), internalization peptide alone at 25 μM (Int), internalization peptide+estradiol-17β (IntEβ), pY-peptide at 25 μM (pY). pY-peptide+estradiol-171 (pY/E0, pY-peptide-internalization peptide hybrid at 25 μM (pYInt) or pY-peptide-internalization peptide+estrdiol-17β (pYlnt/Eβ).

Figure 9B:
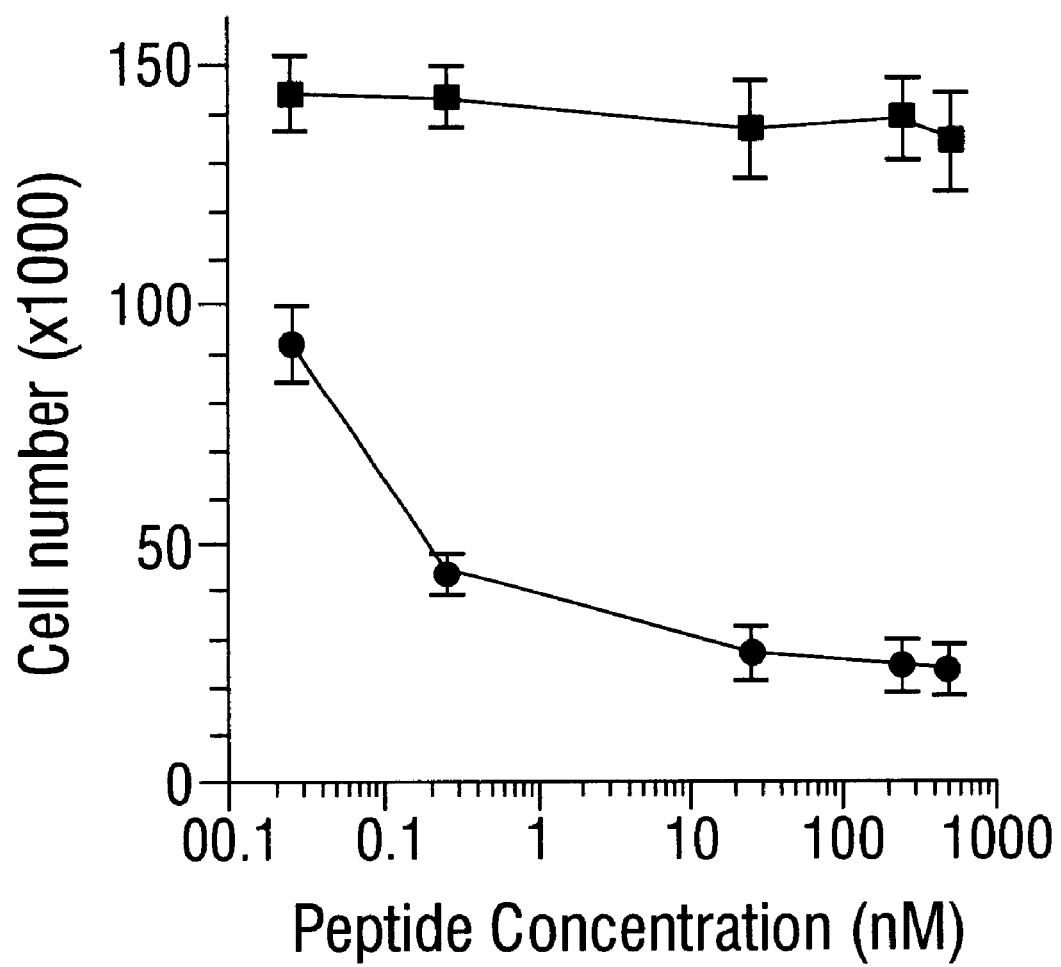

FIG. 9B. In vitro antitumor effect of phosphotyrosyl-peptide antiestrogen coupled with a peptide internalization vector. Growth of MCF-7 breast cancer cells was determined by established methods. with initial plating at 5×10$^4$ cells/dish. In vitro growth of MCF-7 cells treated with 1 nM estradiol-17β plus different concentrations of internalization peptide alone (squares) or internalization peptide coupled with pY-peptide (circles). At 4d, growth was quantitated by cell counts.

4.0 DESCRIPTION OF ILLUSTRATIVE EMBODIMENTS

4.1 DEFINITIONS

The following words and phrases have the meanings set forth below:

a, an: In keeping with the well-established precedent in patent law, the use of the articles "a" and "an" are intended in all instances to mean "one or more."

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell.

Vector: A DNA molecule capable of replication in a host cell and/or to which another DNA segment can be operatively linked so as to bring about replication of the attached segment. A plasmid is an exemplary vector.

4.2 ESTROGEN RECEPTOR

Estrogens promote the growth of breast cells by binding to intracellular receptors which, in turn, act as potent transcription factors for genes encoding growth-regulating peptides (Green and Chambon, 1988; Harris et al., 1992). Blockade of this pathway by interfering with the binding of estrogen to specific receptors is the basis of many breast cancer treatments. The antiestrogen, tamoxifen, works by competitively binding to estrogen receptor (ER), thereby limiting the proliferative effect of estrogen. However, tamoxifen, a partial agonist for ER, also has some undesirable estrogenic effects, including the potential for tumor formation in uterine endometrium and liver (Harris et al., 1992; McGuire and Clark, 1992; Wakeling, 1993). New understanding of ER function now holds promise for the development of other biologic treatments that may improve the control of breast cancer and prolong patient survival (FIG. 1).

Estrogen receptor binds DNA as a homodimer, and dimerization of ER is crucial for transcriptional regulation. Phosphorylation of serine and tyrosine residues in ER may be central to the regulation of receptor dimerization and subsequent interaction with specific estrogen-response elements (ERE) in DNA (Arnold et al., 1995a; Arnold and Notides, 1995; Arnold et al., 1995b; Castoria et al., 1993; Green and Chambon, 1988; Weis et al., 1996). Blockade of estrogen-induced growth of breast cancer cells by tyrosine kinase inhibitors also suggests that tyrosine kinase pathways are important in estrogen action (Pietras et al., 1995; Reddy et al., 1992). Recently, Tyr537 was identified as a major phosphorylationsite on ER from human breast cancer cells (Arnold el al., 1995b). Phosphotyrosineon one ER monomer appears to provide a binding site for association with Src homology 2 domains (SH2-like domains) on a complementary ER monomer (FIG. 1; Arnold et al., 1995a; Arnold and Notides, 1995; Arnold et al., 1995b; Castoria et al., 1993; Daly, 1995). Tyr537 is in a region important in the ligand regulation of ER transcriptional activity, and amino acid alterations at this position appear to shift ER into a conformationthat is active in the absence of ligand (Arnold et al., 1995a; Arnold and Notides, 1995; Arnold et al., 1995b; Castoria et al., 1993; Weis et al., 1996). This tyrosine site may also be important in the estrogen-independent regulation of ER by phosphorylation via tyrosine kinase signaling pathways (FIG. 1; Pietras et al., 1995). Regulation of the biologic activity of ER by estrogen and by growth factor pathways appears to be functionally related to phosphorylationof specific tyrosine residues.

The present invention describes the preparation of phosphotyrosyl- and phosphotyrosyl-mimetic peptides with sequences surrounding ER Tyr537. The phosphotyrosyl-peptides suppressed dimerization of ER monomers and blocked the binding of ER to ERE. Synthetic phosphatase-resistant malonyltyrosyl-peptides were also very active in blocking ER-regulated transcription and arrested the growth of estrogen dependent human breast cancer cells.

4.3 ANTIESTROGEN THERAPY

Antiestrogen therapy has had a significant impact on disease-free survival in patients with breast cancer. The success of endocrine therapy is due to close regulation of breast cell growth by steroid hormones and growth factors. However, as breast cancer progresses, it usually becomes resistant to estrogens, and, consequently, most patients no longer respond to treatment with tamoxifen or other antiestrogens. This study is based on new understanding of the biologic activity of estrogen receptor, a phosphoprotein that forms a homodimer for binding to specific estrogen response elements in DNA, leading to specific gene transcription. It is now clear that the activation of estrogen receptor is related to phosphorylation at tyrosine and other residues, and new approaches to antihormone therapy is possible.

4.4 POLYPEPTIDE ISOLATION AND PURIFICATION

It will be desirable to purify antiestrogen peptides or variants thereof Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an antiestrogen peptide. The term "purified polypeptide" as used herein, is intended to refer to a composition, isolatable from other components, wherein the polypeptide is purified to any degree relative to its naturally-obtainable state. A purified polypeptide or peptide therefore, also refers to a polypeptide, protein, or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1973; Capaldi et al., 1974; Capaldi et al., 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks This is achieved by the use of very fine particles and high pressure to maintain an adequate flow rate. Separation can be accomplished in a matter of rninutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

4.5 SYNTHETIC ANTIESTROGEN PEPTIDES

Because of their relatively small size, the peptides of the invention may be directly synthesized in solution or on a solid support in accordance with conventional techniques. Various automatic synthesizers are commercially available and can be used in accordance with known protocols. See, for example, Stewart and Young, (1966); Voss et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

4.6 ANTIGEN COMPOSMONS

The present invention also provides for the use of antiestrogen peptides as antigens for the immunization of animals relating to the production of antibodies. It is envisioned that these peptides, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyanin (KLH) or bovine serum albumin (BSA).

4.7 VECTORS FOR CLONING, GENE TRANSFER AND EXPRESSION

Within certain embodiments expression vectors are employed to express the antiestrogen polypeptide products, which can then be purified and, for example, be used to vaccinate animals to generate antisera or monoclonal antibody with which firther studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stablecell clones expressing the products are also provided, as is an element that links expression of the drug selection markers to expression of the polypeptide.

4.7.1 Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of MRNA into a gene product. In other embodiments, expression only includes transcriptionof the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mannmalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expressionbut, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand; a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

4.7.2 Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thyridine kinase (tk) or chloramphenicol acetyltransferase (CAr)

may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

4.7.3 Multigene Constructs and IRES

In certain embodiments of the invention, the use of internml ribosome binding sites (IRES) elements are used to create multigene, or polycistronic, messages. IRES elements are able to bypass the ribosome scanning model of 5¢ methylated Cap dependent translation and begin translation at internal sites (Pelletier and Sonenberg, 1988). IRES elements from two members of the picomavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancerto transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

4.7.4 Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses(Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1908; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Generation and propagation of adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Richetal. 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Methods for culturing 293 cells and propagating adenovirus have been described. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell-and its descendants. The retroviral genome contains three genes, gag, pol, and env that code for capsid proteins, polymerase enzyme, and envelope components, respectively. A sequence found upstream from the gag gene containsa signal for packaging of the genome into virions. Two long terminal repeat (LTR) sequences are present at the 5¢ and 3¢ ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975). A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by-using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varnus et al., 1981). Another concern with the use of defective retrovirus vectors is the potential appearance of wild-type replication-competent virus in the packaging cells. This can result from recombinationevents in which the intact-sequence from the recombinant virus inserts upstream from the gag, pol, env sequence integrated in the host cell genome. However, new packaging cell lines are now available that should greatly decrease the likelihood of recombination (Markowitzet et al., 1988; Hersdorfferet et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Herinonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependentpackaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chaqng et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and VanDerEb, 1973; Chen and Okayama, 1987; Rippe et al., 1990) DEAE-dextran(Gopal, 1985), electroporation(Tur-Kaspaet et al., 1986; Potter et al., 1984), direct microinjection (Harland and Weintraub, 1985),DNA-loaded liposomes (Nicolau and Sene, 1982; Fraley et al., 1979) and lipofectamine-DNA complexes, cell sonication (Fechheimer et al., 1987), gene bombardment using high velocity microprojectiles(Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet ftuther embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfilly injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The micro projectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment Again, DNA encoding a particular gene may be delivered via this method and still be incorporated by the present invention.

In one embodiment, such expression constructs may be entrapped in a liposome, lipid complex, nanocapsule, or other formulation using one or more of the methods disclosed in Section 4.8. Also contemplated are lipofectamine-DNA complexes. For example, liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediatedgene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP 0360257, specifically incorporated herein by reference).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified sells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the fnnction of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts. The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

4.8 PRIMERS AND PROBES

The term primer, as defined herein, is meant to encompass any nucleic acid that is capable of priming the synthesis of a nascent nucleic acid in a template-dependent process. Typically, primers are oligonucleotides from about ten to about fifteen base pairs in length or even longer sequences such as those from about twenty to about 30 base pairs or more in length, with even longer sequences be employed for certain applications. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemiluminescent(luciferase).

4.9 TEMPLATE DEPENDENT AMPLIFICATION METHODS

A number of template dependent processes are available to amplify a particular nucleic acid sequence present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure (RT-PCR™) may be performed in order to quantify the amount of MRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT ApplicationNo. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, ie., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2,202,328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g, biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Int. Pat. Appl. Publ. No. WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Eur. Pat. Appl. Publ. No. EP 329,822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without addition of enzymnes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu and Wang, (1989), incorporated herein by reference in its entirety.

4.10 SOUTHERN/NORTHERN BLOTTING

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

4.11 SEPARATION METHODS

It normally is desirable, at one stage or another, to separate nucleic acids, such as separating amplification products from a, template and excess primer, for the purpose of determining whether specific amplification has occurred. In one embodiment, amplification products are separated by agarose, agarose-acrylamide or polyacrylamide gel electrophoresis using standard methods (see e.g., Sambrook et al., 1989). Alternatively, chromatographic techniques may be employed to effect separation. There are many kinds of chromatography which may be used in the present invention: adsorption, partition, ion-exchange and molecular sieve, and many specialized techniques for using them including column, paper, electrophoresis, thin-layer and gas chromatography (Freifelder and Freifelder, 1968a,b; Freifelder, 1968a,b; Freifelder anad Better, 1982).

4.12 DETECTION METHODS

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabel probes or primers identify the target during or following amplification. One example of the foregoing is described in U.S. Pat. No. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used. Using the sequences disclosed herein, oligonucleotide primers may be designed to permit the amplification of sequences throughout the peptide-encoding polynucleotide that may then be analyzed by direct sequencing.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Antitumor Effect of Phosphotyrosyl Peptide Analogs Targeted to ER

It has been shown that purified recombinant human ER from MCF-7 breast cancer cells reacts specifically with synthetic ERE in a gel mobility shift assay, allowing formation of an ER-ERE complex. This interaction is eliminated by competition with 0.01–10 $\mu$M phosphotyrosine but not by competition with 0.01–50 $\mu$M phosphoserine. Since site directed mutagenesis studies show that Tyr537 is the predominant phosphotyrosyl residue in ER, several peptides were prepared which contain the sequence corresponding to the phosphorylation site at Tyr537 in ER (Arnold et al., 1995a; Arnold and Notides, 1995; Arnold et al., 1995b; Castoria et al, 1993). The phosphorylated octapeptide, pY, contains the sequence PLpYDLLLE (SEQ ID NO:2), and its nonphosphorylated analog, Y, has the sequence PLYDLLLE (SEQ ID NO:1).

By application of molecular sizing chromatography with Sephadex G-200 (Pharmacia), it was found that the phosphotyrosyl-peptide, pY, inhibits the dimerization of estrogen receptor (FIG. 2).

The purified recombinant ER was incubated with [$^3$H]-estradiol and phosphotyrosyl- or nonphosphorylated-peptides, followed by gel chromatography. In the presence of Y-control peptide, the [$^3$H]-etrsiol-ER complex eluted at 34 ml, near the elution peak for aldolase marker protein (158 kDa) and correspondingto the expected size for a dimeric receptor complex formed in the presence of estrogen. At 25 $\mu$M, the pY-peptide appears to elicit dissociation of the [$^3$H]-estradiol-ER to a monomer form, with elution of predominantly lower molecular size protein at 40 ml (corresponding to the elution peak for albumin, a 67 kDa protein).

Interaction of ER with nuclear ERE is prerequisite for activation of transcription. To assess the specific binding of ER with ERE, purified recombinant human ER from MCF-7 breast cancer cells were used. A double-stranded 27-bp probe (5'-GATCCTAGAGGTCACAGTGACCTACGA-3') (SEQ ID NO:12) encoding the Xenopus vitellogenin A$_2$ ERE was $^{32}$P-end-labeled with polynucleotide kinase. Gel mobility shift assays for the human ER were performed as described (Arnold et al., 1995a; Arnold and Notides, 1995; Arnold et al., 1995b). The ER in 20 mM reaction buffer (HEPES, pH 7.5, 1 mM EDTA, 100 mM KCl, 1 mg/ml BSA, 100 nM estradiol, 15% glycerol, proteinase inhibitors) was incubated with 500 ng of poly (dI-dC) for 15 min at 4° C., and then 20 fmol of the $^{32}$P-labeled ERE probe was added for 15 min at 4° C. in a total volume of 20 $\mu$l. Samples were loaded onto a pre-electrophoresed 5% polyacrylamide gel followed by electrophoresis with cooling at 175 V for 3 h in 25 mM TRIS, pH 8.0 with 152 mM glycine and 1 mM EDTA. Under these conditions, the human ER reacts specifically with synthetic ERE in the gel mobility shift assay, allowing formation of an ER-ERE complex. Further study of the functional regulation of ER by phosphotyrosyl-peptide was done by use of a reporter gene with an ERE (FIG. 3; Pietras et al., 1995).

In earlier work, it was found that estrogen promotes activation of an ERE-CAT reporter construct in MCF-7 cells, as measured with a sensitive ELISA-based CAT assay.

Specificity of reporter activation for ERE and for ligand (17β-estradiol vs. 17α-Estradiol, progesterone) was confirmed as in previous studies (Pietras et al., 1995). Delivery of pY-peptides by use of cationic liposomes (phosphatidylcholine, stearylamine and cholesterol; Pietras, 1978) elicited a significant suppression of the estrogen-induced activation of ERE-CAT reporter construct (P<0.001; FIG. 3). However, the Ycontrol peptide did not significantly influence the effect of estrogen.

The antitumor activity of phosphotyrosyl-peptides was assessed in human breast cells under in vitro conditions. Human malignant breast cells included MCF-7, ZR75–1 and T47D cells with significant ER levels. Studies of cell growth using in vitro assays for cell proliferation are shown in Table 3. To evaluate the growth of breast cells, aliquots of 4×10⁴ cells were plated in RPMI medium 1640 with 2 mM glutamine and 1% penicillin G-streptomycin-fungizone solution (Pietras et al., 1995). In studies requiring estrogen-free conditions, medium without phenol red and supplemented with 10% heat-activated, dextran-coated charcoal-treated fetal bovine serum was used. Medium with 10% heat-inactivated fetal calf serum was used for standard plating conditions. After cell adherence, experimental media were added. Following incubation at 37° C., plates were washed and cell counts obtained as before (Pietras et al., 1995). The results of the study in Table 3 suggest that liposome-delivered pY-peptide has efficacy in the inhibition of estrogen-induced growth of human breast cancer cells in vitro.

One problem with the use of phosphotyrosyl-peptides in vitro or in vivo is the susceptibility of the constructs to degradation by cellular tyrosine phosphatase enzymes. To address this difficulty, phosphotyrosyl-mimic peptides were prepared that use a malonyl structure rather than phosphate residues at tyrosine sites. The malonyltyrosyl-peptides contain the sequence surrounding Tyr537 in ER (Arnold et al., 1995a; Arnold and Notides, 1995; Arnold et al., 1995b; Castoria et al., 1993). The malonyltyrosyl-octapeptide, mY, contains the sequence PLmYDLLLE (SEQ ID NO:3). Malonyltyrosine residues appear to mimic the phosphotrosine conformation in proteins and may evade the action of cellular enzymes targeted to phosphotyrosine(Ye and Burke, Jr., 1995; Kole et al., 1995).

TABLE 3

GROWTH INHIBITION OF HUMAN BREAST CANCER CELLS BY PHOSPHOTYROSYL-PEPTIDES MODELED FROM ER[1]

| Breast Cancer Cell | Growth Inhibition (%) |
|---|---|
| MCR-7 | 96.7 ± 3.3 |
| ZR75-2 | 90.2 ± 4.5 |
| T47D | 87.9 ± 6.2 |

[1]pY-peptide (approx. 50 μM) was delivered in cationic liposomes to cultures of human breast cancer cells growing in the presence of 1 nM estradiol-17β. After 4 days, growth was quantitated in cultures treated with pY-peptide and expressed relative to that of controls exposed to blank liposomes (given as % growth inhibition). Results of three studies are shown with mean ± SEM shown. Y-peptide had no significant effect on the growth of breast cancer cells in this assay.

It is found that malonyltyrosyl-peptide constructs, as phosphotyrosyl-peptides, block dimerization of estrogen receptors in human breast cancer cells (FIG. 2). In addition, the malonyltyrosyl-peptide suppresses binding of estrogen receptor to specific estrogen-response elements in human breast cancer cells. This ER-ERE interaction is blocked by competition with 0.2 μM mY-peptide but not by competition with 5 μM Y-peptide. Further study of the functional regulation of ER by phosphotyrosyl-peptide was done by use of a reporter gene with an ERE (FIG. 4; Pietras et al., 1995). Delivery of free or liposome-encapsulated mY-peptides (Pietras, 1978) elicited a significant suppression of the estrogen-induced activation of ERE-CAT reporter construct (P<0.001; FIG. 4). However, the control peptide did not significantly influence the effect of estrogen.

The antitumor activity of malonyltyrosyl-peptides was assessed in MCF-7 human breast cells under in vitro conditions. Studies of cell growth using in vitro assays for cell proliferation are shown in FIG. 5. The results of the study in FIG. 5 suggest that free, as well as liposome-delivered, mY-peptide has efficacy in the inhibition of estrogen-induced growth of human breast cancer cells in vitro.

Cell growth studies with BT-20 and SKBR3 cells with no detectable-wild-type ER and HBL-100 cells, non-malignant breast cells with minimal to no ER, may also be performed. Since results of in vitro and in vivo tumor growth studies are sometimes divergent, the inventor has studied the growth response of MCF-7 cells to estrogen and to antiestrogenic-peptides in vivo, with methods as before (Pietras et al., 1995; Pietras et al., 1994). Tumor cells may be injected subcutaneously at 5×10⁷ cells/animal in female athymic mice primed with estrogen (1.7 mg/pellet).

After 14–21 days, animal with tumors of similar size will be randomized to treatment with pY-peptide, mY-peptide or control peptides for an additional 28 days. The latter treatment may be initiated with tumors at approximately 50 mm³ in size. Tumor volumes of MCF-7 cells with or without treatments are recorded, and any tumors formed are analyzed for ER and PR by immunohistochemistry. Such studies are especially important to assess the efficacy of antiestrogenic-peptides as potential therapeutic agents in human breast cancer cells which express estrogen receptor at levels commonly found in human malignancies (McGuire and Clark, 1992). The dose of peptides, the type (phosphotyrosyl versus malonyltyrosyl) and size of peptides used and the route of delivery (intraperitoneal, subcutaneous or liposomal) of peptides are all factors that may be determined using ordinary skill in the art in light of the present teaching, using methods as described before (Pietras et al., 1994).

These studies were based on a new understanding of the biologic activity of estrogen receptor, a phospho-protein found in more than two-thirds of human breast tumors. It is now clear that activation of estrogen receptor by phosphorylation of specific tyrosine residues in the receptor can occur by both estrogen-dependent and estrogen-independent pathways (Arnold et al., 1995a; Arnold and Notides, 1995; Arnold et al., 1995b; Castoria et al., 1993; Kato et al., 1995; Pietras et al., 1995; Reddy et al., 1992; Smith et al., 1995; Szego and Pietras, 1984; Weis et al., 1996), and novel approaches to improved antihormone therapy are possible. The invention provides a new class of antiestrogenic-peptides (Table 4) targeted to ER, which disrupt ER function and inhibit the growth of human breast cancers with ERs.

TABLE 4

PEPTIDES OF THE PRESENT INVENTION

| PEPTIDE SEQUENCE | CHARACTERISTICS | SEQ ID NO: |
|---|---|---|
| VPLpYDLLLEM | phosphotyrosine peptide (10-mer) | 3 |
| VPLYDLLLEM | control non-phosphorylated peptide (10-mer) | 5 |

TABLE 4-continued

PEPTIDES OF THE PRESENT INVENTION

| PEPTIDE SEQUENCE | CHARACTERISTICS | SEQ ID NO: |
|---|---|---|
| VPLmYDLLLEM | malonyltyrosine peptide (10-mer) | 6 |
| PLpYDLLLE | phosphotyrosine peptide (8-mer) | 2 |
| PLmYDLLLE | malonyltyrosine peptide (8-mer) | 4 |
| PLYDLLLE | control nonphosphorylated peptide (8-mer) | 1 |
| LpYDLLL | 6-mer | 7 |
| LmYDLLL | 6-mer | 8 |
| pYDLLL | 5-mer | 9 |
| mYDLLL | 5-mer | 10 |
| LmYDLL | 5-mer | 11 |

All peptides have N-terminal acetylation and C-terminal amides;
pY = phosphotyrosine; mY = malonyltyrosine

5.2 Example 2

Antitumor Effect of Phosphotyrosy Peptide Analogs Targetd to Disrupt DNA Binding of ER in Human Breast Cancer This example describes the effect of phosphotyrosyl peptides on ER dimerization and DNA binding. Eight- to ten-amino acid phosphotyrosyl- and phosphotyrosyl-mimeticpeptides with sequences surrounding ER Tyr537 were prepared and tested for their efficacy in the blockade of ER dimerization and in the suppression of ER binding to ERE. Phosphatase-resistant malonyltyrosyl-peptides designed for in vivo application are also evaluated for inhibition of ER-regulated transcription and for antitumor activity. These data show that peptides targeted to disrupt dimerization and DNA binding of ER proteins offer a new class of antiestrogens for cancer therapy.

5.2.1 Methods 5.2.1.1 Preparation of Peptide Antiestrogens

Phosphotyrosineand phosphoserine were obtained in pure form (Sigma, St. Louis, Mo.). Octapeptides and decapeptides with or without phosphotyrosine (UCLA Peptide Synthesis Facility and Genosys, The Woodlands, Tex.) or malonyltyrosine (Anaspec Laboratories, Foster City, Calif.) residues were synthesized by established methods with N-terminal acetylation and a C-terminal amide (Arnold and Notides, 1995; Ye et al., 1995; Ye and Burke Jr., 1995). All peptide constructs were characterized by HPLC and mass spectral analysis and found to be more than 95% pure.

In some studies, peptides were delivered after encapsulation in liposomes (phosphatidylcholine, stearylamine and cholesterol) using methods described in detail before (Pietras, 1978; Magee et al., 1974).

5.2.1.2 Gel Chromatography

Molecular sizing chromatography with Sephadex G-200 (Phannacia, Piscataway, N.J.) was used by established methods (Arnold and Notides, 1995; Pietras and Szego, 1980). The gel column was equilibrated by use of ovalbumin, bovine serum albumin, aldolase, gamma-globulin and blue dextran at 4° C.

5.2.1.3 Gel Mobility Shift Assay

A double-stranded 27-basepair probe (5'-GATCCTAGAGGTCACAG TGACCTACGA-3') (SEQ ID NO: 13) encoding the Xenopus vitellogenin $A_2$ ERE was $^{32}$P-end-labeled with polynucleotide kinase. ER was prepared from soluble cell extracts as before (Arnold et al., 1995; Arnold et al., 1995; Pietras and Szego, 1980), or recombinant human ER was used in purified form (Panvera, Madison, Wis.) (Oboum et al., 1993). Gel mobility shift assays for the human ER were performed as described (Arnold et al., 1995; Arnold et al., 1995). In brief, ER in 20 mM reaction buffer (HEPES, pH 7.5, 1 mM EDTA, 100 mM KCI, 1 mg/ml BSA, 100 nM estradiol, 15% glycerol, proteinase inhibitors) was incubated with 500 ng of poly (dI-dC) for 15 min at 4° C., and then 20 fmol of the $^{32}$P-labeled ERE probe was added for 15 min at 4° C. in total volume of 20 µl. Samples were loaded onto a pre-electrophoresed 5% polyacrylamide gel followed by electrophoresis with cooling at 175 V for 3 h in 25 mM TRIS, pH 8.0, 152 mM glycine and 1 mM EDTA.

5.2.1.4A Site-Directed Mutagenesis and Transfections

The 1.8 kb complete coding sequence of ER was cloned into the EcoRl site of pIC20H (Ahrens et al., 1992). Oligodirected mutagenesis of Tyr537 in the wild-type ER to phenylalanine (Y537F) was performed using the following oligonucleotide: AAGAACGTGGTGCCCCTCTTCGAC-CTGCTGCTGGAGATG (Y537F; (GIBCO BRL, Grand Island, N.Y.) (SEQ ID NO:14) as detailed elsewhere (Weis et al., 1996). After mutagenesis, clones were subjected to dideoxy-sequence analysis to confirm the sequence using a Sequenase 2.0 kit (Amersham, Arlington Heights, Ill.). ER cDNA was excised from pIC20H using EcoRI and ligated into the EcoRI site of pcDNA3, a neomycin containing vector (Invitrogen, Carlsbad, Calif.), followed by restriction enzyme analysis with either XbaI or NotI to distinguish the orientation of the insert. Transfections were done in COS-7 cells (ATCC) using established methods (Kato et al., 1995; Pietras et al., 1995; Weis et al., 1996).

5.2.1.5 ERE-CAT Reporter Gene Assay

A reporter plasmid was used with palindromic ERE, derived from vitellogenin A2 promoter, and CAT gene driven by a partial promoter sequence of thymidine kinase (Pietras et al., 1995; Ernst et al., 1991). Substituting the basic reporter plasmid pBLCAT2 for pERE-BLCAT provides an additional control. MCF-7 breast cancer cells were used to establish transient transfection assays that allow assay of ERE-dependent induction of CAT activity. CAT protein was assessed by established methods (Pietras et al., 1995). Peptides were delivered in solution or by use of liposomes (phosphatidylcholine, stearylamine and cholesterol) using methods described in detail before (Pietras, 1978; Magee et al., 1974).

5.2.1.6 Cell Growth Assays

In vitro growth of MCF-7, T47D and HBL-100 human breast cells (ATCC) was determined by established methods (Pietras et al., 1995; Pietras et al., 1994). For assessment of cell growth in vivo, MCF-7 tumor cells were injected subcutaneously at $5 \times 10^7$ cells/animal in female athymic mice primed with estrogen (1.7 mg/pellet) (Pietras et al., 1995; Pietras et al., 1994). After 14–21 days, animals with tumors at approximately 50 mm$^3$ in size were randomized to treatment with test or control peptides. Tumor volumes of MCF-7 cells were recorded for an additional 28 days.

5.2.2 Results 5.2.2.1 Phosphotyros-Peptide Disrupt Dimerization ERs

To test the hypothesis that Tyr537 and neighboring amino acids may function as Src homology 2-like domains for specific interaction of ER monomers, the inventor prepared peptides that contain the sequence corresponding to the phosphorylation site at Tyr537 in ER (Arnold and Notides, 1995; Arnold et al., 1995; Cohen et al., 1995; Greene et al., 1986) and assessed their capability to block dimerization of ER. The phosphorylated octapeptide, pY8, contains the sequence, N-Pro-Leu-pTyr-Asp-Leu-Leu-Leu-Glu-C (PLpYDLLLE) (SEQ ID NO:2), correspondingto the carboxy-terminal amino acid residues 535–542 of ER (Table 5). Its control analog, conY, has the sequence, N-Pro-Leu-Tyr-Asp-Leu-Leu-Leu-Glu-C(PLYDLLLE) (SEQ ID NO:1), with the tyrosine residue not phosphorylated (Table 5). By use of molecular sizing chromatography, the inventor found that phosphotyrosyl-peptide pY8 inhibits the dimerization of ER (FIG. 2). ER was incubated with [$^3$H]-estradiol and the test peptides, followed by gel chromatography. In the presence of control Y peptide, the [$^3$H]-estradiol-ER complex eluted near the elutionpeak for aldolase marker protein (158 kDa), corresponding to the expected size for a dimeric receptor complex formed in the presence of estrogen. At 25 $\mu$M, pY8-peptide elicits dissociation of the [$^3$H]-estradiol-ER to a monomer form, with elution of predominantly lower molecular size protein corresponding to the elution peak for albumin, a 67 kDa protein. These results are consistent with prior findings implicating phosphotyrosine-537 in the regulation of ER dimerization (Arnold and Notides, 1995).

5.2.2.3 Peptide Antiestrogens Disrupt Estrogen-Regulated Gene Transcription

Study of the functional regulation of ER by phosphotyrosyl-peptides was done with a reporter gene with an ERE (FIG. 7). The inventor found that estrogen promotes activation of an ERE-CAT reporter construct in MCF-7 breast cancer cells, as measured with a sensitive ELISA-based CAT assay (Pietras et al., 1995). Incubation of cells with phosphotyrosyl-peptides, but not control nonphosphorylated peptides, elicits a reduction in the expected stimulatory effect of estradiol (P<0.05, t-test; FIG. 7). Since phosphorylated ligands may be dephosphorylated in cells by phosphatases and may have only limited permeability, non-natural amino acids that minic the charge and molecular configuration of phosphotyrosine were used in the development of alternative antiestrogen agents. The carboxyl-containing derivative, malonyltyrosine, is resistant to phosphatases (Ye et al., 1995; Ye and Burke Jr., 1995).

TABLE 5

SYNTHETIC PHOSPHORYLATED AND NONPHOSPHORYLATED PEPTIDES BASED ON ER AMINO ACID SEQUENCE SURROUNDING TYR537

| Peptide | SEQ ID NO: | Amino Acid Sequence |
| --- | --- | --- |
| pY8 | 2 | N-Pro-Leu-pTyr-Asp-Leu-Leu-Leu-Glu-C |
| conY | 1 | N-Pro-Leu-Tyr-Asp-Leu-Leu-Leu-Glu-C |
| mY8 | 4 | N-Pro-Leu-mTyr-Asp-Leu-Leu-Leu-Glu-C |
| pY10 | 3 | N-Val-Pro-Leu-pTyr-Asp-Leu-Leu-Leu-Glu-Met-C |

The data in Table 5 show the amino acid sequence of peptides synthesized for use in these studies. For example, pY8 represents the octapeptide from amino acid 535–542 in ER, with phosphorylation (p) of tyrosine. The designation mY8 represents a malonyl tyrosine.

5.2.2.2 Peptide Antisetrogens Suppress Binding of ER to ERE

Interaction of ER with nuclear ERE is prerequisite for activation of transcription. To assess the binding of ER with ERE, a double-stranded 27-bp probe encoding the Xenopus vitellogenin A$_2$ ERE was $^{32}$P-end-labeled with polynucleotide kinase. Gel mobility shift assays for ER were performed as before (Arnold et al., 1995; Arnold and Notides, 1995; Arnold et al., 1995). Under these conditions, human wild-type ER from cell extracts reacts specifically with synthetic ERE in the gel mobility shift assay, allowing formation of an ER-ERE complex (FIG. 6A). The importance of tyrosine in ER for association with ERE was then assessed by use of site-directed mutagenesis (Arnold et al., 1995; Weis et al., 1996; White et al., 1997; Kunkel et al., 1987). Substitution of phenylalanine for Tyr537 in human ER leads to a marked reduction of ER-ERE binding (FIG. 6A). As with the cell-derived ER extracts, purified recombinant human ER also forms a stable ER-ERE complex (FIG. 6B). This interaction is slightly reduced by competition with 0.5 $\mu$M phosphotyrosine alone but not by competition with up to 50 $\mu$M phosphoserine. In addition, ER-ERE interaction is effectively blocked by competition with 0.5 $\mu$M phosphotyrosyl-peptides but not by competition with nonphosphorylated control-peptides (FIG. 6B). Thus, phosphotyrosyl-peptides targeted to Tyr537 block dimerization of ER monomers and suppress the binding of ER to ERE.

Malonyltyrosine was incorporated into a short octapeptide analogue targeted to Tyr537 in ER, with the sequence, N-Pro-Leu-mTyr-Asp-Leu-Leu-Leu-Glu-C(PLmYDLLLE) (SEQ ID NO:4) and termed mY8 (Table 5). As with pY8-peptide, mY8 was active in blocking ER-ERE interaction, using cell-derived receptor (FIG. 6A) or purified ER (FIG. 6B). In addition, incubation of MCF-7 cells transfected with ERE-CAT gene with free mY8-peptide also elicited a reduction in estrogen-induced activation of the reporter gene (FIG. 7). When mY8-peptide was encapsulated in liposomes (Pietras, 1978), it provoked a more significant suppression of estrogen-induced ERE-CAT reporter activity (P<0.001; FIG. 7). Thus, malonyltyrosyl-peptides, as phosphotyrosyl-peptides, may be useful in the disruption of ER signaling and growth promotion in intact breast cancer cells.

5.2.2.4 Antitumor Effects of Peptide Antiestrogens

The antitumor activity of phosphotyrosyl-peptide analogues was assessed in MCF-7 human breast cancer cells under in vitro and in vivo conditions. Studies of cell growth using in vitro assays for cell proliferation are shown in FIG. 8A. The results show that liposome-delivered pY8- and mY8-peptides both have efficacy in vitro, with significant inhibition of the estrogen induced growth of human breast cancer cells (P<0.001). T47D breast cancer cells that express ER also showed a 90.1±4.5% reduction in cell growth in vitro when treated with pY8-peptide in liposomes as compared to controls (P<0.001), while HBL-100 breast cells with minimal to no ER had only a 5.0+2.1% reduction in cell growth on treatment with pY8-peptide in liposomes. The latter results suggest that the efficacy of the antiestrogenic peptides is limited to cells with ER expression.

The growth response of MCF-7 breast cancer cells to estrogen and to malonyltyrosyl-peptides was also evaluated in vivo (Pietras et al., 1995; Pietras et al., 1994). Malonyltyrosyl-peptides were free or encapsulated in liposomes and delivered by intravenous injection using methods described before (Pietras et al., 1995; Ye et al., 1995; Pietras et al., 1994). The malonyltyrosyl-peptides show significant antitumor activity in blocking the growth of human breast cancer cell xenografts (P<0.01), with greater growth inhibition from liposome-encaspsulated peptide (FIG. 8B).

It is clear that activation of estrogen receptor by phosphorylation of conserved tyrosine residues in the receptor is important in receptor-medicated growth, and novel approaches to improved antihormone therapy are possible (Arnold et al., 1995; Pietras et al., 1995; Arnold and Notides, 1995; Srnith et al., 1995; Szego and Pietras, 1984). Tyr537 is located at the beginning of exon 8 of the ER gene encoding the carboxy-terminalportion of the hormone-binding domain, a region to which dimerization and AF-2 functions have been ascribed. This region of the ER is also conserved in evolution between species but has some divergence from other members of the steroid hormone receptor superfamily. Substitution of phenylalanine for Tyr537 in human ER leads to a significant reduction of ER-ERE binding, suggesting the importance of Tyr537 in ER for association with ERE. Non-conservative substitutions at Tyr537 with amino acids having reduced hydrophobicity or smaller side chains appears to result in unexpected constitutive activity of ER. Recently, a natural mutation of Tyr537 to asparagine was also detected in ER derived from a metastatic breast cancer, and the tumor was noted to exhibit strong hormone-independent activity. Thus, these data suggest that Tyr537 may be required to maintain ER in a transcriptionally inactive state. Modification of Tyr537 by estrogen binding or by tyrosine kinase signaling pathways may elicit a conformational change in the ligand-binding domain of the receptor required for activation of transcription.

Tyr537 is located immediately anino-termninal of the AF-2 activation helix, a region that is important in the regulation of receptor transcriptional activity (Arnold and Notides, 1995, Arnold et al., 1995, Danielian et al., 1992; Weis et al., 1996; White et al., 1997). Tyr537 also lies within the hormone-binding domain of the ER, and phosphorylation of this residue is reported to be required for efficient estrogen binding and for optimal ER dimerization and association with an ERE. However, the strong transcriptional activity resulting from natural and site-directed substitution of Tyr537 to non-conservative amino acids implies that adjacent regions of the hormone-binding domain, such as leucine repeats at position 536 and 539–541, are also involved in ER dimerization and DNA binding. Function of the AF-2 domain appears to require a highly conserved carboxy-terminus region of human ER corresponding to residues 534–548.

The studies described here provide evidence for the efficacy and clinical potential of new antiestrogenic peptides targeted to selectively disrupt dimerization and DNA binding of the estrogen receptor in human breast cancer cells. The small synthetic peptides blocked dimerization of ER monomers in solution and suppressed the binding of ER to a palindromic ERE. Phosphatase-resistant malonyltyrosyl-peptides designed for in vivo application also blocked ER-regulated gene transcription and arrested the growth of estrogen-dependent human breast cancer cells. Thus, peptides targeted to disrupt dimerization and DNA binding of ER proteins represent a new class of antiestrogens for breast cancer therapy.

5.3 Example 3

Activity and Selectivity of Peptides in Vitro and in Vivo Assays

To address the issue of selectivity, it is important to review biologic information about the sequence of the estrogen receptor (ER) that is targeted by the small peptide antiestrogens. This region of the estrogen receptor is highly conserved in estrogen receptors found among all species ranging from human to amphibians (Table 6)

TABLE 6

HIGHLY CONSERVED REGIONS OF ERs FROM VARIOUS SPECIES

| Conserved Region | Amino Acid Position | Source |
| --- | --- | --- |
| PLYDLLLEMLDA (SEQ ID NO:15) | 535–546 | human ER |
| PLYDLLLEMLDA (SEQ ID NO:16) | 539–550 | mouse ER |
| PLYDLLLEMLDA (SEQ ID NO:17) | 540–551 | rat ER |
| PLYDLLLEMLDA (SEQ ID NO:18) | 535–546 | porcine ER |
| PLYDLLLEMLDA (SEQ ID NO:19) | 536–547 | sheep ER |
| PLYDLLLEMLDA (SEQ ID NO:20) | 529–540 | chicken ER |
| PLYDLLLEMLDA (SEQ ID NO:21) | 526–537 | zebra finch ER |
| PLYDLLLEMLDG (SEQ ID NO:22) | 350–361 | rainbow trout ER |
| PLYDLLLEMLDG (SEQ ID NO:23) | 461–472 | salmon ER |
| PLYDLLLEMLDA (SEQ ID NQ:24) | 527–538 | xenopus ER |
| PVYDLLLEMLNA (SEQ ID NO:25) | 433–444 | human ER-β |
| PVYDLLLEMLNA (SEQ ID NO:26) | 441–452 | rat ER-β |

TABLE 6-continued

HIGHLY CONSERVED REGIONS OF ERs FROM VARIOUS SPECIES

| Conserved Region | Amino Acid Position | Source |
| --- | --- | --- |
| EFPEMMSEVIAA (SEQ ID NO:27) | 904–915 | progesterone receptor |
| DFPEMMAEIISV (SEQ ID NO:28) | 889–900 | androgen receptor |
| EFPEMLAEIITN (SEQ ID NO:29) | 748–760 | glucocorticoid receptor |
| EFPAMLVEIISD (SEQ ID NO:30) | 955–966 | mineralocorticoid receptor |
| PMHKLFLEMLEA (SEQ ID NO:31) | 507–518 | ERR1 |

Sequence comparisons of the (a) AF2 alpha-helix region in ER from several species (modified from White et al., 1997); (b) ER-β; and (c) alignment of human nuclear receptor proteins, including progesterone receptor (PR), androgen receptor (AR), glucocorticoid receptor (GR), mineralocorticoid receptor (MR) and estrogen receptor related receptor (ERR1), as modified from Danielian et al. (1992). Conserved region is in boldface type.

In addition, this region, YDLLLEML (SEQ ID NO:32), is also found in the newly discovered estrogen receptor-s which has been reported to form functional dimers with the classical ER (Cowley et al., 1997). In contrast, the tyrosine residue found among estrogen receptor family members in this region is not conserved in other nuclear receptors, such as glucocorticoid receptor, progesterone receptor or androgen receptor. These sequence data suggest a strong likelihood for selectivity within the estrogen receptor family, with the exclusion of other nuclear hormone receptors.

To test the selectivity of antiestrogenic peptides, the inventor evaluated the effects of the peptides on growth of cancer cells in response to different hormonal stimuli. These in vitro data show that peptide antiestrogens are highly specific for ER-mediated growth (Table 7). MCF-7 cells that are rich in ER content show significant growth inhibition on treatment with pY-peptides after estrogen stimulation. In addition, the growth response of ZR75–1 and T47D breast cancer cells to estradiol-17β is inhibited by pY-peptide antiestrogen. However, T47D human breast cancer cells also have a high content of progesterone receptor and are known to show a growth response to medroxyprogesterone when grown in vitro in the absence of estrogen (Shi et al., 1994). This growth response to progesterone is not affected by the pY-peptide antiestrogens. Further, LNCaP human prostate cancer cells respond to androgen stimulation with growth in vitro (Shuurman et al., 1991), and this androgenic effect is not altered by prior treatment with peptide antiestrogens. These data suggest that the peptide antiestrogens disclosed herein are very selective in their mode of growth inhibition. Growth-stimulatory effects of estrogen, but not androgen or progestogens, are blocked by the UCLA peptide antiestrogens. Alternative signaling motifs that may influence the biologic activity of other nuclear hormone receptors (e.g., leucine repeats) (Turner and Tijan, 1989) are not affected by the pY-peptide sequence.

TABLE 7

PHOSPHOTYROSYL-PEPTIDES MODELED FROM ER SPECIFICALLY INHIBIT ESTROGEN-INDUCED GROWTH OF HUMAN BREAST CANCER CELLS IN VITRO*

| Cancer Cell | Growth Stimulus | Growth Inhibition (%) |
| --- | --- | --- |
| MCF-7 | Estradiol-17β | 96.7 ± 3.3 |
| ZR75-1 | Estradiol-17β | 90.2 ± 4.5 |
| T47D | Estradiol-17β | 90.1 ± 4.5 |
| T47D | Medroxyprogesterone | 5.5 ± 2.5 |
| LNCaP | Androgen | 0.0 ± 0.0 |

*pY-peptide (approx. 500 μM) was delivered in cationic liposomes to cultures of human cancer cells growing in the presence of different growth stimuli, including either estradiol-17β, medroxyprogesterone or androgen (see growth stimulus column). Breast cancer cells included MCF-7, ZR75-1, and T47D, while prostate cancer cells were LNCaP cell lines. All cells were incubated in phenol red-free media, with dextran-coated charcoal-treated serum at 0.1% to assure minimal to no steroid contamination (Shi et al., 1994). After 4 days stimulation with 1 nM estradiol, 10 nM medroxyprogesterone or 1 nM androgen, growth was quantitated in cultures treated with pY-peptide and expressed relative to that of controls exposed to blank liposomes (given as % growth inhibition). Results of three experiments are shown with mean ± SEM shown.

The growth response of MCF-7 breast cancer cells to estrogen and to malonyltyrosyl-peptides was also evaluated in vivo (Pietras et al., 1995). Malonyltyrosyl-peptideswere free or encapsulated in liposomes and delivered by intraperitoneal injection using established methods. The malonyltyrosyl-peptides show significant antitumor activity in blocking the growth of human breast cancer cell xenografts in vivo ($P<0.01$), with greater growth inhibition from liposome-encapsulated peptide (FIG. 8B).

In order to evaluate alternate strategies for more efficient delivery of peptides, the inventor prepared a phosphotyrosyl-octapeptide antiestrogen coupled with a short peptide internalization vector. The latter vector is a 16-amino acid sequence derived from the homeodomain of antennapedia, a Drosophilia transcription factor that translocates across biological membranes (Derossi et al., 1994; Bonfanti et al., 1997). This homeopeptide has been demonstrated to promote the internalization of polypeptides linked to its carboxy-terminus. Using the pY-tapeptide-internalization vector, the inventor found that nanomolar concentrations of the peptide have efficacy in the disruption of estrogen-induced growth of breast cancer cells (FIG. 9A and FIG. 9B).

The expected growth stimulation by estrogen is found after treatment of MCF-7 breast cancer cells with the internalization homeopeptide alone, exceeding the growth of control cells in the absence of estrogen by about 3-fold (FIG. 9A). Similarly, a low concentration of phosphotyrosyl-peptide alone in solution (25 μM) does not alter the growth response to estrogen (FIG. 9A). However, the peptide antiestrogen when coupled with the internalization peptide does suppress the expected growth effect of estrogen (FIG. 9A). A dose-response study shows that the antiestrogen-internalization peptide is effective in growth inhibition of MCF-7 breast cancer cells at concentrations less than 25 nanomolar.

5.4 Example 4

Peptide Antiestrogen Disrupt the Molecular Association Between ER and Steriod Reception Activator-1

Upon activation in vivo, estrogen receptors bind to their cognate DNA response elements and are thought to recruit co-activator proteins and general transcription factors to form an active complex for stimulation of gene expression. Steroid receptor co-activator-1 (SRC-1) is a co-activator protein (165 kDa) for estrogen receptor and is a member of a gene family that includes SRC-1, TIF2 (also termed GRIP-1 and SRC-2) and p/CIP (also termed RAC3, ACTR, AIB1 and SRC-3) (see Xu et al., 1998). Results from several studies indicate that SRC-1 mediates steroid hormone responses in vitro by promoting receptor-dependent tansactivation of genes (Onate et al., 1995; Heery et al., 1997). In addition, disruption of the SRC-1 gene appears to result in partial resistance to hormone (Xu et al., 1998). Short sequence motifs in SRC-1 and other co-activators appear necessary to mediate the binding of these proteins to nuclear receptor (Heery et al., 1997). Although the simple motif, LXXLLL (where L=leucine and X=any amino acid) (SEQ ID NO:33) and called an NR Box, was initially thought to be sufficient for binding of steroid receptors, more recent work suggests that the receptor-binding domains of steroid receptor co-activators are far more complex (Ding et al., 1998).

In order to assess the effect of peptide antiestrogens on the interaction between ER and SRC-1, MCF-7 breast cancer cells were treated in vitro with or without 1 nM estradiol-17β, and cell lysates were prepared for immunoprecipitation with antibody to ER, followed by gel electrophoresis and immuno-blotting with antibody to SRC-1, using established methods (Pietras et al., 1995). In the absence of peptide antiestrogens, SRC-1 and ER form a binding complex beginning at 15 min after estrogen treatment, and the association is maximal by 60 min. Prior incubation of breast cells with pY8-peptide or Int-pY8-peptide interferes with ER/SRC-1 binding (Table 8). Similarly, in parallel studies, growth of the MCF-7 breast cancer cells is suppressed by treatment with the active pY8-peptide antiestrogens (Table 8). In contrast pre-treatment of MCF-7 breast cancer cells with conY-peptide (lacking phosphorylation of Tyr537) or with pY8AA-peptide (substitution of alanine amino acid residues for leucines at position 539–540) elicits no effect on ER/SRC-1 binding or on cell growth in vitro (Table 8), The latter data further suggest that Tyr537 as well as neighboring leucine residues in ER may be important in the ER/SRC-I interaction and in the growth regulation of human breast cancer cells.

Using an alternate strategy to evaluate ER/SRC-1 binding, a peptide mimic was prepared using sequence derived from NR Box III, LLRYLLDK, in SRC-1 (SEQ ID NO:39) (Onate et al., 1995; Ding et al., 1998). Prior treatrnent of MCF-7 breast cells with LLRYLLDK-peptide (SEQ ID NO:39) blocks ER/SRC-1 binding at 60 min and also suppresses breast cancer cell growth in vitro. Thus, these results suggest that pharmacologic manipulation of the binding of nuclear receptor co-factors may offer another novel antiestrogen approach in the treatment of human breast cancer.

TABLE 8

BIOLOGIC PROPERTIES OF SYNTHETIC PEPTIDE ANTIESTROGENS BASED ON ER AMINO ACID SEQUENCE SURROUNDING TYR537, STEROID RECEPTOR CO-ACTIVATOR-1 AMINO ACID SEQUENCE SURROUNDING TYROSINE FROM NR BOX III AND CONTROL PEPTIDES

| Peptide | Amino Acid Sequence | SEQ ID NO: | ER/SRC-1 Binding | MCF-7 Cell Growth |
| --- | --- | --- | --- | --- |
| Estrogen Receptor Mimetic | | | | |
| Int-pY8 | RQIKIWFQNRRMKWKKPLpYDLLLE | 34 | Decreased | Decreased |
| Int | RQIKIWFQNRRMKWKK | 35 | No Effect | No Effect |
| pY8 | PLpYDLLLE | 2 | Decreased | Decreased |
| conY | PLYDLLLE | 1 | No Effect | No Effect |
| pY8AA | PLpYDAALE | 38 | No Effect | No Effect |
| Steroid Receptor Coactivator-1 Mimetics | | | | |
| LLRYLLDK | LLRYLLDK | 39 | Decreased | Decreased |

The table shows the amino acid sequence of several peptides synthesized for use in these studies. Among the estrogen receptor (ER)-mimetic peptides, pY8 represents the octapeptide from amino acid 535–542 in ER, with phosphorylation (p) of tyrosine. Int-pY8 is the pY8 peptide synthesized with the peptide internalization sequence from antennapedia (Derossi et al., 1994). The peptide, pY8AA is a control peptide for pY8, with alterations in leucines at positions 539–540. The steroid receptor coactivator-1 (SRC-1) peptide mimetic is based on the sequence surrounding tyrosine in NR Box III (see Ding et al., 1998). All peptides, except Int-pY8 and Int, were encapsulated in cationic liposomes for delivery to MCF-7 breast cancer cell cultures in vitro at 50 μM. Int-pY8 and Int were delivered in vitro at 25 μM. The molecular association between ER and SRC-1 proteins (ER/SRC-1 binding) at 50 min after treatment of MCF-7 cells with 1 nM estradiol-17β was determined by Western immunoblot analysis using established methods (Pietras et al., 1995); results are given with reference to appropriate controls. For comparison with results from Western blot analysis, in vitro growth of MCF-7 breast cancer cells was assessed 72 h after treatment with 1 nM estradiol alone or in combination with the peptides listed in the table; results are expressed relative to appropriate controls (Pietras et al., 1995).

5.5

Example 5

Synthesis and Purification of Peptides

In one aspect, the peptides of the present invention may be synthetically prepared using methods known to those of skill in the art Once such method involves the synthesis of peptides using an Advanced ChemTech MPS 396 peptide synthesizer (Louisville, Ky.) using Fmoc (Chang and Meienhofer, 1978) or Boc chemistry (Erickson and Merrifield, 1976). Such peptides may be purified from the crude preparations by reverse-phase high performance liquid chromatography (HPLC) using a preparative scale C18 column (Vydac 218TP510; The Separation Group, Hesparia, Calif.) and a Waters 625 LC HPLC system (Milford, Mass.) using the methods previously described (Hancock, 1984). A suitable aqueous buffer useful for the purification (Buffer A) consists of 0.11% (vol./vol.) phosphoric acid, 0.28% (vol./vol.) triethylamine, and 0.25 mM EDTA, pH 6.5. A suitable organic buffer (Buffer B) consists of 15% (vol./vol.) of Buffer A in acetonitrile. After reverse-phase chromatography, fractions containing peptide are dialyzed extensively against 50 mM ammonium bicarbonate and lyophilized. These fractions are analyzed for purity by reverse-phase chromatography on an analytical C18 column (Vydac 218TP546). For this purpose, Buffer C may consist of 0.1% (vol./vol.) trifluoroacetic acid (TFA) in water, and Buffer D, 0.1% (vol./vol.) TFA in 90% (vol./vol.) acetonitrile. A gradient of up to 80% Buffer E may be used to elute the peptides, which can then be subsequently dried by roto-evaporation and submitted for either N-terminal sequence analysis or amino acid composition analysis.

5.6 Example 6

Means for Preparing Site-Directed Mutagenized Peptides

In certain embodiments, the peptides of the present invention may be prepared by recombinant DNA methodologies which are known to those of skill in the art. Nucleic acid segments encoding the particular peptides may be subjected to site directed mutagenesis to prepare peptide variants as described above. One preferred method for the mutagenesis of short peptides is the PCR™-based strand overlap extension (SOE) (Ho et al., 1989) method. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCRT products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into *E. coli* JM101, XL1-Blue™ (Stratagene, LaJolla, Calif.), JM105, or TG1 (Carter et al., 1985) cells. Clones are isolated and the mutations are confirmed by sequencing of the isolatedplasmids.

5.7 Example 7

Means for Expressing Recombinant Peptides

A particular aspect of the present invention is the production of recombinant proteins in large quantity. Such methods are well-known to those of skill in the art, and have been described in detail hereinabove. To overexpress the syntheticaly-modified peptide derivatives of the present invention, DNA fragments encoding the peptides may be cloned into appropriate expression vectors. Such vectors may contain a multiple restriction enzyme cloning site that situates the nucleic acid segment of interest such that its expression is controlled from an inducible promoter. Methods for determining orientation of the inserted segment, induction of the promoter, growth conditions, and restriction enzyme analysis, and recovery of the produced protein are well-known to those of skill in the arL Expression and quantitation of the peptides are determinable via standard methods such as SDS-PAGE, Western blot analysis, and protein determination assays.

In an overall and general sense, the production of a large number of recombinant proteins may be produced in either prokaryotic or eukaryotic cells using various expression systems depending upon the particular construct, and the particular advantages of the various expression systems available for such protein production. Particular aspects of the present invention include the use of the following expression systems:

5.7.1 pQE™ pQE™ (Qiagen Inc., Chatsworth, Calif.) which results in the production of a fusion protein where the 10–25 amino acid long carrier contains six contiguous histidine residues. The $His_6$ sequence allows the rapid purification on a column of iminodacetic acid derivatied Sepharose 6B Fast Flow chelated with $Ni^+$ ions. This system is a very effective expression system for preparing peptide compositions generating up to 50 mg of pure recombinant protein per liter of *E. coli* culture. Overnight cultures of *E. coli* XL1-Blue™ (Stratagene) harboring the recombinant plasmids may be diluted 1:50 in 1 l of Luria broth (GIBCO BRL) containing 50 mglml ampicillin. *E. coli* cells are grown until the culture reached an $OD_{600}$ of 0.5–0.8. Expression of the recombinant proteins may then be induced by adding IPTG to a final concentration of 0.2 mM. After a three hour induction period, cells may be collected by centrifugation, resuspended in 15 ml of Buffer A (5 mM imidazole, 0.5 M NaCl, 20 mM Tris-HCI, pH 7.9) and lysed by passage through a French press twice at 20,000 lb./$m^2$. Cell debris is easily removed by centrifugation at 50,000×g for 10 min, with the supernatant being passed through a 0.45 :M filter. The recombinant proteins can then be purified by affinity chromatography using a suitable medium.

5.7.2 pGEX™ pGEX™ (Pharmacia, Ltd. Piscataway, N.J.) encodes a fusion protein where the carrier glutathione-S-transferase allows one-step purification on a column of glutathione-Sepharose (Smith and Johnson, 1988). This system has the advantage of producing peptides which effectively bind to microtiterplates or nitrocellulose membranes used in ELISA or Western blot type assays. In these cases, the pGEX™ system which generates fusion proteins with a longer carrier protein is a useful alternative expression system. Another advantage of this system, is the availability of selective proteolytic cleavage sites which have been introduced just C-terminal of the carrier, to allow removal of the peptide from the carrier protein once synthesized.

5.7.3 pMAL™ pMAL™ (New England Biolabs, Beverly Mass.) encodes a fusion protein with the maltose binding protein which again permits quick affinity purification according to the following procedure: The gene of interest is cloned into the pMAL™-p2vector (New England Biolabs, Beverly, Mass.)

downstream and inframe with the malE signal sequence and gene, which encodes a maltose-binding protein (MBP). The recombinant plasmid is transformed into E. coli and the culture is induced to overproduce the MBP-fusion protein by the addition of IPTG to the culture medium. The MBP-fusion protein can then be purified as described by (Riggs et al., 1992; Maina et al., 1988). Because of the carrier, the expressed fusion protein is transported to the periplasmic space where disulfide bonds can be formed.

5.7.4 pBVL™ pBVL™ (PharMingen, San Diego, Calif.) which may be used in conjunction with Baculo Gold™ system to transfect insect cells and produce reasonable levels (1–3 mg/l) of recombinant protein in eukaryotic cells.

5.7.5 Bacterial Hosts

Recombinant proteins so prepared find utility in the present invention in a variety of embodiments, including compositions for immunoassay reagents, antigen preparation for generation of immune responses in susceptible animals, vaccine formulations, and substrates for antibody production for use in passive and active immunization methods. For large-scale preparation of recombinant proteins, the following procedures may be used: Saturated overnight cultures of E. coli JM101 supE, endA, sbcB15, hsd R4, rpsL, thi)(lac-proAB) (F'traD36 proAB$^+$ lac$^q$ Z)M15), E. coli JM105 supE thi)(lac-proAB) (F'traD36 proAB$^+$ lac$^q$ ZM15), TG1 (supE hsd)5 thi)(lac-proAB)$^+$ (F$^+$traD36 proAB lac$^q$ lacZ)M15)) (Carter et al., 1985), or XL1-Blue™ cells (Stratagene, La Jolla, Calif.) harboring expression plasmids are diluted 1:50 in Luria Broth (GIBCO BRL, Grand Island, N.Y.) supplemented with ampicillin and allowed to grow until the culture reached an OD$_{600}$ of 0.6–0.7. Isopropyl-1-thip-β-galactopyranoside(IPTG; Gibco BRL, Grand Island, N.Y.) (final concentration 0.2 mM) is added to the cells and growth continued for another 2.5–5 hr at 37° C. The bacteria are collected by centriflgation and the bacterial pellets are resuspended in phosphate buffered saline (PBS; 10 MM phosphate, 0.14 M NaCI, pH 7.4). The cells are lysed by passage through a French press (SLM Instrument Inc., Urbana, Ill.) twice at 20,000 lb/in$^2$. The bacterial lysate is centrifuged at 102,000×g for 10 min to remove bacterial debris. The supernatant containing the soluble proteins is filtered through a 0.45 μM membrane (Nalgene, Rochester, N.Y.) and retained for further purification.

5.8 Example 8

Preparation of Antibody Compositions

The synthetic peptides and recombinant peptides described above may be used in the generation of an immune response in an animal and the preparation of antibodies specific for these epitopes. The preparation of antibodies is well known to those of skill in the art as described hereinabove. Briefly, the novel peptides of the present invention may be used as antigens in the following manner:

Each peptide may be coupled to keyhole limpet hemocyanin (KLH) and used to subcutaneously immunize BALB/c mice. Initial injections contain 250 pg protein and the mice are boosted 7 weeks later with 250 μg of the respective KLH-coupled peptide and then bled 1 week later. The polyclonal antibodies produced by the injected mice are tested for their ability to recognize the peptide antigen in an ELISA assay. The Abs are also assayed for their ability to inhibit ER-ERE dimerization.

2 mg of KLH is reconstituted with 200 μl of deionized water. 2 mg of the peptide is dissolved in 0.5 ml of conjugation buffer (Pierce Chemical Co., Rockford, Ill.). 500 μl of the peptide solution is added to 200 μl carrier protein solution followed by the addition of 0.5 mg 1-ethyl-3-(3-dimethylaminopropyl) carbodiimide (EDC) in 50 μl of water. The mixtures are incubated at room temperature for 2 hours by end-over-end mixing. The contents of one bottle of the purification buffer salts is dissolved in 60 ml degassed, deionized water. The desalting column is washed with 5 ml of purification buffer, and the peptide carrier mixture is applied directly to the top of the column. 0.5 ml aliquots of wash buffer are added to the column and each fraction is collected in a separate tube. The KLH conjugated peptide are present in the first or second fraction from the column.

6.0 REFERENCES

The following literature citations as well as those cited above are incorporated in pertinent part by reference herein for the reasons cited in the above text:

U.S. Pat. No. 3,791,932, issued Feb. 12, 1974.
U.S. Pat. No. 3,817,837, issued Jun. 18, 1974.
U.S. Pat. No. 3,850,752, issued Nov. 26, 1974.
U.S. Pat. No. 3,939,350, issued Feb. 17, 1976.
U.S. Pat. No. 3,949,064, issued Apr. 6, 1976.
U.S. Pat. No. 3,996,345, issued Dec. 7, 1976.
U.S. Pat. No. 4,174,384, issued Nov. 13, 1979.
U.S. Pat. No. 4,196,265, issued Apr. 1, 1980.
U.S. Pat. No. 4,271,147, issued Jun. 2, 1981.
U.S. Pat. No. 4,275,149, issued Jun. 23, 1981.
U.S. Pat. No. 4,277,437, issued Jul. 7, 1981.
U.S. Pat. No. 4,366,241, issued Dec. 28, 1982.
U.S. Pat. No. 4,472,509, issued Sep. 18, 1984.
U.S. Pat. No. 4,536,387, issued Aug. 20, 1985.
U.S. Pat. No. 4,554,101, issued Nov. 19, 1985.
U.S. Pat. No. 4,578,770, issued Mar. 25, 1986.
U.S. Pat. No. 4,596,792, issued Jun. 24, 1986.
U.S. Pat. No. 4,599,230, issued Jul. 8, 1986.
U.S. Pat. No. 4,599,231, issued Jul. 8, 1986.
U.S. Pat. No. 4,601,903, issued Jul. 22, 1986.
U.S. Pat. No. 4,608,251, issued Aug. 26, 1986.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 5,021,236, issued Jun. 4, 1991.
U.S. Pat. No. 5,279,721, issued Jan. 18, 1994.
Int. Pat. Appl. Publ. No. WO 87/00880.
Int. Pat. Appl. Publ. No. WO 88/10315.
Int. Pat. Appl. Publ. No. WO 89/06700.
Int. Pat. Appl. Publ. No. WO 90/07641.
Intl. Pat. Appl. Publ. No. PCT/US87/00880.
Eur. Pat. Appl. Publ. No. EP 329,822.
Great Britain Pat. Appl. Publ. No. GB 2,202,328.
Adnane, Guadray, Simon, Simony-Lafontaine, Jeanteur, Theillet, "Proto-oncogene amplification and human breast tumor phenotype," Oncogene, 4(11):1389–1395, 1989.
Ahrens et al., "Overproduction of full-length and truncated human estrogen receptors in Escherichia coli," Receptor, 2(2):77–92, 1992.
Allen and Choun, "Large Unilamellar Liposomes with Low Uptake into the Reticuloendothelial System," FEBS Lett., 223:4246,1987.
Allen, Gerlach, Clegg, "Nucleotide sequence and fumctions of mrk determinants necessary for expression of type 3 fimbriae in Klebsiella pneumoniae," J. Bacteriol., 173(2):916–920, 1991.
Arnold and Notides, "An antiestrogen: a phosphotyrosyl peptide that blocks dimerization of the human estrogen receptor," Proc. Natl. Acad Sci. USA, 92:7475–7479, 1995.

Arnold, Obourn, Jaffe, Notides, "Phosphorylation of the human estrogen receptor by nitogen-activated protein kinase and casein kinase II," *J. Steroid Biochem., Mol. Biol.*, 55:163–172, 1995.

Arnold, Obourn, Jaffe, Notides, "Serine 167 is the major estadiol-induced phosphorylation site on the human estrogen receptor," *Mol. Endocrinol*, 8(9):1208–1214, 1994.

Arnold, Obourn, Jaffe, Notides, "Phosphorylation of the human estrogen receptor on tyrosine 537 in vivo and by src family tyrosine kinases in vitro," *Mol. Endocrinol*, 9(1):24–33, 1995.

Arnold, Vorojeikina, Notides, "Phosphorylation of tyrosine 537 on the human estrogen receptor is required for binding to an estrogen response element," *J. Biol. Chem.*, 270:30205–30212, 1995.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Balazsovits, Mayer, Bally, Cullis, McDonell, Ginsberg, Falk, "Analysis of the effect of liposome encapsulation on the vesicant properties, acute and cardiac toxicities, and antitumor efficacy of doxorubicin," *Cancer Chemother. Pharmacol.*, 23(2):81–86, 1989.

Barany and Merrifield, "A chromatographic method for the quantitative analysis of the deprotection of dithiasuccinoyl (Dts) amino acids," *Ana. Biochem.*, 95(1):160–170, 1979.

Benvenisty and Neshif, "Direction introduction of genes into rats and expression of the genes," *Proc. Nall. Acad Sci. USA*, 83:9551–9555, 1986.

Benz, Scott, Sarup, Johnson, Tripathy, Coronado, Shepard, Osborne, "Estrogen-dependent, tamoxifen-resistant tumorigenic growth of MCF-7 cells transfected with HER2/neu," *Breast Cancer Res. Treat.*, 24(2):85–95, 1993.

Beug and Graf, "Co-operation between viral oncogenes in avian erythroid and myeloid leukaemia," *Eur. J. Clin. Invest.*, 19(6):491–502, 1989.

Bonfanti, Tavema, Salmona, D'Incalci, Broggini, "p21WAF1-derived peptides linked to an internalization peptide inhibit human cancer cell growth," *Cancer Res.*, 57(8):1442–1446, 1997.

Borg, Baldetorp, Femo, Killander, Olsson, Ryden, Sigurdsson, "ERBB2 amplification is associated with tamoxifen resistance in steroid-receptor positive breast cancer," *Cancer Lett.*, 81(2):137–144, 1994.

Campbell, "Monoclonal Antibody Technology, Laboratory Techniques in Biochemistry and Molecular Biology," Burden and Von Knippenberg, Eds., Elsevier, Amsterdam, 13:75–83, 1984.

Capaldi et al., "Changes in order of migration of polypeptides in complex III and cytochrome C oxidase under different conditions of SDS polyacrylamide gel electrophoresis," *Biochem. Biophys. Res. Commun.*, 74(2):425433, 1977.

Capaldi et al., "Isolation of a major hydrophobic protein of the mitrochondrial inner membrane," *Biochem. Biophys. Res. Commun.*, 55(3):655–659, 1973.

Capaldi R. A., "Identification of the major enzymic activities of the mitochondrial inner membrane in terms of their migration in sodium dodecyl sulfate polyacrylamide gel electrophoresis," *Aech. Biochem. Biophys.*, 163(1):99–105, 1974.

Capecchi, "High efficiency transformation by direct microinjection of DNA into cultured mammalian cells," *Cell*, 22(2):479–488, 1980.

Carraway and Canfley, "A neu acquaintance for erbB3 and erbB4: a role for receptor heterodimerization in growth signaling," *Cell*, 78(1):5–8, 1994.

Carret, Emonard, Fardel, Druguet, Herbage, Flandrois, "Gelatin and collagen binding to Staphylococcusaureus sains," *Ann. Inst. Pasteur Microbiol.*, 136A(2):241–245, 1985.

Carter, Bedouelle, Winter, "Improved oligonucleotide site-directed mutagenesis using M13 vectors," *Nucl. Acids Res.*, 13(12):4431 1443,1985.

Castoria Migliaccio, Green, Domenico, Chambon, "Properties of a purified estradiol-dependent calf uterus tyrosine kinase," *Biochemistry*, 32:1740–1750, 1993.

Coffin, "Retroviridae and their replication," In: Fields BN, Knipe DM, ed. Virology. New York: Raven Press, pp. 1437–1500, 1990.

Chen and Okayama, "High-efficiency transfection of mammalian cells by plasmid DNA," *Mol. Cell Biol.*, 7:2745–2752, 1987.

China, Sory, N'Guyen, De Bruyere, Cornelis, "Role of the YadA protein in prevention of opsonization of Yersinia enterocolitica by C3b molecules," *Infect. Immun.*, 61(8):3129–3136,1993.

Chou and Fasman, "Conformational Parameters for Amino Acids in Helical, β-Sheet, and Random Coil Regions Calculated from Proteins," *Biochemistry*, 13(2):211–222, 1974b.

Chou and Fasman, "Prediction of Protein Conformation," *Biochem.*, 13(2):222–245,1974a.

Chou and Fasman, "Empirical Predictions of Protein Conformation," *Ann. Rev. Biochem.*, 47:251–276,1978b.

Chou and Fasman, "Predictionof FTurns," *Biophys. J.*, 26:367–384,1979.

Clapp, "Somatic gene therapy into hematopoietic cells. Current status and future implications," *Clin. Perinatol.*, 20(1):155–168,1993.

Cohen, Ren, Baltimore, "Modular binding domains in signal transduction proteins," *Cell*, 80:237–248, 1995.

Cole, Dalziel, Leitl, "Treatment of acute osteomyelitis in childhood," *J. Bone and Joint Surg. [Br]*, 64(2):218–223, 1982.

Coune, "Liposomes as drug delivery system in the treatment of infectious deseases: potential applications and clinical experience," *Infection*, 16(3):141–147, 1988.

Coupar et al., "A general method for the construction of recombinant vaccinia virus expressing multiple foreign genes," *Gene*, Vol 68:1–10, 1988.

Couvreur, Tulkens, Roland, Trouet, Speiser, "Nanocapsules, a new type of lysosomotropic carrier," *FEBSLett.*, 84(2):323–326,1977.

Couvreur, "Polyalkyleyanoacrylatesas Colloidal Drug Carriers," *Crit. Rev. Ther. Drug Carrier Syst.*, 5:1–20, 1988.

Cowley, Hoare, Mosselman, Parker, "Estrogen receptors alpha and beta form heterodimers on DNA," *J. Biol. Chem.*, 272(32):19858–19862, 1997.

Cox, Zamb, Babiuk, "Bovine herpesvirus 1: immune responses in mice and cattle injected with plasmid DNA," *J. Virol.*, 67(9):5664–5667,1993.

Curiel, Agarwal, Wagner, Cotten, "Adenovirus enhancement of transferrin-polylysine-mediated gene delivery," *Proc. Natl. Acad Sci. USA*, 88(19):8850–8854,1991.

Daly, "SH2 domain-containing signaling proteins in human breast cancer," *Breast Cancer Res. Treat.*, 34(1):85–92, 1995.

Danielian, White, Lees, Parker, "Identification of a conserved region required for hormone dependent transcriptional activation by steroid hormone receptors," *EMBO J.*, 11:1025–1033, 1992.

Denner, Weigel, Schrader, O'Malley, "Hormone-dependent regulation of chicken progesterone receptor deoxyribonucleic acid binding and phosphorylation," *Endocrinol*, 125(6):3051–3058, 1989.

Denton, Koszewski, Notides, "Estrogen receptor phosphorylation. Hormonal dependence and consequence on specific DNA binding," *J. Biol Chem.*, 267(11):7263–7268, 1992.

Derossi, Joliot, Chassaing, Prochiantz "The third helix of the antennapedia homeodomain translocates through biological membranes," *J. Biol Chem*, 269: 10444–10450, 1994.

Ding, Anderson, Ma, Hong, Uht, Kushner, Stallcup "Nuclear receptor-binding sites of coactivators glucocorticoid receptor interacting protein 1 (GRIP1) and steroid receptor coactivator 1 (SRC-1): Multiple motifs with different binding specificities," *Mol. Endocrinol*, 12:302–312, 1998.

Dougall, Quian, Peterson, Miller, Samanta, Greene, "The neu-oncogene: signal transduction pathways, transformation mechanisms and evolving therapies," *Oncogene*, 9(8):2109–2123, 1994.

Dubensky et al., "Direct transfection of viral and plasmid DNA into the liver or spleen of mice," *Proc. Natl Acad Sci. USA*, 81:7529–7533, 1984.

Eglitis and Anderson, "Retroviral vectors for introduction of genes into mammalian cells," *Biotechniques*, 6(7):608–614, 1988.

Eglitis, Kantoff, Kohn, Karson, Moen, Lothrop, Blaese, Anderson, "Retroviral-mediated gene transfer into hemopoietic cells," *Avd. Exp. Med. Biol.*, 241:19–27, 1988.

Elledge, Clark, Chamness, Osborne, *J. Natl. Cancer Inst.*, 86:705–711, 1994.

Ernst, Parker, Rodan, "Functional estrogen receptors in osteoblastic cells demonstrated by transfection with a reporter gene containing an estrogen response element," *Mol. Endocrinol.*, 5:1597–1605, 1991.

Evans, "The steroid and thyroid hormone receptor superfamily," *Science*, 240(4854):889–895, 1988.

Faller and Baltimore, "Liposome encapsulation of retrovirus allows efficient super infection of resistant cell lines," *J. virol*, 49(1):269–272, 1984.

Fawell, Lees, White, Parker, "Characterization and colocalization of steroid binding and dimerization activities in the mouse estrogen receptor," *Cell*, 60(6):953–962, 1990.

Fechheimer et al., "Transfection of mammalian cells with plasmid DNA by scrape loading and sonication loading," *Proc. Natl. Acad Sci. USA*, 84:8463–8467, 1987.

Ferkol et al., *FASEB J.*, 7:1081–1091, 1993.

Fields, Lovdahl, Miles, Hagen, Fields, "Solid-phase synthesis and stability of triple-helical peptides incorporating-native collagen sequences," *Biopolymers*, 33(11):1695–1707,1993.

Fiers, Contreras, Haegemann, Rogiers, Van de Voorde, Van Heuverswyn, Van Herreweghe, Volckaert, Ysebaert, "Complete nucleotide sequence of SV40 DNA," *Nature*, 273(5658):113–120,1978.

Forman, Yang, Au, Casanova, Ghysdael, Samuels, "A domain containing leucine-zipper-like motifs mediate novel in vivo interactions between the thyroid hormone and retinoic acid receptors," *Mol. Endocrinol*, 3(10):1610–1626, 1989.

Freifelder, "Studies on *Escherichia coli* sex factors. III. Covalently closed F'Lac DNA molecules," *J. Mol. Biol.*, 34(1):31–38, l968a Freifelder, "Studies on *Escherichia coli* sex factors. IV. Molecular weights of the DNA of Several F' Elements," *J. Mol. Biol*, 35(1):95–102, 1968b.

Freifelder and Better, "Dialysis of small samples in agarose gels," *Anal Biochem.*, 123(1): 83–85, 1982.

Freifelder and Freifelder, "Studies on *Escherichia coil* sex factors. I. Specific labeling of F'Lac DNA," *J. Mol. Biol*, 32(l):15–23, 1968a.

Freifelder and Freifelder, "Studies on *Escherichia coli* sex factors. II. Some physical properties of F'Lac and F DNA," *J. Mol. Biol.*, 32(1):25–35, 1968b.

Freshner, R. I. "Animal Cell Culture: a Practical Approach", Second Edition, Oxford/New York, IRL Press, Oxford University Press, 1992.

Friedmann, "Progress toward human gene therapy," *Science*, 244:1275–1281, 1989.

Fromm, Taylor, Walbot, "Expression of genes transferred into monocot and dicot plant cells by electroporation," *Proc. Natl. Acad Sci. USA*, 82(17):5824–5828,1985.

Fraley et al., "Entrapment of a bacterial plasmid in phospholipid vesicles: Potential for gene transfer," *Proc. Natl. Acad. Sci. USA*, 76:3348–3352, 1979.

Frohman, M. A., In "PCR Protocols: A Guide to Methods and Applications," Academic Press, New York, 1990.

Fynan, Webster, Fuller, Haynes, Santoro, Robinson, "DNA vaccines: protective immunizations by parenteral, mucosal, and gene-gun inoculations," *Proc. Natl. Acad Sci USA*, 90(24):11478–11482,1993.

Gabizon and Papahadjopoulos, "Liposomes formulations with prolonged circulation time in blood and enhanced uptake by tumors," *Proc. Natl. Acad. Sci USA*, 85:6949–6953,1988.

Ghosh-Choudhury, G., Y. Haj-Ahmad, and F. L. Graham, "Protein IX, a minor component of the human adenovirus capsid, is essential for the packaging of full-length genomes," *EMBO J.*, 6:1733–1739, 1987.

Gilmer, Pacofsky, Dorsey, Crosby, Alligood, Luttrell, Bradshaw, Miller, LeRay, Onori, Miller, Rusnak, Tian, Emerson, Knight, *Proc. Am Assoc. Cancer Res.*, 38:658–659, 1997.

Goding, In: *Monoclonal Antibodies: Principles and Practice*, 2nd Edition, Academic Press, Orlando, Fla., pp. 6074,1986.

Goeddel, Heyneker, Hozumi, Arentzen, Itakra, Yansura, Ross, Miozzari, Crea, Seeburg, "Direct expression in *Escherichia coli* of a DNA sequence coding for human growth hormone," *Nature*, 281(5732):544–548,1979.

Goeddel, Shepard, Yelverton, Leung, Crea, Sloma, Pestka, "Synthesis of human fibroblast interferon by *E. coli*," Nucl. Acids Res., 8(18):4057–4074,1980.

Goldenberg, "Infectious arthritis complicating rheumatoid arthritis and other chronic rheumatic disorders," *Arthritis Rheum.*, 32(4):496–502,1989.

Gomez-Foix, A. M., W. S. Coats, S. Baque, T. Alarn, R. D. Gerard, and C. B. Newgard, "Adenovirus-mediated transfer of the muscle glycogen phosphorylase gene into hepatocytes confers altered regulation of glycogen," *J. Biol. Chem.* 267:25129–25134, 1992.

Gopal, "Gene transfer method for transient gene expression, stable transfection, and cotransfection of suspension cell cultures," *Mol. Cell Biol.*, 5:1188–1190, 1985.

Graham et al., "Characteristics of a human cell line transformed by DNA from human adenovirus type 5", *J. Gen. Virol.*, 36:59–72, 1977.

Graham and Prevec, "Manipulation of adenovirus vector," In: E. J. Murray (ed.), Methods in Molecular Biology: Gene Transfer and Expression Protocol, Clifton, N.J.: Humana Press, 7:109–128, 1991.

Graham and Prevec, "Adenovirus-based expression vectors and recombinant vaccines," *Biotechnology*, 20:363–390, 1992.

Graham, F. L., and van der Eb, A. J., "Transformation of rat cells by DNA of human adenovirus 5," Virology 54(2):536–539, 1973.

Granfors, Viljanen, Tiilikainen, Toivanen, "Persistence of IgM, IgG, and IgA antibodies to Yersiniain yersiniaarthritis," *J. Infect Dis.*, 141(4):424–429,1980.

Granfors, Jalkanen, von Essen, Lahesmaa-Rantala, Isomaki, Pekkola-Heino, Merilahti-Palo, Saario, Isomaki, Toivanen, "Yersinia antigens in synovial-fluid cells from patients with reactive arthritis," *N. Engl. J. Med.*, 320(4):216–221, 1989.

Green and Chambon, "Nuclear receptors enhance the inventors' understanding of transcription regulation," *Trends Genet.*, 4:309–313, 1988.

Green et al., "Human oestrogen receptor cDNA: sequence, expression and homology to v-erb-A," *Nature*, 320:134–139, 1986.

Greene et al., "Sequence and expression of human estrogen receptor complementary DNA," *Science*, 231:1150–1154, 1986.

Grunhaus and Horwitz, "Adenovirus as cloning vector," *Seminar in Virology*, 3:237–252, 1992.

Guerrier-Takada et al., *Cell*, 35:849, 1983.

Harland and Weintraub, "Translation of mammalian MnRNA injected into Xenopus oocytes is specifically inhibited by antisense RNA," *J. Cell Biol.*, 101:1094–1099, 1985.

Harlow and Lane, In: *Antibodies: a Laboratory Manual*, Cold Spring Harbor Laboratory, Cold Spring Harbor, NY, 1988.

Harris, Lippman, Veronesi, Willett, "Breast cancer (3)," *N. Engl. J. Med.*, 327(7):473–480, 1992.

Hay, In: *Cell Biology of Etracellular Mairix*, New York, Plenum Press, 1991.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862(1):72–80, 1986.

Hedbom et al., "Interaction of a 59-kDa connective tissue matrix protein with collagen I and collagenII," *J. Biol Chem.*, 264(12):6898–6905,1989.

Heery, Kalkhoven, Hoare, Parker "A signature motif in transcriptional co-activators mediates binding to nuclear receptors," *Nature*, 387:733–736, 1997.

Henry-Michelland et al., "Attachment of Antibiotics to Nanoparticles; Preparation, Drug-Release and Antimicrobial Activity in vitro," *Int. J. Pham.*, 35:121–127, 1987.

Hermonat and Muzycska, "Use of adenoassociated virus as a mammalian DNA cloning vector: Transduction of neomycin resistance into mammalian tissue culture cells," *Proc. Natl. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Natl. Acad. Sci. USA*, 90:2812–2816, 1993.

Hess et al., *J. Adv. Enwne Reg.*, 7:149,1968.

Hirata, Kiuchi, Chen, Milbrandt, Guroff, "The phosphorylation and DNA binding of the DNA-binding domain of the orphan nuclear receptor NGFI-B," *J. Biol. Chem.*, 268(33):24808–24812, 1993.

Hitzeman, Clarke, Carbon, "Isolation and characterization of the yeast 3-phosphoglycerokinase gene (PGK) by an immunological screening technique," *J. Biol. Chem.*, 255(24):12073–12080,1980.

Ho and Su, "Therapy for septic arthritis," *J. Amer. Med. Assoc.*, 247(6):797–800,1982.

Ho et al., "Site-Directed Mutagenesis by Overlap Extension Using the Polymerase Chain Reaction," *Gene*, 77:51–59, 1989.

Hodel et al., *Acta Crystallogr.*, A48:851–858,1992.

Holderbaum et al., "Specific binding of colalgen to Staphylococcus aureus," *Collagen Rel. Res.*, 5(3):261–271,1985.

Holland et al., "Isolation and identification of yeast messenger ribonucleic acids coding for enolase, glyceraldehyde-3-phosphate dehydrogenase, and phosphoglycerate kinase," *Biochem.*, 17(23):49004907,1978.

Hornick et al., "Adherence to respiratory epithelia by recombinant *Escherichia coli* expressing Klebsiella pneumoniae type 3 fimbrial gene products," Infect. Immun, 60(4):1577–1588, 1992.

Horwich et al., "Synthesis of hepadnavirus particles that contain replication-defective duck hepatitis B virus genomes in cultured HuH7 cells," *J. Virol.*, 64:642–650, 1990.

Hou, Schindeler, Henzel, Ho, Brassner, McKnight, *Science*, 265:1701–1706, 1994.

Ignar-Trowbridge, Nelson, Bidwell, Curtis, Washburn, McLachlan, Korach, *Proc. Natl. Acad Sci USA*, 89:46584662, 1992.

Ingham, Brew, Migliorini, "Further localization of the gelatin-binding determinants within fibronectin. Active fragments devoid of type II homologous repeat modules," *J. Biol Chem.*, 264(29):16977–16980,1989.

Innis et al., "DNA sequencing with Thermus aquaticus DNA polymerase and direct sequencing of polymerase chain reaction-amplified DNA," *Proc. Nall. Acad. Sci USA*, 85(24):94369440, 1988.

Jacobs and Rubsamen, "Expression of pp60c-src protein kinase in adult and fetal human tissue: high activities in some sarcomas and mammary carcinomas," *Cancer Res.*, 43(4):1696–1702, 1983.

Jaiyesimi et al., "Use of tamoxifen for breast cancer: Twenty-eight years later," *J. Clin Oncol.*, 13:5 13–529, 1995.

Jameson and Wolf, "The antigenic index: a novel algorithm for predicting antigenic determinants," *Compu. Appl. Biosci*, 4(l):181–186,1988.

Johnson, "Why, when, and how biochemists should use least squares," *Anal. Biochem.*, 206(2):215–225,1992.

Jones et al., "Improved methods for binding protein models in electron density maps and the location of errors in these models," *Acda Cryst.*, 47(Pt. 2):110–119,1991.

Jones, *Genetics*, 85:12,1977.

Jones and Shenk, "Isolation of deletion and substitution mutants of adenovirus type 5, " *Cell*, 13:181–188, 1978.

Kaneda et al., "Increased expression of DNA cointroduced with nuclear protein in adult rat liver," *Science*, 243:375–378, 1989.

Kato et al., "Expression of hepatitis B virus surface antigen in adult rat liver," *J. Biol Chem.*, 266:3361–3364, 1991.

Kato et al., "Activation of the estrogen receptor through phosphorylation by mitogen-activated protein kinase," *Science*, 270(5241):1491–1494, 1995.

Katz, Reginato, Lazar, ° Functional regulation of thyroid hormone receptor variant TR alpha 2 by phosphorylation," *Mol. Cell. Biol.*, 15(5):2341–2348, 1995.

Katzenellenbogen, Kendra, Norman, Berthios, "Proliferation, hormonal responsiveness, and estrogen receptor content of MCF-7 human breast cancer cells grown in the short-term and long-term absence of estrogens," *Cancer Res.*, 47(16):43554360, 1987.

Kern et al., "Interaction of type IV collagen with the isolated integrins alpha 1 beta 1 and alpha 2 beta 1, " *Eur. J. Biochem.*, 215(1):151–159,1993.

Kingsman et al., "Replication in Saccharomyces cerevisiae of plasmid pBR313 carrying DNA from the yeast trpl region," Gene, 7(2): 141–152,1979.

Klein et al., "High-velocity microprojectiles for delivering nucleic acids into living cells," *Nature*, 327:7073, 1987.

Kliewer, Umesono, Mangelsdorf, Evans, "Retinoid X receptor interacts with nuclear receptors in retinoic acid, thyroid hormone and vitamin D3 signalling," Nature, 355 (6359): 446–449, 1992.

Kohler et al., "Continuous cultures of fused cells secreting antibody of predefined specificity," *Nature*, 256(5517):495–497,1975.

Kohler et al., "Derivation of specific antibody-producing tissue culture and tumor lines by cell fusion," *Eur. J. Immunol.*, 6(7):511–519,1976.

Kole, Akamatus, Ye et al., "Protein-tyrosine phosphatase inhibition by a peptide containing the phosphotyrosyl rninetic, L-O-malonyltyrosine," *Biochem. Biophys. Res. Commun.*, 209(3):817–822, 1995.

Kostrzynska et al., "Specific binding of collagen type IV to Streptococcus pyogenes," FEAFS *Microbiol. Lett.*, 59(1–2):229–233,1989.

Kuby, In: *Immunology*, 2nd Edition, W. H. Freeman & Company, New York, 1994.

Kuiper et al., "Steroid hormone receptor phosphorylation: is there a physiological role?," *Mol. Cell. Endocrinol.*, 100 (1–2):103–107, 1994.

Kumar and Chambon, "The estrogen receptor binds tightly to its responsive element as a ligand-induced homodimer," *Cell*, 55(1):145–156, 1988.

Kunkel, Roberts, Zakour "Rapid and efficient site-specific mutagenesis without phenotypic selection," *Meth. Enzymol.*, 154:367–382, 1987.

Kwoh et al., *Proc. Natl. Acad. Sci, USA*, 86(4):1173–1177, 1989.

Kyte and Doolittle, "A simple method for displaying the hydropathic character of a protein," *J. Mol. Biol.*, 157(1):105–132,1982.

Le Gal La Salle, G., J. J. Robert, S. Bemrwd, V. Ridoux, L. D. Stratford-Perricaudet M.

Penicaudet, and J. Mallet, "An adenovirus vector for gene transfer into neurons and glia in the brain," *Science*, 259:988–990, 1993.

LeDouarin, Zechel, Gamier, Lutz, Tora, Pierntt, Heery, Gronemeyer, Chambon, Losson, *EMBO J.*, 14:2020–2033, 1995.

Le Goff, Montano, Schodin, Katzenellenbogen, "Phosphorylation of the human estrogen receptor. Identification of hormone-regulated sites and examination of their influence on transcriptional activity," *J. Biol Chem.*, 269(6):4458–4466, 1994.

Levrero, M., V. Barban, S. Manteca, A. Ballay, C. Balsamo, M. L. Avantaggiati, G. Natoli, H. Skellekens, P. Tiollais, and M. Perricaudet, "Defective and nondefective adenovirus vectors for expressing foreign genes in vitro and in vivo," Gene 101:195–202, 1991.

Lopez-Berestein et al., "Liposomal amphotericin B for the treatment of systemic fungal infections in patients with cancer: a preliminary study" *J. Infect. Dis.*, 2151:704, 1985a.

Lopez-Berestein et al., "Protective effect of liposomal-amphotericin B against *C. albicans* infection in mice," *Cancer Drug Deliv.*, 2:183, 1985b.

Magee et al., "The interaction of cationic liposomes containing entrapped horseradish peroxidase with cells in culture," *J. Cell Biol.*, 63:492–504, 1974.

Maina, Riggs, Grandea, Slatlko, Moran, Tagliamonte, McReynolds, Guan, "An *Escherichia coli* vector to express and purify foreign proteins by fusion to and separation from maltose-binding protein," *Gene,* 74(2):365–373, 1988.

Maloy, et al., In: Microbial Genetics, 2nd Edition, Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Mann et al., "Construction of a retrovirus packaging mutant and its use to produce helper-free defective retrovirus," *Cell*, 33:153–159, 1983.

Macejak D G, Sarnow P, "Internal initiation of translation mediated by the 5' leader of a cellular mRNA," *Nature,* 353(6339):90–94, 1991.

Markowitz et al., "A safe packaging line for gene transfer: Separating viral genes on two different plasmids," *J. Virol.*, 62:1120–1124, 1988.

McGuire and Clark, "Prognostic factors and treatment decisions in axillary-node-negative breast cancer," *N. Engl. J. Med.*, 326(26):1756–1761, 1992.

Merrifield B., "Solid phase synthesis," *Science*, 232(4748):341–347, 1986.

Migliaccio et al., "Phosphorylation on tyrosine of in vitro synthesized human estrogen receptor activates its hormone binding," *Mol. Endocrinol.*, 3(7):1061–1069, 1989.

Mori and Fukatsu, "Anticonvulsant effect of DN-1417 a derivative of thyrotropin-releasing hormone and liposome-entrapped DN-1417 on amygdaloid-kindled rats," *Epilepsia*, 33(6):994–1000, 1992.

Nakamura et al., In: *Enzyme Immunoassays: Heterogenous and Homogenous Systems*, Chapter 27, 1987.

Nicholls et al., "Protein folding and association: insights from the interfacial and thermodynamic properties of hydrocarbons," *Proteins*, 11(4):281–296,1991.

Nicholson, Wright, Sainsbury, Halcrow, Kelly, Angus, Farndon, Harris, "Epidermal growth factor receptor (EGFr) as a marker for poor prognosis in node-negative breast cancer patients: neu and tamoxifen failure," *J. Steroid Biochem. Mol. Biol.*, 37(6):811–814, 1990.

Nicolas and Rubenstein, "Retroviral vectors," In: Rodriguez R L, Denhardt D T, (Eds.) Vectors:

A survey of molecular cloning vectors and their uses. Stoneham: Butterworth, pp. 493–513, 1988.

Nicolau and Gersonde, "Incorporation of inositol hexaphosphate into intact red blood cells, I. fusion of effector-containing lipid vesicles with eiythrocytes," *Naturwissenschaften (Germany)*, 66(11):563–566, 1979.

Nicolau and Sene, "Liposome-mediated DNA transfer in eukaryotic cells," *Biochim. Biophys. Acta*, 721:185–190, 1982.

Nowicki et al., "Short consensus repeat-3 domain of recombinant decay-accelerating factor is recognized by *Escherichia coli* recombinant Dr adhesin in a model of a cell-cell interaction," *J. Exp. Med*, 178(6):2115–2121,1993.

Oboum, Koszewski, Notides, "Hormone and DNA-binding mechanisms of the recombinant human estrogen receptor," *Biochemisty*, 32:6229–6236, 1993.

Ohara et a., *Proc. Natl. Acad. Sci. USA*, 86(15):5673–5677, 1989.

Onate, Prendergast, Wagner, Nissen, Reeves, Pettijohn, Edwards, Mol. Cell. Biol., 14:3376–3391, 1994.

Onate, Tsai, Tsai, O'Malley, "Sequence and characterization of a coactivator for the steroid hormone receptor superfamily," *Science*, 270:1354–1357, 1995.

Paskind et al., "Dependence of moloney murine leukemia virus production on cell growth," *Virology*, 67:242–248, 1975.

Pelletier, J. and Sonenberg, N., "Internal initiation of translation of eukaryotic mRNA directed by a sequence derived from poliovirus RNA," *Nature*, 334(6180):320–325, 1988.

Perales, J. C., Ferkol, T., Beegen, H., Ratnoff, O. D., and Hanson, R. W., *Proc. Natl. Acad. Sci. USA*, 91:4086–4090, 1994.

Pietras, "Heritable membrane alterations and growth associated with enhanced leupeptin-sensitive proteinase activity in epithelial cells exposed to dibutylnitrosamine," *Cancer Res.*, 38:1019–1030, 1978.

Pietras et al., "Steroid hormone-responsive, isolated endometrial cells," *Endocrino.*, 96(4):946–954, 1975.

Pietras, *Endocrino.*, 108:295, 1982.

Pietras and Szego, "Partial purification and characterization of oestrogen receptors in subfracyions of hepatocyte plasma membrane," *Biochem. J.*, 191:743–760, 1980.

Pietras R J, Fendly B M, Chazin V R, Pegram M D, Howell S B, Slamon D J, "Antibody to HER-2/neu receptor blocks DNA repair after cisplatin in human breast and ovarian cancer cells," *Oncogene*, 9(7):1829–1838, 1994.

Pietras R J, Arboleda J, Reese D M, Wongvipat M D, Ramos L, Gorman C M, Parker M G, Sliwkowski M X, Slamon D J, "HER-2 tyrosine kinase pathway targets estrogen receptor and promotes hormone-independent growth in human breast cancer cells," *Oncogene*, 10(12):2435–2446, 1995.

Pikul, Parks, Schneider, "In vitro killing of melanoma by liposome-delivered intracellular irradiation," *Arch. Surg.*, 122(12):1417–1420, 1987.

Pilz et al., "Mechanism of YadA-mediated serum resistance of *Yersinia enterocolitica* serotype O3," *Infect. Immun.*, 60(1):189–195, 1992.

Porath, Carlsson, Olsson, Belfrage, "Metal chelate affinity chromatography, a new approach to protein fractionation," *Nature*, 258(5536):598–599, 1975.

Potter et al., "Enhancer-dependent expression of human k immunoglobulin genes introduced into mouse pre-B lymphocytes by electroporation," *Proc. Natl. Acad Sci. USA*, 81:7161–7165, 1984.

Prokop and Bajpai, "Recombinant DNA Technology I," *Ann. N Y Acad. Sci., Vol.* 646, 1991.

Ragot, T., N. Vincent, P. Chafey, E. Vigne, H. Gilgenraantz, D. Couton, J. Cartaud, P. Briand, J.-C. Kaplan, M. Perricaudet, and A. Kahn. 1993. Efficient adenovirus-mediated transfer of a human minidystrophin gene to skeletal muscle of mdx mice, *Nature*, 361:647–650, 1993.

Read, Keith, Slamon, Katzenellenbogen, *Cancer Res.*, 50:3947–3951, 1990.

Reddy, Mangold, Tandon, Yoneda, Mundy, Zilberstein, Osborne, "Inhibition of breast cancer cell growth in vitro by a tyrosine kinase inhibitor," *Cancer Res.*, 52(13):3636–3641, 1992a.

Reddy, Mangold, Tandon, Yoneda, Mundy, Zilberstein, Osborne, *Cancer Res.*, 53:401A411, 1992b.

Rich et al., "Development and analysis of recombinant adenoviruses for gene therapy of cystic fibrosis," *Hum. Gene Ther.*, 4(4):461476, 1993.

Richardson, In: *Advances in Protein Chemistry*, Academic Press, Vol.34, pp.297–306,1981.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Riggs, In: *Current Protocols in Molecular Biology*, Ausubel et al. (Eds), Greene Associates/Wiley Interscience, N.Y., 1992.

Rippe et al., "DNA-mediated gene transfer into adult rat hepatocytes in primary culture," *Mol. Cell Biol.*, 10:689–695, 1990.

Rochette-Egly, Oulad-Abdelghani, Staub, Pfister, Scheuer, Chambon, Gaub, "Phosphorylation of the retinoic acid receptor-alpha by protein kinase A," *Mol. Endocrinol.*, 9(7): 860–871, 1995.

Rosenfeld, M. A., W. Siegfried, K. Yoshimura, K-Yoneyama, M. Fukayama, L. E. Stier, P. K. Paakko, P. Gilardi, L. Stratford-Perricaudet, M. Perricaudet, S. Jallat, A. Pavirani, J.-P. Lecocq, and R. G. Crystal, "Adenovirus-mediated transfer of a recombinant "1-antitrypsin gene to the lung epithelium in vivo," *Science*, 252:431–434, 1991.

Rosenfeld, M. A., K. Yoshimura, B. C. Trapnell, K-Yoneyama, E. R. Rosenthal, W. Dalemans, M. Fukayama, J. Bargon, L. E. Stier, L. Stratford-Perricaudet, M. Perricaudet, W. B. Guggino, A Pavirani, J.-P. Lecocq, and R. G. Crystal. "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Russell et al., "Transcriptional repression of the neu protooncogene by estrogen stimulated estrogen receptor," *Cancer Res.*, 52(23):66246629, 1992.

Ryden et al., "Specific binding of bone sialoprotein to Staphylococcus aureus isolated from patients with osteomyelitis," *Eur. J. Biochem.*, 184(2):331–336,1989.

Sack, *J. Mol. Graphics*, 6:224225,1988.

Sambrook et al., In: *Molecular Cloning: A Laboratory Manual*, 2nd Edition, Cold Spring Harbor Laboratory, Cold Spring Harbor, N.Y., Chapter 12.6,1989.

Santoro, "Identification of a 160,000 dalton platelet membrane protein that mediates the initial divalent cation-dependentadhesion of platelets to collagen," *Cell*, 46(6):913–920,1986.

Scatchard, *Ann. N.Y. Acad Sci.*, 51:660–672,1949.

Sculier et al., "Pilot study of amnphotericin B entrapped in sonicated liposomes in cancer patients with fungal infections," *Eur. J. Cancer Clin. Oncol.*, 24(3):527–538, 1988.

Segal, In: Biochemical Calculations, 2nd Edition, John Wiley and Sons, New York, 1976.

Shi, Liu, Lippman, Dickson, "Progestins and antiprogestins in mammary tunour growth and metastasis," *Human Reprod*, 9(1):162–173, 1994.

Shuai, Horvath, Huang, Qureshi, Cowbum, Darnell, "Interferon activation of the transcription factor Stat91 involves dimerization through SH2-phosphotyrosyl peptide interactions," *Cell*, 76(5):821–828, 1994.

Shuurmans, Bolt, Veldscholte, Mulder, "Regulation of growth of LNCaP human prostate tumor cells by growth factors and steroid hormones," *J. Steroid Biochem. Mol. Biol.*, 40(1–3):193–197, 1991.

Silvennoinen, Schindler, Schlessinger, Levy, "Ras-independent growth factor signaling by transcription factor tyrosine phosphorylation," *Science*, 261(5129):1736–1737, 1993.

Slamon, Clark, Wong, Levin, Ullrich, McGuire, "Human breast cancer: correlation of relapse and survival with amplification of the HER-2/neu oncogene," *Science*, 235 (4785):177–182, 1987.

Slamon, Godolphin, Jones, Holt, Wong, Keith, Levin, Sturt, Udove, Ullrich, Press, "Studies of the HER-2/neu proto-oncogene in human breast and ovarian cancer," *Science*, 244(4905):707–712, 1989a.

Slamon, Press, Godolphin, Jones, Holt, Stuart, Ulirich, *Cancer Cells*, 7:371–380, 1989b.

Sliwkowski, Schaefer, Akita, Lofgren, Fitzpatrick, Nuijens, Fendly, Cerione, Vandlen, Carraway, "Coexpression of erbB2 and erbB3 proteins reconstitues a high affinity receptor for heregulin," *J. Biol Chem.*, 269(20):14661–14665, 1994.

Smith and Johnson, "Single-step purification of polypeptides expressed in *Escherichia coli* as fusions with glutathione S-transferase," *Gene*, 67(1):31–40, 1988.

Smith, Merchant, Schurman, "In vitro cartilage degradation by *Escherichia coli* and *Staphylococcusaureus*," *Arthritis Rheum*, 25(4):441446,1982.

Smith et al., "The effect of antibodies on the destruction of cartilage in experimental infectious arthritis," *J. Bone Joint Surg. (Am.)*, 69(7):1063–1068,1987.

Smith, Conneely, O'Malley, "Modulation of the ligand-independent activation of the human estrogen receptor by hormone and antihormone," *Proc. Natl. Acad Sci. USA*, 90(13):6120–6124, 1993.

Smith, Conneely, O'Malley, "Oestrogen receptor activation in the absence of ligand," *Biochem. Soc. Trans.*, 23:935–939, 1995.

Smith, Van der Ploeg, Howard, Feighner, Cheng, Hickey, Wyvratt Jr., Fisher, Nargund, Patchett, "Peptidomimetic regulation of growth hormone secretion," *Endocr. Rev.*, 18(5):621–645, 1997.

Stewart et al., "Immunochemical studies on tobacco mosaic virus protein. IV. The automated solid-phase synthesis of a decapeptide of tobacco mosaic virus protein and its reaction with antibodies to the whole protein," Biochemistry, 5(11):3396–3400, 1966.

Stinchcomb et al., "Isolation and characterization of a yeast chromosomal replicator," *Nature*, 282(5734):39–43,1979.

Stratford-Perricaud et al., "Evaluation of the transfer and expression in mice of an enzyme-encoding gene using a human adenovirus vector," *Hum. Gene Ther.*, 1:241–256, 1990.

Stratford-Perricaudet and Perricaudet, "Gene transfer into animals: the promise of adenovirus," p. 51–61, In: *Human Gene Transfer*, Eds, 0. Cohen-Haguenauer and M. Boiron, Editions John Libbey Eurotext, France, 1991.

Szego and Pietras, "Lysosomal function in cellular activation: propagation of the actions of hormones and other effectors," *Int. Rev. Cytol.*, 88:1–302, 1984.

Takada and Hemler, "The primary structure of the VLA-2/collagen receptor alpha 2 subunit (platelet GPIa): homology to other integrins and the presence of a possible collagen-binding domain," *J. Cell Biol.*, 109(1):397–407, 1989.

Takagi et al., "Collagen-binding domain within bovine propolypeptide of von Willebrand factor," *J. Biol. Chem*, 266(9):5575–5579,1991.

Tamm et al., "Hydrophobic domains affect the collagen-binding specificity and surface polymerization as well as the virulence potential of the YadA protein of *Yersinia enterocolitica*," *Mol. Microbiol.*, 10(5):995–1011,1993.

Tang, DeVit, Johnston, "Genetic immunization is a simple method for eliciting an immune response," *Nature*, 356 (6365):152–154,1992.

Temnin, "Retrovirus vectors for gene transfer: Efficient integration into and expression of exogenous DNA in vertebrate cell genome," In: Kucherlapati R, ed. Gene transfer. New York: Plenum Press, pp. 149–188, 1986.

Trust et al., "High-affinity binding of the basement membrane protein collagen type IV to the crystalline virulence surface protein array of *Aeromonas salmonicida*," *Mol. Microbiol.*, 7(4):593–600,1993.

Tur-Kaspa et al., "Use of electroporation to introduce biologically active foreign genes into primary rat hepatocytes," *Mol. Cell Biol.*, 6(2):716–718, 1986.

Tschumper and Carbon, "Sequence of a yeast DNA fragment contauiing a chromosomal replicator and the TRP1 gene," *Gene*, 10(2):157–166,1980.

Turner and Tjian, "Leucine repeats and an adjacent DNA binding domain mediate the formation of functional cFos-cJun heterodimers," *Science*, 243(4899):1689–1694, 1989.

Ulmer et al., "Heterologous Protection Against Influenza by Injection of DNA Encoding a Viral Protein," *Science*, 259:1745–1749,1993.

van der Rest et al., "Collagen family of proteins," *FASEB. J.*, 5(13):2814–2823, 1991.

Varmus et al., "Retroviruses as mutagens: Insertion and excision of a nontransforming proviras alter the expression of a resident transforming provirus," *Cell*, 25:23–36, 1981.

Voss et al., "Synthesis of the protected tridecapeptide (56–68) of the VH domain of mouse myeloma immunoglobulin M603 and its reattachment to resin supports," Int J. Pept. Protein Res., 22(2):204–213, 1983.

Voytek et al., "Staphylococcal adhesion to collagen in intra-articular sepsis," *Biomaterials*, 9(1):107–110,1988.

Wagner, E., Zenke, M., Cotten, M., Beug, H., and Birnstiel, M. L. "Transferrin-polycation conjugates as carriers for DNA uptake into cells," *Proc. Natl. Acad Sci. USA*, 87:3410–3414, 1990.

Wagner et al., "Coupling of adenovirus to transferrin-polylysine/DNA complexes greatly enhances receptor-mediated gene delivery and expression of trausfected genes," *Proc.*
Natl. Acad. Sci. USA, 89(13):6099–6103,1992.

Wakeling, "Are breast tumours resistant to tamoxifen also resistant to pur antioestrogens?," *J. Steroid Biochem. Mol. Biol.*, 47(1–6):107–114, 1993.

Waldvogel et al., "Osteomyelitis:the past decade," N Engl. J. Med, 303(7):360–369,1980.

Walker et al., *Proc. Natl. Acad Sci. USA*, 89(1):392–396, 1992.

Wang, McVicar, Oppenheim, Kelvin, "Identificationof RANTES receptors on human monocytic cells: competition for binding and desensitization by homologous chemotactic cytokines," *J. Exp. Med.*, 177(3):699–705, 1993.

Wang et al., "Human recombinant macrophage inflammatory protein-1 alpha and -beta and monocyte chemotactic and activating factor utilize common and unique receptors on human monocytes," *J. Immnnol.*, 150(7):3022–3029, 1993.

Weis, Ekena, Thomas, Lazennec, Katzenellenbogen, "Constitutively active human estrogen receptors containing amino acid substitutions for tyrosine 537 in the receptor protein," *Mol. Endocrinol.*, 10:1388–1398, 1996.

Westerlund et al., "The Jul. 5X adhesin of uropathogenic *Escherichia coli* is a type IV collagen-binding protein," *Mol. Microbiol.*, 3(3):329–337,1989.

White, Sjoberg, Kalkhoven, Parker, "Ligand-independent activation of the oestrogen receptor by mutation of a conserved tyrosine," *EMBO J.*, 16:1427–1435, 1997.

Whitton et al., "A 'string-of-beads' vaccine, comprising linked minigenes, confers protection from lethal-dose virus challenge," *J. Virol.*, 67(1):348–352,1993.

Wolf et al., "An integrated family of amino acid sequence analysis programs," *Compu. Appl. Biosci.*, 4(1):187–191, 1988.

Wong et al., "Appearance of β-lactamase activity in animal cells upon liposome mediated gene transfer," *Gene*, 10:87–94, 1980.

Wong and Neumann, "Electric field mediated gene transfer," *Biochim. Biophys. Res. Commun.*, 107(2):584–587,1982.

Woody, *Peptides, Polypeptides, and Proteins*, New York, Wiley, 1974.

Wright, Nicholson, Angus, Sainsbury, Farmdon, Cairns, Harris, Horne, "Relationship between c-erbB-2 protein product expression and response to endocrine therapy in advanced breast cancer," *Br. J. Cancer*, 65(1):118–121, 1992.

Wu and Wu, "Receptor-mediated in vitro gene transfections by a soluble DNA carrier system," *J. Biol. Chem.*, 262:4429–4432, 1987.

Wu and Wu, "Evidence for targeted gene delivery to HepG2 hepatoma cells in vitro," *Biochemistry*, 27:887–892, 1988.

Wu and Wu, *Adv. Drug Delivery Rev.*, 12:159–167, 1993.

Xu, Qiu, DeMayo, Tsai, Tsai, O'Malley, "Partial hormone resistance in mice with disruption of the steroid receptor coactivator-1 (SRC-1) gene," *Science*, 279:1922–1925, 1998.

Yamaguchi et al., "Negative Regulation of Transforming Growth Factor-β by the Proteoglycan Decorin," *Nature*, (London), 346:281–284,1990.

Yang et al., "In vivo and in vitro gene transfer to mammalian somatic cells by particle bombardment," *Proc. Natl. Acad Sci. USA*, 87:9568–9572, 1990.

Yang and Russel, *Proc. Natl. Acad Sci. US*4, 87:4144–4148, 1990.

Ye and Burke Jr., "L-O-(2-Malonyl)tyrosine (L-OMT) a new phosphotyrosyl mimic suitably protected for solid-phase synthesis of signal transduction inhibitory peptides," *Tetrahedron Lett.*, 36:4733–4736, 1995.

Ye et al., "L-O-(2-Malonyl)tyrosine: a new phosphotyrosyl mimetic for the preparation of src homology 2 domain inhibitory peptides," *J. Med Chem.*, 38:4270–4275, 1995.

Zeillinger, Kury, Czerwenka, Kubista, Sliutz, Knogler, Huber, Zielinski, Reiner, Jakesz, Staffen, Reiner, Wrba, Spona, "HER-2 amplification, steroid receptors and epidermal growth factor receptor in primary breast cancer," *Oncogene*, 4(1):109–114, 1989.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims.

What is claimed is:

1. A composition comprising an isolated peptide of sequence SEQ ID NO:39.

2. A composition comprising an isolated peptide of between five and about 25 amino acid residues in length, wherein said peptide includes within its sequence an amino acid sequence represented by Leu-$AA_1$-Asp-Leu-Leu, wherein $AA_1$ is phosphotyrosine, or malonyltyrosine.

3. The composition of claim 2, wherein $AA_1$ is phosphotyrosine.

4. The composition of claim 2, wherein $AA_1$ is malonyltyrosine.

5. The composition of claim 2, wherein said peptide includes the amino acid sequence Pro-Leu-$AA_1$-Asp-Leu-Leu-Leu-Glu, wherein $AA_1$ is phosphotyrosine or malonyltyrosine.

6. The composition of claim 2 where said peptide is between five and about 10 amino acid residues in length.

7. The composition of claim 2, wherein said peptide is between seven and about 20 amino acid residues in length.

8. The composition of claim 2, wherein said peptide comprises the amino acid sequence of SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, or SEQ ID NO:34.

9. The composition of claim 2, wherein said peptide is linked to a carrier molecule.

10. The composition of claim 9, wherein said carrier molecule is BSA or KLH.

11. The composition of claim 2, further comprising a pharmaceutical excipient.

12. The composition of claim 2, wherein said peptide comprises from about 10% to about 99% by weight of said composition.

13. The composition of claim 2, wherein said peptide comprises from about 50% to about 95% by weight of said composition.

14. A method of treating a cancer cell, comprising delivering to a cancer cell a composition comprising an isolated peptide of between five and about 25 amino acid residues in length, wherein said peptide includes within its sequence an amino acid sequence represented by Leu-$AA_1$-Asp-Leu-Leu, wherein $AA_1$ is phosphotyrosine, or malonyltyrosine, whereby said composition decreases cell growth.

15. The method of claim 14, wherein said cancer cell is a human breast cancer cell.

16. The method of claim 14, wherein said cancer cell is comprised in a patient.

17. A method of treating a cancer cell, comprising delivering a composition comprising an isolated peptide of 25 amino acids in length or less having the amino acid sequence of SEQ ID NO:39 to a cancer cell, whereby said composition decreases cell growth.

18. A kit comprising, in suitable container means, a pharmaceutically-acceptable diluent and a therapeutically-effective amount of a composition comprising an isolated peptide of SEQ ID NO:39; or comprising an isolated peptide of between five and about 25 amino acid residues in length, wherein said peptide includes within its sequence an amino acid sequence represented by Leu-$AA_1$-Asp-Leu-Leu, wherein $AA_1$ is phosphotyrosine, or malonyltyrosine.

19. The kit of claim 18, comprising a single container means.

20. The kit of claim 18, wherein said composition and said diluent are present within distinct container means.

21. The kit of claim 18, wherein said composition is suitable for parenteral, intramuscular, or intravenous administration.

22. The kit of claim 18, comprising a composition suitable for oral or topical administration.

23. The kit of claim 18, further comprising an anticancer agent.

24. The kit of claim 23, wherein said anticancer agent is a peptide mimetic.

25. A method of killing a cancer cell, comprising providing to a cancer cell a therapeutically-effective amount of a composition comprising an isolated peptide of SEQ ID NO:39, or comprising an isolated peptide of between five and about 25 amino acid residues in length, wherein said peptide includes within its sequence an amino acid sequence represented by Leu-AA$_1$-Asp-Leu-Leu, wherein AA$_1$ is phosphotyrosine, or malonyltyrosine, whereby said composition kills said cell.

26. The method of claim 25, wherein said cancer cell is comprised within an animal.

27. A method for treating cancer in an animal, comprising administering to an animal with cancer, a therapeutically effective amount of a composition comprising an isolated peptide of SEQ ID NO:39; or comprising an isolated peptide of between five and about 25 amino acid residues in length, wherein said peptide includes within its sequence an amino acid sequence represented by Leu-AA$_1$-Asp-Leu-Leu, wherein AA$_1$ is phosphotyrosine, or malonyltyrosine, whereby said composition inhibits cancer cell growth.

28. The method of claim 27, wherein said composition is formulated in a pharmaceutical excipient for administration intravenously, parenterally, orally, topically, or as an inhalant, aerosol or spray.

29. The method of claim 27, wherein said animal is a human.

30. A method of treating cancer in an animal, said method comprising the steps of:
  (a) identifying an animal having increased estrogen receptor activity; and
  (b) administering to said animal a therapeutically-effective amount of a composition comprising an isolated peptide of SEQ ID NO:39; or comprising an isolated peptide of between five and about 25 amino acid residues in length, wherein said peptide includes within its sequence an amino acid sequence represented by Leu-AA$_1$-Asp-Leu-Leu, wherein AA$_1$ is phosphotyrosine, or malonyltyrosine, whereby said composition decreases cancer cell growth.

31. The method of claim 30, further comprising administering at least a second anticancer agent to said animal.

32. The composition of claim 2, wherein said peptide is comprised within a lipid composition.

33. The composition of claim 32, wherein said lipid composition comprises a lipid particle, a nanocapsule, a liposome, or lipid vesicle.

34. The composition of claim 1, wherein said peptide is linked to a carrier molecule.

35. The composition of claim 34, wherein said carrier molecule is BSA or KLH.

36. The composition of claim 1, wherein said peptide is comprised within a lipid composition.

37. The composition of claim 36, wherein said lipid composition comprises a lipid particle, a nanocapsule, a liposome, or lipid vesicle.

38. The composition of claim 1, further comprising a pharmaceutical excipient.

39. The composition of claim 1, wherein said peptide comprises from about 10% to about 99% by weight of said composition.

40. The composition of claim 1, wherein said peptide comprises from about 50% to about 95% by weight of said composition.

* * * * *

SEQUENCE LISTING

```
(1) GENERAL INFORMATION:

(iii) NUMBER OF SEQUENCES: 39

(2) INFORMATION FOR SEQ ID NO: 1:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 1:

Pro Leu Tyr Asp Leu Leu Leu Glu
1               5

(2) INFORMATION FOR SEQ ID NO: 2:

(i) SEQUENCE CHARACTERISTICS:
        (A) LENGTH: 8 amino acids
        (B) TYPE: amino acid
        (C) STRANDEDNESS:
        (D) TOPOLOGY: linear (ix) FEATURE:
        (A) NAME/KEY: Modified-site
        (B) LOCATION:3
        (D) OTHER INFORMATION:/note= "X = Phosphotyrosine"
```

(xi) SEQUENCE DESCRIPTION: SEQ ID NO: 2:

Pro Leu Xaa Asp Leu Leu Leu Glu
1               5

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS:
        (D) TOPOLOGY: linear (ix) FEATURE:
        (A) NAME/KEY: Modified-site
        (B) LOCATION:4
        (D) OTHER INFORMATION:/note= "X = Phosphotyrosine"

(xi) SEQUENCE DESCRIPTION: SEQ ID NO: 3:

Val Pro Leu Xaa Asp Leu Leu Leu Glu Met
1               5                   10

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS:
        (D) TOPOLOGY: linear (ix) FEATURE:
        (A) NAME/KEY: Modified-site
        (B) LOCATION:3
        (D) OTHER INFORMATION:/note= "X = Malonyltyrosine"

(xi) SEQUENCE DESCRIPTION: SEQ ID NO: 4:

Pro Leu Xaa Asp Leu Leu Leu Glu
1               5

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO: 5:

Val Pro Leu Tyr Asp Leu Leu Leu Glu Met
1               5                   10

(2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS:
        (D) TOPOLOGY: linear (ix) FEATURE:
        (A) NAME/KEY: Modified-site
        (B) LOCATION:4
        (D) OTHER INFORMATION:/note= "X = Malonyltyrosine"

(xi) SEQUENCE DESCRIPTION: SEQ ID NO: 6:

Val Pro Leu Xaa Asp Leu Leu Leu Glu Met
1               5                   10

(2) INFORMATION FOR SEQ ID NO: 7:

```
        (i) SEQUENCE CHARACTERISTICS:
            (A) LENGTH: 6 amino acids
            (B) TYPE: amino acid
            (C) STRANDEDNESS:
            (D) TOPOLOGY: linear (ix) FEATURE:
            (A) NAME/KEY: Modified-site
            (B) LOCATION:2
            (D) OTHER INFORMATION:/note= "X = Phosphotyrosine"

(xi) SEQUENCE DESCRIPTION: SEQ ID NO: 7:

Leu Xaa Asp Leu Leu Leu
1               5

(2) INFORMATION FOR SEQ ID NO: 8:

(i) SEQUENCE CHARACTERISTICS:
            (A) LENGTH: 6 amino acids
            (B) TYPE: amino acid
            (C) STRANDEDNESS:
            (D) TOPOLOGY: linear (ix) FEATURE:
            (A) NAME/KEY: Modified-site
            (B) LOCATION:2
            (D) OTHER INFORMATION:/note= "X = Malonyltyrosine"

(xi) SEQUENCE DESCRIPTION: SEQ ID NO: 8:

Leu Xaa Asp Leu Leu Leu
1               5

(2) INFORMATION FOR SEQ ID NO: 9:

(i) SEQUENCE CHARACTERISTICS:
            (A) LENGTH: 5 amino acids
            (B) TYPE: amino acid
            (C) STRANDEDNESS:
            (D) TOPOLOGY: linear (ix) FEATURE:
            (A) NAME/KEY: Modified-site
            (B) LOCATION:1
            (D) OTHER INFORMATION:/note= "X = Phosphotyrosine"

(xi) SEQUENCE DESCRIPTION: SEQ ID NO: 9:

Xaa Asp Leu Leu Leu
1               5

(2) INFORMATION FOR SEQ ID NO: 10:

(i) SEQUENCE CHARACTERISTICS:
            (A) LENGTH: 5 amino acids
            (B) TYPE: amino acid
            (C) STRANDEDNESS:
            (D) TOPOLOGY: linear (ix) FEATURE:
            (A) NAME/KEY: Modified-site
            (B) LOCATION:1
            (D) OTHER INFORMATION:/note= "X = Malonyltyrosine"

(xi) SEQUENCE DESCRIPTION: SEQ ID NO: 10:

Xaa Asp Leu Leu Leu
1               5

(2) INFORMATION FOR SEQ ID NO: 11:

(i) SEQUENCE CHARACTERISTICS:
            (A) LENGTH: 5 amino acids
            (B) TYPE: amino acid
```

```
            (C) STRANDEDNESS:
            (D) TOPOLOGY: linear (ix) FEATURE:
            (A) NAME/KEY: Modified-site
            (B) LOCATION:2
            (D) OTHER INFORMATION:/note= "X = Malonyltyrosine"

(xi) SEQUENCE DESCRIPTION: SEQ ID NO: 11:

Leu Xaa Asp Leu Leu
1               5

(2) INFORMATION FOR SEQ ID NO: 12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 12:

GATCCTAGAG GTCACAGTGA CCTACGA                                              27

(2) INFORMATION FOR SEQ ID NO: 13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 13:

GATCCTAGAG GTCACAGTGA CCTACGA                                              27

(2) INFORMATION FOR SEQ ID NO: 14:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO: 14:

AAGAACGTGG TGCCCCTCTT CGACCTGCTG CTGGAGATG                                 39

(2) INFORMATION FOR SEQ ID NO: 15:

(i) SEQUENCE CHARACTERISTICS:
            (A) LENGTH: 12 amino acids
            (B) TYPE: amino acid
            (C) STRANDEDNESS:
            (D) TOPOLOGY: linear (xi) SEQUENCE DESCRIPTION: SEQ ID NO: 15:

Pro Leu Tyr Asp Leu Leu Leu Glu Met Leu Asp Ala
1               5                  10

(2) INFORMATION FOR SEQ ID NO: 16:

(i) SEQUENCE CHARACTERISTICS:
            (A) LENGTH: 12 amino acids
            (B) TYPE: amino acid
            (C) STRANDEDNESS:
            (D) TOPOLOGY: linear (xi) SEQUENCE DESCRIPTION: SEQ ID NO: 16:

Pro Leu Tyr Asp Leu Leu Leu Glu Met Leu Asp Ala
1               5                  10
```

(2) INFORMATION FOR SEQ ID NO: 17:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 17:

Pro Leu Tyr Asp Leu Leu Leu Glu Met Leu Asp Ala
1               5                   10

(2) INFORMATION FOR SEQ ID NO: 18:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 18:

Pro Leu Tyr Asp Leu Leu Leu Glu Met Leu Asp Ala
1               5                   10

(2) INFORMATION FOR SEQ ID NO: 19:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 19:

Pro Leu Tyr Asp Leu Leu Leu Glu Met Leu Asp Ala
1               5                   10

(2) INFORMATION FOR SEQ ID NO: 20:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 20:

Pro Leu Tyr Asp Leu Leu Leu Glu Met Leu Asp Ala
1               5                   10

(2) INFORMATION FOR SEQ ID NO: 21:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 21:

Pro Leu Tyr Asp Leu Leu Leu Glu Met Leu Asp Ala
1               5                   10

(2) INFORMATION FOR SEQ ID NO: 22:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 22:

Pro Leu Tyr Asp Leu Leu Leu Glu Met Leu Asp Gly
1               5                   10

(2) INFORMATION FOR SEQ ID NO: 23:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 23:

Pro Leu Tyr Asp Leu Leu Leu Glu Met Leu Asp Gly
1               5                   10

(2) INFORMATION FOR SEQ ID NO: 24:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 24:

Pro Leu Tyr Asp Leu Leu Ile Glu Met Leu Asp Ala
1               5                   10

(2) INFORMATION FOR SEQ ID NO: 25:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 25:

Pro Val Tyr Asp Leu Leu Leu Glu Met Leu Asn Ala
1               5                   10

(2) INFORMATION FOR SEQ ID NO: 26:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 26:

Pro Val Tyr Asp Leu Leu Leu Glu Met Leu Asn Ala
1               5                   10

(2) INFORMATION FOR SEQ ID NO: 27:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 27:

Glu Phe Pro Glu Met Met Ser Glu Val Ile Ala Ala
1               5                   10

(2) INFORMATION FOR SEQ ID NO: 28:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 28:

Asp Phe Pro Glu Met Met Ala Glu Ile Ile Ser Val
1               5                   10

(2) INFORMATION FOR SEQ ID NO: 29:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 29:

Glu Phe Pro Glu Met Leu Ala Glu Ile Ile Thr Asn
1               5                   10

(2) INFORMATION FOR SEQ ID NO: 30:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 30:

Glu Phe Pro Ala Met Leu Val Glu Ile Ile Ser Asp
1               5                   10

(2) INFORMATION FOR SEQ ID NO: 31:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO: 31:

Pro Met His Lys Leu Phe Leu Glu Met Leu Glu Ala
1               5                   10

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 32:

Tyr Asp Leu Leu Leu Glu Met Leu
1               5

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS:
        (D) TOPOLOGY: linear (ix) FEATURE:
        (A) NAME/KEY: Modified-site
        (B) LOCATION:2..3

(D) OTHER INFORMATION:/note= "X = Any amino acid"

(xi) SEQUENCE DESCRIPTION: SEQ ID NO: 33:

Leu Xaa Xaa Leu Leu Leu
1               5

(2) INFORMATION FOR SEQ ID NO: 34:

(i) SEQUENCE CHARACTERISTICS:
        (A) LENGTH: 24 amino acids
        (B) TYPE: amino acid
        (C) STRANDEDNESS:
        (D) TOPOLOGY: linear (ix) FEATURE:
        (A) NAME/KEY: Modified-site
        (B) LOCATION:19
        (D) OTHER INFORMATION:/note= "X = Phosphotysine"

(xi) SEQUENCE DESCRIPTION: SEQ ID NO: 34:

Arg Gln Ile Lys Ile Trp Phe Gln Asn Arg Arg Met Lys Trp Lys Lys
1               5                   10                  15

Pro Leu Xaa Asp Leu Leu Leu Glu
            20

(2) INFORMATION FOR SEQ ID NO: 35:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO: 35:

Arg Gln Ile Lys Ile Trp Phe Gln Asn Arg Arg Met Lys Trp Lys Lys
1               5                   10                  15

(2) INFORMATION FOR SEQ ID NO: 36:

(i) SEQUENCE CHARACTERISTICS:
        (A) LENGTH: 8 amino acids
        (B) TYPE: amino acid
        (C) STRANDEDNESS:
        (D) TOPOLOGY: linear (ix) FEATURE:
        (A) NAME/KEY: Modified-site
        (B) LOCATION:3
        (D) OTHER INFORMATION:/note= "X = Phosphotyrosine"

(xi) SEQUENCE DESCRIPTION: SEQ ID NO: 36:

Pro Leu Xaa Asp Leu Leu Leu Glu
1               5

(2) INFORMATION FOR SEQ ID NO: 37:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 37:

Pro Leu Tyr Asp Leu Leu Leu Glu
1               5

(2) INFORMATION FOR SEQ ID NO: 38:

-continued

```
    (i) SEQUENCE CHARACTERISTICS:
        (A) LENGTH: 8 amino acids
        (B) TYPE: amino acid
        (C) STRANDEDNESS:
        (D) TOPOLOGY: linear (ix) FEATURE:
        (A) NAME/KEY: Modified-site
        (B) LOCATION:3
        (D) OTHER INFORMATION:/note= "X = Phosphotyrosine"

(xi) SEQUENCE DESCRIPTION: SEQ ID NO: 38:

Pro Leu Xaa Asp Ala Ala Leu Glu
1               5

(2) INFORMATION FOR SEQ ID NO: 39:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 39:

Leu Leu Arg Tyr Leu Leu Asp Lys
1               5
```